United States Patent
Blagg et al.

(10) Patent No.: US 11,708,319 B2
(45) Date of Patent: *Jul. 25, 2023

(54) BIPHENYL AMIDES WITH MODIFIED ETHER GROUPS AS HSP90 INHIBITORS AND HSP70 INDUCERS

(71) Applicant: THE UNIVERSITY OF KANSAS, Lawrence, KS (US)

(72) Inventors: Brian S. J. Blagg, Lawrence, KS (US); Rick T. Dobrowsky, Olathe, KS (US); Mercy Anyika, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/375,882

(22) Filed: Jul. 14, 2021

(65) Prior Publication Data
US 2022/0041543 A1  Feb. 10, 2022

Related U.S. Application Data

(62) Division of application No. 16/776,091, filed on Jan. 29, 2020, now Pat. No. 11,098,008, which is a division of application No. 15/321,289, filed as application No. PCT/US2015/037478 on Jun. 24, 2015, now Pat. No. 10,590,065.

(60) Provisional application No. 62/016,473, filed on Jun. 24, 2014.

(51) Int. Cl.
| C07D 311/12 | (2006.01) |
| C07C 233/18 | (2006.01) |
| C07D 309/10 | (2006.01) |
| C07H 15/203 | (2006.01) |
| C07D 307/20 | (2006.01) |
| C07D 311/08 | (2006.01) |
| C07D 311/16 | (2006.01) |

(52) U.S. Cl.
CPC .......... *C07C 233/18* (2013.01); *C07D 307/20* (2013.01); *C07D 309/10* (2013.01); *C07D 311/08* (2013.01); *C07D 311/16* (2013.01); *C07H 15/203* (2013.01); *C07C 2601/08* (2017.05); *C07C 2601/14* (2017.05); *C07C 2601/16* (2017.05)

(58) Field of Classification Search
CPC .............................. C07D 311/12; A61K 31/352
See application file for complete search history.

(56) References Cited

U.S. PATENT DOCUMENTS

| 7,608,594 | B2 | 10/2009 | Blagg et al. |
| 7,622,451 | B2 | 11/2009 | Blagg et al. |
| 7,811,998 | B2 | 10/2010 | Blagg et al. |
| 7,960,353 | B2 | 6/2011 | Blagg |
| 8,212,011 | B2 | 7/2012 | Blagg |
| 8,212,012 | B2 | 7/2012 | Blagg |
| 9,056,104 | B2 | 6/2015 | Blagg et al. |
| 9,120,774 | B2 | 9/2015 | Blagg et al. |
| 9,422,320 | B2 | 8/2016 | Blagg et al. |
| 10,030,041 | B2 | 7/2018 | Blagg et al. |
| 10,590,065 | B2 | 3/2020 | Blagg et al. |
| 10,590,157 | B2 | 3/2020 | Blagg et al. |
| 11,098,008 | B2 | 8/2021 | Blagg et al. |
| 2004/0063170 | A1 | 4/2004 | Fujikura et al. |
| 2006/0199776 | A1 | 9/2006 | Blagg et al. |
| 2007/0270452 | A1 | 11/2007 | Blagg et al. |
| 2008/0146547 | A1 | 6/2008 | Araldi et al. |
| 2009/0163709 | A1 | 6/2009 | Blagg |
| 2009/0187014 | A1 | 7/2009 | Blagg |
| 2010/0048882 | A1 | 2/2010 | Blagg et al. |

(Continued)

FOREIGN PATENT DOCUMENTS

| CN | 101679347 | 3/2010 |
| CN | 103596955 | 4/2014 |

(Continued)

OTHER PUBLICATIONS

Acute Leukemia, Merck Manual (Online Edition) 6 pages, pp. 1-6 (2013).*
Albermann, Christoph et al. "Substrate specificity of NovM: implications for novobiocin biosynthesis and glycorandomization." *Organic letters* 5.6 (2003): 933-936.
Alzheimer's disease, PubMed Health, Nov. 17, 2010.
Ansar et al., "A non-toxic Hsp90 inhibitor protects neurons from Aβeta-induced toxicity," *Bioorg Med Chem Lett*, 17(7):1984-90, 2007.
Anyika et al., "Development of Noviomimetics as C-Terminal Hsp90 Inhibitors", *ACS Medicinal Chemistry Letters*, 7: 67-71, 2016.

(Continued)

*Primary Examiner* — Deepak R Rao
(74) *Attorney, Agent, or Firm* — Parker Highlander PLLC

(57) ABSTRACT

Provided herein are compounds of the formulas:

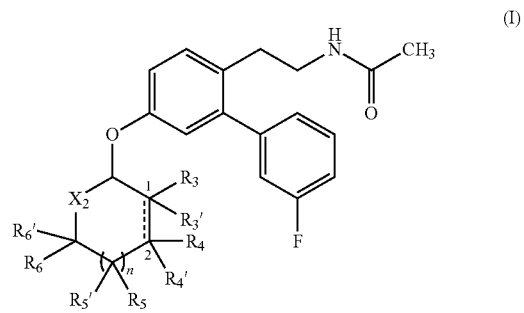

(I)

wherein: n, $X_2$, $R_3$, $R_3'$, $R_4$, $R_4'$, $R_5$, $R_5'$, $R_6$, and $R_6'$ are as defined herein. Pharmaceutical compositions of the compounds are also provided. In some aspects, these compounds may be used for the treatment of diseases, including diabetic peripheral neuropathy or cancer.

19 Claims, 4 Drawing Sheets

(56) References Cited

U.S. PATENT DOCUMENTS

| | | |
|---|---|---|
| 2010/0105630 A1 | 4/2010 | Blagg |
| 2011/0082098 A1 | 4/2011 | Calvet et al. |
| 2012/0252745 A1 | 10/2012 | Blagg et al. |
| 2012/0309702 A1 | 12/2012 | Blagg et al. |
| 2013/0116227 A1 | 5/2013 | Katayama et al. |
| 2015/0057240 A1 | 2/2015 | Blagg et al. |
| 2017/0051000 A1 | 2/2017 | Blagg et al. |
| 2019/0023730 A1 | 1/2019 | Blagg et al. |

FOREIGN PATENT DOCUMENTS

| | | |
|---|---|---|
| WO | WO 2006/050501 | 5/2006 |
| WO | WO 2007/025943 | 3/2007 |
| WO | WO 2008/115719 | 9/2008 |
| WO | WO 2010/096650 | 8/2010 |
| WO | WO 2011/041593 | 4/2011 |
| WO | WO 2012/138896 | 10/2012 |
| WO | WO 2012/163054 | 11/2012 |
| WO | WO 2013/119985 | 8/2013 |
| WO | WO 2015/200514 | 12/2015 |

OTHER PUBLICATIONS

Avila et al., "High-throughput screening for Hsp90 ATPase inhibitors," *Bioorg Med. Chem. Lett.*, 16(11):3005-08, 2006.

Bosseray et al., "What's new in vaccines against herpes simplex infections?", *Pathol. Biol.*, 50(8):483-492, 2002.

Burlison and Blagg, "Synthesis and Evaluation of Coumermycin A1 Analogues that Inhibit the Hsp90 Protein Folding Machinery," *J. Org. Chem.*, 8:4855, 2006.

Burlison et al., "Development of Novobiocin Analogues That Manifest Anti-proliferative Activity against Several Cancer Cell Lines," *J. Org. Chem.*, 73:2130, 2008.

Burlison et al., "Novobiocin: Redesigning a DNA Gyrase Inhibitor for Selective Inhibition of Hsp90," *J. Am. Chem. Soc.*, 128:15529, 2006.

Calkins et al., "The Nrf2/ARE Pathway as a Potential Therapeutic Target in Neurodegenerative Disease," *Antioxid. Redox Signal.*, 11(3):497-508, 2009.

Cohen et al., "Novel C-Terminal Hsp90 Inhibitor for Head and Neck Squamous Cell Cancer (HNSCC) with in vivo Efficacy and Improved Toxicity Profiles Compared with Standard Agents," *Ann. Surg. Oncol.*, 19(Suppl. 3):S483, 2012.

Comer et al., "Characterization of a novel novobiocin analogue as a putative C-terminal inhibitor of heat shock protein 90 in prostate cancer cells," *Prostate*, 70(1):27-36, 2010.

Damasio, "Alzheimer's Disease and related dementias", In: Cecil Textbook of Medicine, 20th Edition, 2:1992-1996, 1996.

Donnelly and Blagg, "Novobiocin and additional inhibitors of the Hsp90 C-terminal nucleotide-binding pocket," *Curr. Med. Chem.*, 15(26):2702-17, 2008.

Donnelly et al., "Cytotoxic sugar analogues of an optimized novobiocin scaffold," *MedChemComm*, 1(2):165-170, 2010.

Donnelly et al., "The Design, Synthesis, and Evaluation of Coumarin Ring Derivatives of the Novobiocin Scaffold that Exhibit Antiproliferative Activity," *J. Org. Chem.*, 73:8901, 2008.

Douglas, Jr., "Introduction to Viral Diseases", In: Cecil Textbook of Medicine, 20th Edition, 2:1739-1747, 1996.

Eikelenboom et al., "Inflammatory mechanisms in Alzheimer's disease," *Trend. Pharmacol. Sci.*, 15(12):447-450, 1994.

Farmer et al., "KU-32, a novel drug for diabetic neuropathy, is safe for human islets and improves in vitro insulin secretion and viability," *Experimental Diabetes Research*, 671-673, 2012.

Forsberg et al., "Modified buphenyl Hsp90 C-terminal inhibitors for the treatment of cancer," *Bioorg. Med. Chem. Lett.*, Article in Press, 2017.

Goff, "Intracellular trafficking of retroviral genomes during the early phase of infection: viral exploitation of cellular pathways", *J. Gene Med.*, 3(6):517-528), 2001.

Gura et al., "Systems for identifying new drugs are often faulty", *Science*, 278:1041-1042, 1997.

Hadden et al., "Synthesis and evaluation of Hsp90 inhibitors that contain the 1,4-naphthoquinone scaffold," *Bioorg Med Chem.*, 17(2):634-40, 2009.

Huang and Blagg, "A library of noviosylated coumarin analogues," *J. Org. Chem.*, 72(10):3609-3613, 2007.

Huang et al., "Molecular Design of Anticancer Drug Leads Based on Three-Dimensional Quantitative Structure-Activity Relationship," *J. Chem. Info. Modeling*, 51(8):1999-2006, 2011.

International Preliminary Report on Patentability issued in International Application No. PCT/US2013/025387, dated Aug. 12, 2014.

International Search Report and Written Opinion issued in International Application No. PCT/US2013/025387, dated Apr. 2, 2013.

International Search Report for PCT Application No. PCT/US2015/037478, dated Jan. 14, 2016.

Johnson et al., "Relationships between dmg activity in NCI preclinical in vitro and in vivo models and early clinical trials", *Br. J. Cancer*, 84(10):1424-1431, 2001.

Kusuma et al., "Synthesis and Evaluation of Novologues as C-Terminal Hsp90 Inhibitors with Cytoprotective Activity against Sensory Neuron Glucotoxicity," *J. Med. Chem.*, 55:5797, 2012.

Kusuma et al., "Targeting the Heat Shock Protein 90 Dimer with Dimeric Inhibitors", *Journal of Medicinal Chemistry*,54(18):6234-6253, 2011.

Layzer, "Degenerative diseases of the nervous system", Cecil Textbook of Medicine, 20th Edition, vol. 2, pp. 2050-2057, 1996.

Lu et al., "Neuroprotective activity and evaluation of Hsp90 inhibitors in an immortalized neuronal cell line," *Bioorg. Med. Chem.*, 17(4):1709-15, 2009.

Ma et al., "Heat Shock Protein 70 Is Necessary to Improve Mitochondrial Bioenergetics and Reverse Diabetic Sensory Neuropathy following KU-32 Therapy," *J. Pharmacol. Exp. Ther.*, 348:281-292, 2014.

Ma et al., "Modulating Molecular Chaperones Improves Mitochondrial Bioenergetics and Decreases the Inflammatory Transcriptome in Diabetic Sensory Neurons," *ACS Chem. Neurosci.*, 6(9):1637-1648, 2015.

Marcu et al., "Novobiocin and related coumarins and depletion of heat shock protein 90-dependent signaling proteins," *J. Natl. Cancer Inst*, 92:242-248, 2000.

Matts et al., "Elucidation of the Hsp90 C-Terminal Inhibitor Binding Site", *ACS Chem Biol.*, 6(8):800-807, 2011.

Mayer et al., "Hsp70 chaperones: cellular functions and molecular mechanism", *Cell Mol Life Sci.*, 62 (6): 670-84, 2005.

Mays et al., "The synthesis and evaluation of flavone and isoflavone chimeras of novobiocin and dembone," *Bioorg Med. Chem.*, 18(1):249-66, 2010.

Moroni et al., "Exploiting Conformational Dynamics in Dmg Discovery: Design of C-Terminal Inhibitors of Hsp90 with Improved Activities," *J. Chem. Info. Modeling*, 54(1):195-208, 2014.

Office Communication issued in Chinese Application No. 201580033560.X, dated Aug. 3, 2018.

Office Communication issued in corresponding Chilean Application No. 201802367, dated Sep. 5, 2019.

Office Communication issued in corresponding Chinese Application No. 201380019057.X, dated Jul. 24, 2015. [English Translation].

Office Communication issued in corresponding Eurasian Application No. 201491496, dated Aug. 10, 2015. [English Translation].

Office Communication issued in corresponding European Application No. 13706822.7, dated Jun. 22, 2015.

Office Communication issued in U.S. Appl. No. 14/377,616, dated Oct. 1, 2015.

Office Communication issued in U.S. Appl. No. 14/377,616, dated Feb. 2, 2016.

Parkinson's: Overview—PubMed Health, Apr. 8, 2015.

Pearce et al., "Failure modes in anticancer drug discovery and development", In: Cancer Drug Design and Discovery, Chapter 18, pp. 424-435, 2008.

Peterson and Blagg, "Click chemistry to probe Hsp90: synthesis and evaluation of a series of triazole-containing novobiocin analogues," *Bioorg Med Chem Lett*, 20(13):3957-60, 2010.

(56) References Cited

OTHER PUBLICATIONS

Peterson and Blagg, "To fold or not to fold: modulation and consequences of Hsp90 inhibition", *Future Med Chem.*, 1 (2): 267-283, 2009.
Razonable et al., "Herpesvirus infections in transplant recipients: current challenges in the clinical management of cytomegalovirus and Epstein-Barr virus infections", *Herpes*, 10(3):60-65, 2003.
Roos, "Huntington's disease: a clinical review," *Orphanet J. Rare Dis.*, 5(40):1-8, 2010.
Sadikot et al., "Development of a High-Throughput Screening Cancer Cell-Based Luciferase Refolding Assay for Identifying Hsp90 Inhibitors," *Assay and Drug Development Technologies*, 11(8):478-488, 2013.
Shelton et al., "KU135, a Novel Novobiocin-Derived C-Terminal Inhibitor of the 90-kDa Heat Shock Protein, Exerts Potent Antiproliferative Effects in Human Leukemic Cells," *Mol. Pharmacol.*, 76:1314, 2009.
Shen et al., "Synthesis of photolabile novobiocin analogues," *BioorgMed Chem Lett*, 14(23):5903-5906, 2004.
Simone, "Oncology: Introduction", In: Cecil Textbook of Medicine, 20th Edition, 1:1004-1010, 1996.
Urban et al., "Inhibiting Heat Shock Protein 90 Reverses Sensory Hypoalgesia in Diabetic Mice", *ASN Neuro.*, 2(4): 189-199, 2010.
Urban et al., "Modulating Molecular Chaperones Improves Sensory Fiber Recovery and Mitochondrial Function in Diabetic Peripheral Neuropathy," *Experimental Neurology*, 235(1):388-396, 2012.
Vincent et al., "Cell culture modeling to test therapies against hyperglycemia-mediated oxidative stress and injury", *Antioxid Redox Signal*, 7:(11-12):1494-1506, 2005.
Vincent et al., "Sensory Neurons and Schwann Cells Respond to Oxidative Stress by Increasing Antioxidant Defense Mechanisms", *Antioxid Redox Signal*, 11:425-438, 2009.
Yu et al., "Hsp90 Inhibitors Identified from a Library of Novobiocin Analogues," *J. Am. Chem. Soc.*, 127:12778, 2005.
Yu et al., "Hyperglycemia and downregulation of caveolin-1 enhance neuregulin-induced demyelination", *Glia*, 56: 877-887, 2008.
Yu et al., "Synthesis of Mono- and Dihydroxylated Furanoses, Pyranoses, and an Oxepanose for the Preparation of Natural Product Analogue Libraries," *J. Org. Chem.*, 70:5599-5605, 2005.
Zhang et al, "Hyperglycemia alters the schwann cell mitochondrial proteome and decreases coupled respiration in the absence of superoxide production", *J Proteome Res.*, 9(1):458-71, 2010.
Zhang et al., "C-Terminal Heat Shock Protein 90 Inhibitor Decreases Hyperglycemia-induced Oxidative Stress and Improves Mitochondrial Bioenergetics in Sensory Neurons," *J. Proteome Research*, 11(4):2581-2593, 2012.
Zhang et al., "Simplified aminocoumarin analogues as anticancer agents: Amino isosteric replacement in the noviose moiety resulted in substantial enhancement of antiproliferative activity," *Chinese Chemical Letters*, 24(8):719-722, 2013.
Zhao and Blagg, "Novobiocin analogues with second-generation noviose surrogates," *Bioorg & Med. Chem. Lett.*, 23(2):552-557, 2013.
Zhao and Blagg, in: *Inhibitors of Molecular Chaperones as Therapeutic Agents*, Ed: Timothy Machajewski, RSC Publishing:London, 2014.
Zhao et al., "3-Arylcoumaiin Derivatives Manifest Anti-Proliferative Activity through Hsp90 Inhibition," *ACS Med. Chem. Lett.*, 3(4):327-331, 2012.
Zhao et al., "3D-QSAR-assisted design, synthesis and evaluation of novobiocin analogues", *ACS Med Chem Lett.*, 4(1): 57-62, 2013.
Zhao et al., "Design, synthesis and biological evaluation of biphenylamide drivatives as Hsp90 C-terminal inhibitors," *European Journal of Medicinal Chemistry*, 89:442-466, 2014.
Zhao et al., "Engineeiing an Antibiotic to Fight Cancer: Optimization of the Novobiocin Scaffold to Produce Anti-proliferative Agents," *J. Med. Chem.*, 54:3839-3853, 2011.
Zhao et al., "Identification of a New Scaffold for Hsp90 C-Terminal Inhibition," *ACS Med. Chem. Lett.*, 5(1):84-88, 2014.
Zhao et al., "Novologues containing a benzamide side chain manifest anti-proliferative activity against two breast cancer cell lines", *Bioorg. Med. Chem. Lett.*, 24:3633-3637, 2014.
Zhao et al., "Synthesis and Evaluation of Noviose Replacements on Novobiocin that Manifest Anti-proliferative activity," *ACS Med Chem Lett.*, 1(7):311-315, 2010.

\* cited by examiner

BIPHENYL AMIDES WITH MODIFIED ETHER GROUPS AS HSP90 INHIBITORS AND HSP70 INDUCERS

This application is a divisional of U.S. application Ser. No. 16/776,091, filed Jan. 29, 2020, which is a divisional of U.S. application Ser. No. 15/321,289, now U.S. Pat. No. 10,590,065, filed Dec. 22, 2016, as a national phase application under 35 U.S.C. § 371 of International Application No. PCT/US2015/037478, filed Jun. 24, 2015, which claims the benefit of U.S. Provisional Application 62/016,473, filed on Jun. 24, 2014, the entire content of which are incorporated herein by reference.

This invention was made with government support under CA109265, DK095911, and NS075311 awarded by the National Institutes of Health. The government has certain rights in the invention.

BACKGROUND OF THE INVENTION

I. Field of the Invention

The present invention relates generally to the fields of biology, chemistry, and medicine. More particularly, it concerns compounds, compositions and methods for the treatment and prevention of diseases such as cancer and other proliferative diseases.

II. Description of Related Art

Neckers and coworkers reported that the DNA gyrase inhibitor, novobiocin, and related natural products bind to the Hsp90 C-terminus nucleotide binding pocket with low affinity ($IC_{50}$~700 µM) (Marcu, et al., 2000). Subsequent modifications to novobiocin, including to the coumarin scaffold and the benzamide side chain, led to several compounds with increased inhibitory activity (Zhao, et al., 2014; Shelton, et al., 2009; Cohen, et al., 2012; Burlison, et al., 2008; Burlison and Blagg, 2006; Burlison, et al., 2006; Donnelly, et al., 2008; Yu, et al., 2005a). Previous studies have shown that the coumarin core of novobiocin can be replaced with a biphenyl core (Kusuma, et al., 2012). While the initial biphenyl analogs contained a noviose sugar moiety, this sugar group is synthetically challenging, requiring as many as 10 steps to obtain (Yu, et al., 2005b; Beaver, et al., 2008; Zhao, et al., 2011). Thus, replacing this group without sacrificing activity or other pharmacological properties is of commercial interest. In general, development of new novobiocin compounds continues to be of interest because the biological activity profiles of these compounds vary, the wide variety of potential diseases and disorders that may be treated or prevented with these compounds, and manufacturing and supply-chain related considerations.

SUMMARY OF THE INVENTION

The present disclosure provides biphenyl Hsp90 inhibitors with modified ether groups with therapeutic properties, pharmaceutical compositions thereof, methods for their manufacture, and methods for their use.

In some aspects, the present disclosure provides compounds of the formula:

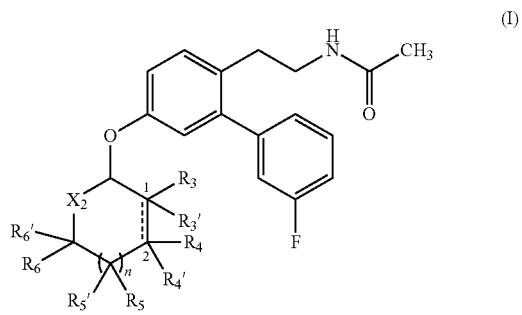

wherein:
the bond between atom 1 and atom 2 is either a single bond or a double bond; $X_2$ is —$CH_2$— or —O—;
$R_3$, $R_4$, $R_3'$, $R_4'$ are each independently hydrogen, hydroxy, alkoxy$_{(C\leq12)}$, aryloxy$_{(C\leq12)}$, aralkoxy$_{(C\leq12)}$, substituted alkoxy$_{(C\leq12)}$, substituted aryloxy$_{(C\leq12)}$, or substituted aralkoxy$_{(C\leq12)}$;
each $R_5$ and $R_5'$ are each independently hydrogen, hydroxy, or alkyl$_{(C\leq12)}$, aryloxy$_{(C\leq12)}$, aralkoxy$_{(C\leq12)}$, heteroaryloxy$_{(C\leq12)}$, heteroaralkoxy$_{(C\leq12)}$, or a substituted version of any of these groups;
$R_6$ and $R_6'$ are each independently hydrogen, alkyl$_{(C\leq12)}$, cycloalkyl$_{(C\leq12)}$, substituted alkyl$_{(C\leq12)}$, or substituted cycloalkyl$_{(C\leq12)}$; and
n is 0, 1, or 2; provided that if n is 2, then each $R_5$ and $R_5'$ on each methylene are independently selected;
or a pharmaceutically acceptable salt thereof.

In another aspect, the present disclosure provides compounds of the formula:

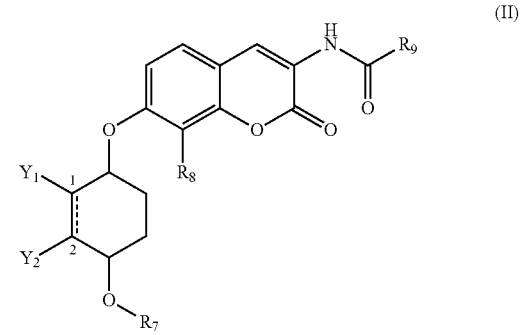

wherein:
$R_7$ is aryl$_{(C\leq12)}$, aralkyl$_{(C\leq12)}$, or a substituted version of either of these groups;
$R_8$ is hydrogen, alkyl$_{(C\leq12)}$, cycloalkyl$_{(C\leq12)}$, substituted alkyl$_{(C\leq12)}$, or substituted cycloalkyl$_{(C\leq12)}$;
$R_9$ is alkyl$_{(C\leq12)}$, cycloalkyl$_{(C\leq12)}$, aryl$_{(C\leq12)}$, heteroaryl$_{(C\leq12)}$, or a substituted version of any of these groups; and
$Y_1$ and $Y_2$ are each independently hydrogen or hydroxy;
or a pharmaceutically acceptable salt thereof.

In some embodiments, the bond between atom 1 and atom 2 in formula I is a single bond. In other embodiments, the bond between atom 1 and atom 2 in formula I is a double bond. In some embodiments, $X_2$ is —$CH_2$—. In other embodiments, $X_2$ is —O—.

In some embodiments, $R_3$ is hydrogen. In other embodiments, $R_3$ is hydroxy. In some embodiments, $R_3'$ is hydrogen. In other embodiments, R$_3$' is hydroxy. In some embodiments, R$_4$ is hydrogen. In other embodiments, R$_4$ is hydroxy. In other embodiments, R$_4$ is aralkoxy$_{(C\leq12)}$ or substituted aralkoxy$_{(C\leq12)}$. In some embodiments, R$_4$ is benzyloxy. In some embodiments, R$_4$' is hydrogen. In other embodiments, R$_4$' is hydroxy. In other embodiments, R$_4$' is aralkoxy$_{(C\leq12)}$ or substituted aralkoxy$_{(C\leq12)}$. In some embodiments, R$_4$' is benzyloxy.

In some embodiments, R$_5$ is hydrogen. In other embodiments, R$_5$ is hydroxy. In other embodiments, R$_5$ is aralkoxy$_{(C\leq12)}$ or substituted aralkoxy$_{(C\leq12)}$. In some embodiments, R$_5$ is aralkoxy$_{(C\leq12)}$. In some embodiments, R$_5$ is benzyloxy, 1-(2-napthyl)methoxy, 2-methylphenylmethoxy, 4-methylphenylmethoxy, or 4-t-butylphenylmethoxy. In other embodiments, R$_5$ is substituted aralkoxy$_{(C\leq12)}$. In some embodiments, R$_5$ is 2-fluorophenylmethoxy, 2-bromophenylmethoxy, 2-chlorophenylmethoxy, 2-methoxyphenylmethoxy, 3-bromophenylmethoxy, 3-chlorophenylmethoxy, 3-methoxyphenylmethoxy, 4-fluorophenylmethoxy, 4-chlorophenylmethoxy, 4-bromophenylmethoxy, 4-methoxyphenylmethoxy, 4-trifluoromethylphenylmethoxy, 2,6-dichlorophenylmethoxy, 4-chloro-2-methoxyphenylmethoxy, 2-methoxy-4-methylphenylmethoxy, or 2-bromo-4-chlorophenylmethoxy. In other embodiments, R$_5$ is alkyl$_{(C\leq12)}$ or substituted alkyl$_{(C\leq12)}$. In some embodiments, R$_5$ is t-butyl.

In some embodiments, R$_5$' is hydrogen. In other embodiments, R$_5$' is hydroxy. In other embodiments, R$_5$' is aralkoxy$_{(C\leq12)}$ or substituted aralkoxy$_{(C\leq12)}$. In some embodiments, R$_5$' is aralkoxy$_{(C\leq12)}$. In some embodiments, R$_5$' is benzyloxy, 1-(2-napthyl)methoxy, 2-methylphenylmethoxy, 4-methylphenylmethoxy, or 4-t-butylphenylmethoxy. In other embodiments, R$_5$' is substituted aralkoxy$_{(C\leq12)}$. In some embodiments, R$_5$' is 2-fluorophenylmethoxy, 2-bromophenylmethoxy, 2-chlorophenylmethoxy, 2-methoxyphenylmethoxy, 3-bromophenylmethoxy, 3-chlorophenylmethoxy, 3-methoxyphenylmethoxy, 4-fluorophenylmethoxy, 4-chlorophenylmethoxy, 4-bromophenylmethoxy, 4-methoxyphenylmethoxy, 4-trifluoromethylphenylmethoxy, 2,6-dichlorophenylmethoxy, 4-chloro-2-methoxyphenylmethoxy, 2-methoxy-4-methylphenylmethoxy, or 2-bromo-4-chlorophenylmethoxy. In other embodiments, R$_5$' is alkyl$_{(C\leq12)}$ or substituted alkyl$_{(C\leq12)}$. In some embodiments, R$_5$' is t-butyl.

In some embodiments, R$_6$ is hydrogen. In other embodiments, R$_6$ is alkyl$_{(C\leq12)}$ or substituted alkyl$_{(C\leq12)}$. In some embodiments, R$_6$ is methyl. In some embodiments, R$_6$' is hydrogen. In other embodiments, R$_6$' is alkyl$_{(C\leq12)}$ or substituted alkyl$_{(C\leq12)}$. In some embodiments, R$_6$' is methyl. In some embodiments, n is 0. In other embodiments, n is 1.

In some embodiments, the bond between atom 1 and atom 2 in formula II is a single bond. In other embodiments, the bond between atom 1 and atom 2 in formula II is a double bond. In some embodiments, Y$_1$ is hydrogen. In other embodiments, Y$_1$ is hydroxy. In some embodiments, Y$_2$ is hydrogen. In other embodiments, Y$_2$ is hydroxy.

In some embodiments, R$_8$ is alkyl$_{(C\leq12)}$. In some embodiments, R$_8$ is methyl. In other embodiments, R$_9$ is alkyl$_{(C\leq12)}$. In some embodiments, R$_9$ is methyl. In some embodiments, R$_7$ is aralkyl$_{(C\leq12)}$ or substituted aralkyl$_{(C\leq12)}$. In some embodiments, R$_7$ is aralkyl$_{(C\leq12)}$. In some embodiments, R$_7$ is benzyl. In other embodiments, R$_7$ is substituted aralkyl$_{(C\leq12)}$. In some embodiments, R$_7$ is 4-chlorophenylmethyl, 2-bromophenylmethyl, or 2-methoxyphenylmethyl.

In some embodiments, the compounds are further defined as:

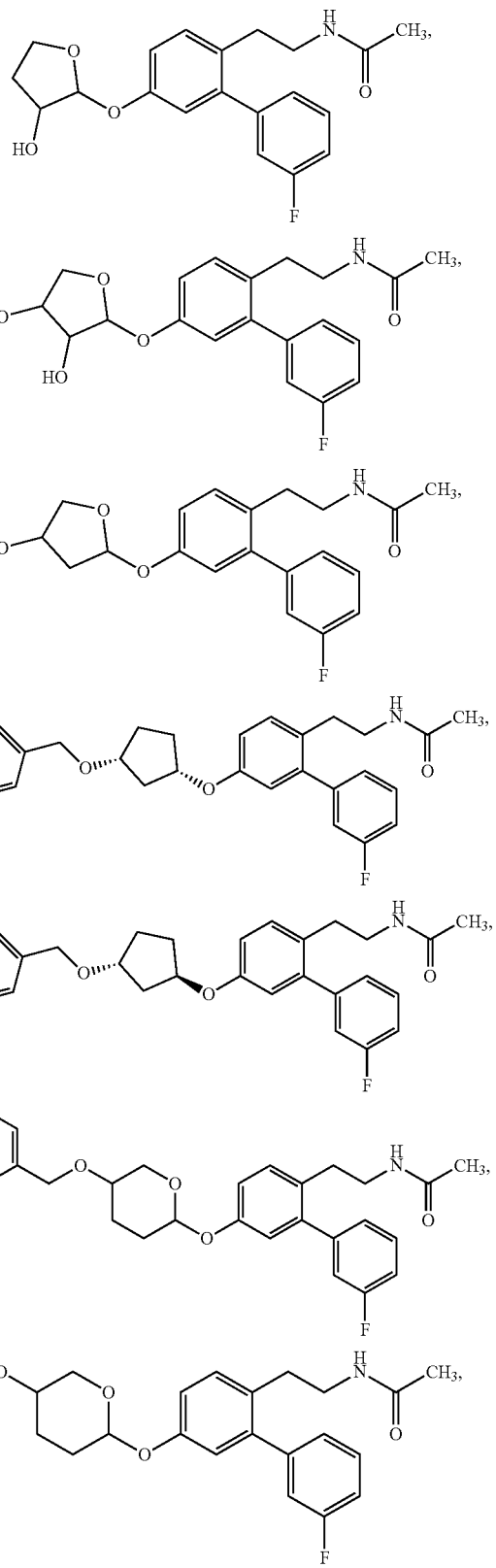

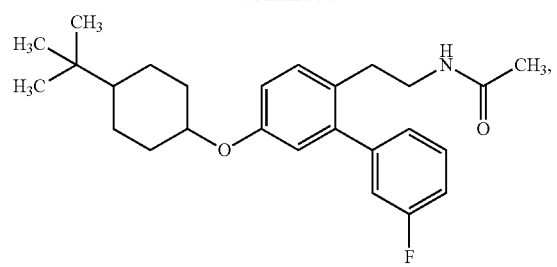
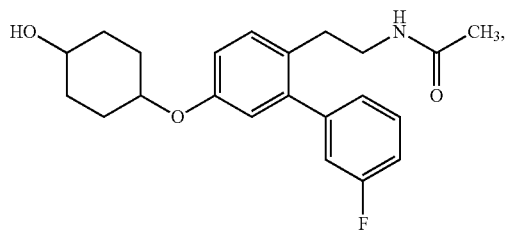
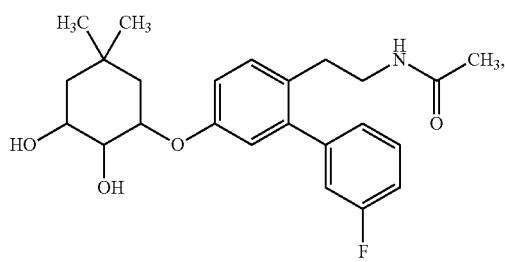
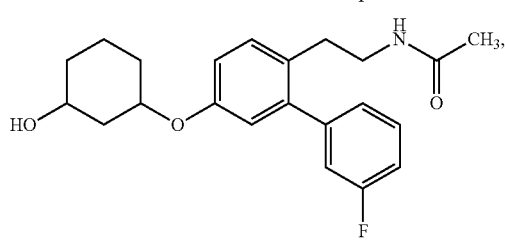
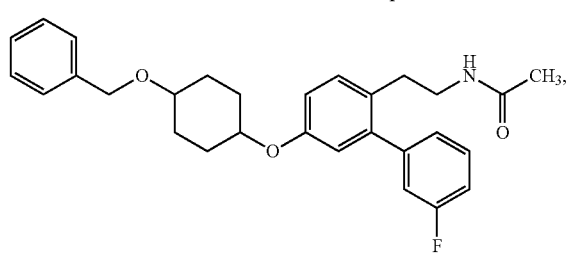
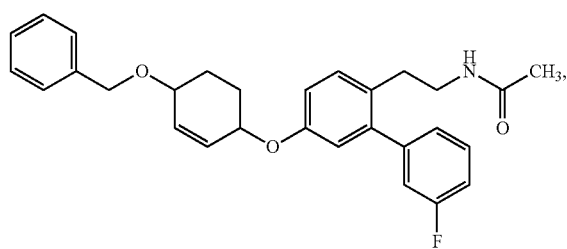
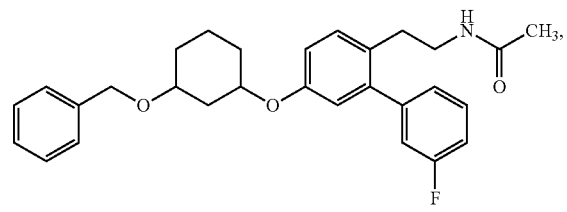
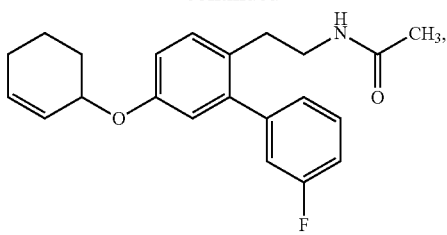
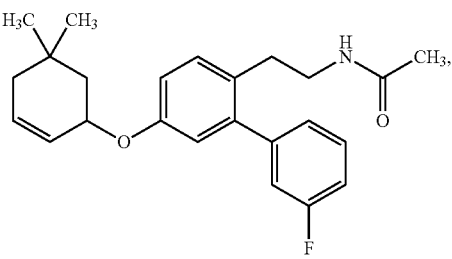
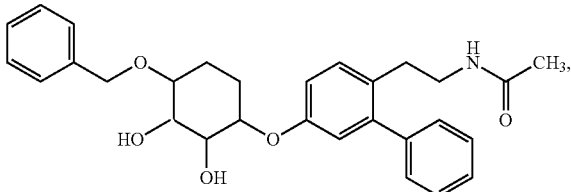
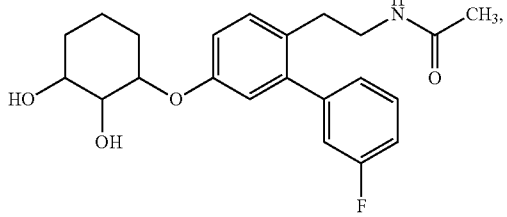
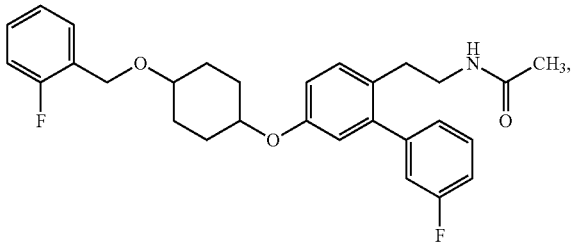
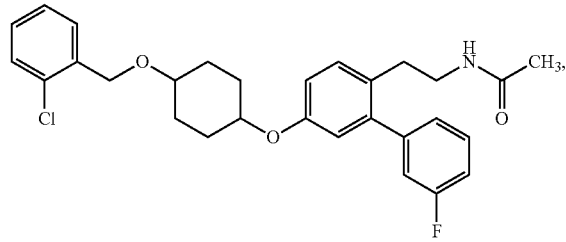
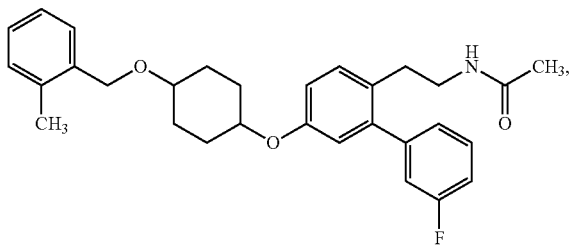

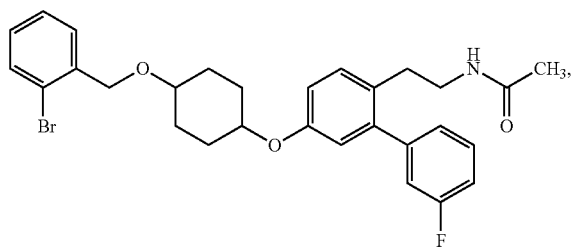
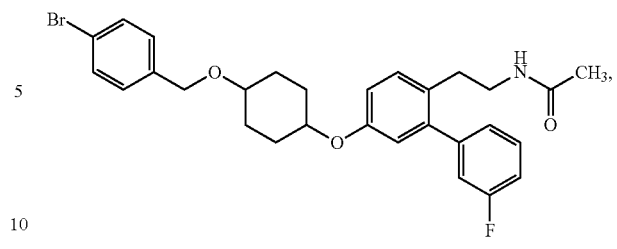
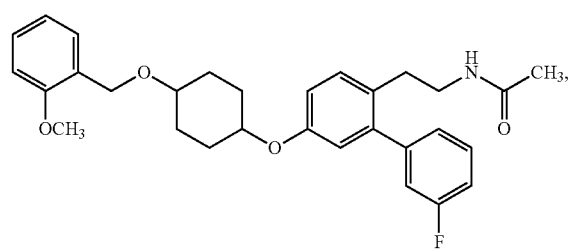
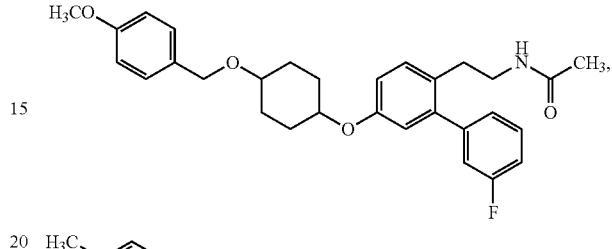
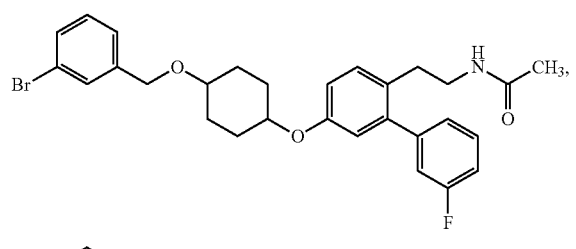
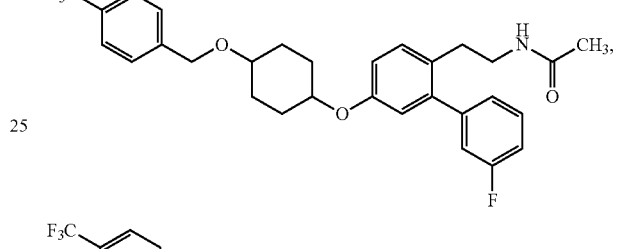
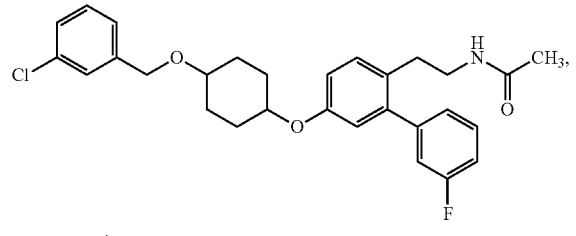
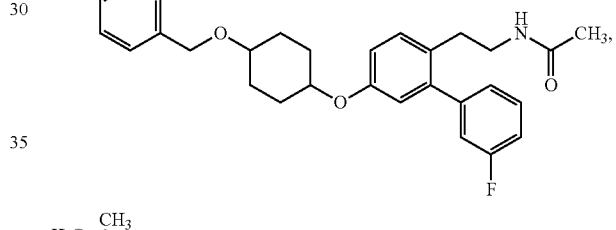
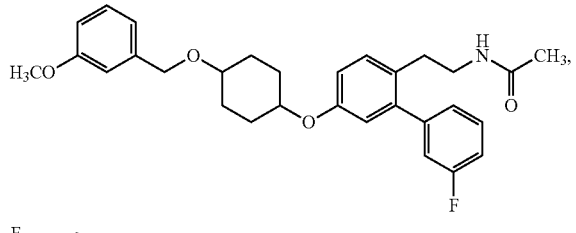
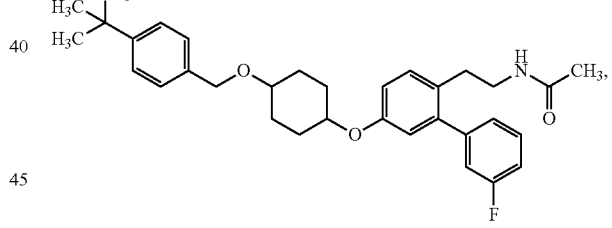
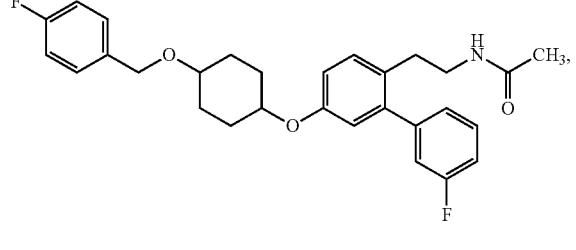
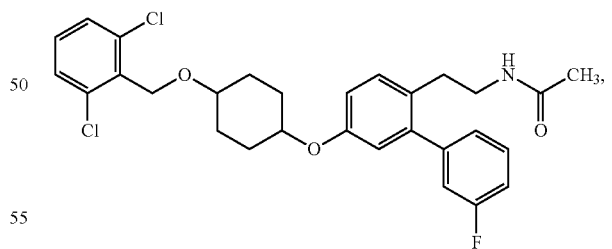
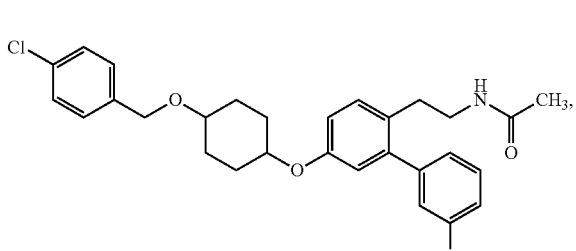
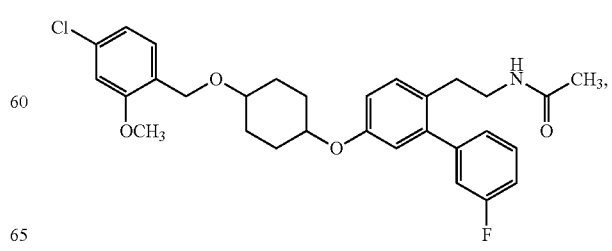

-continued

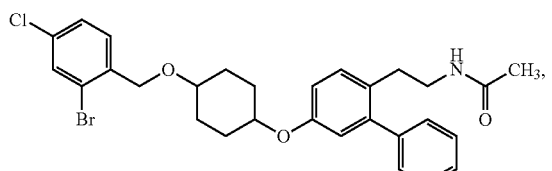

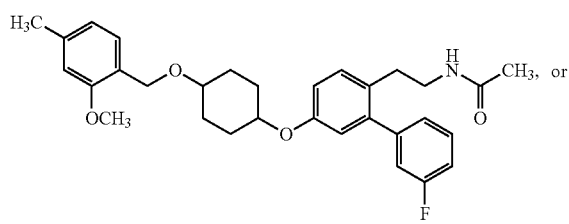

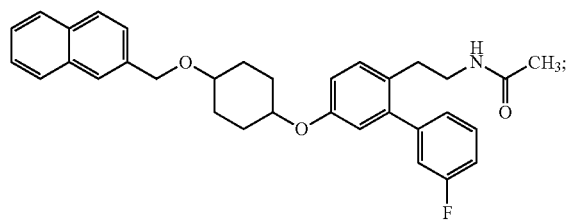

or a pharmaceutically acceptable salt thereof.

In other embodiments, the compounds are further defined as:

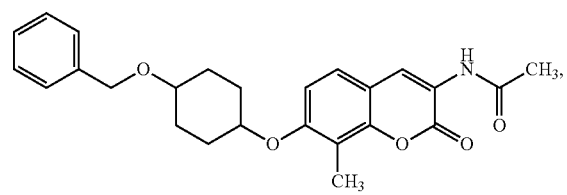

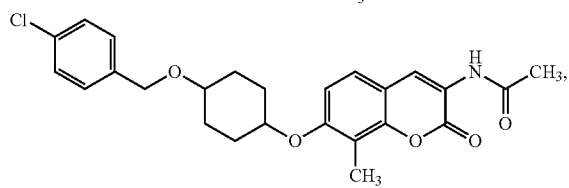

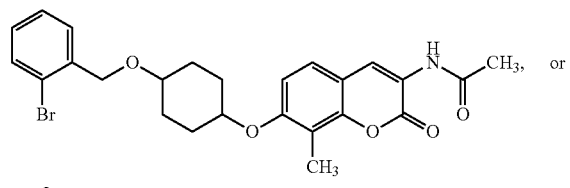

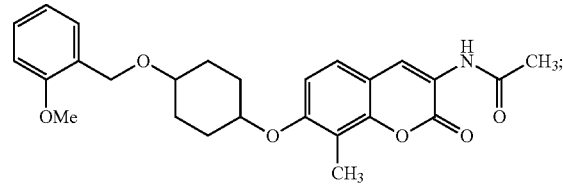

or a pharmaceutically acceptable salt thereof.

In yet another aspect, the present disclosure provides compounds of the formula:

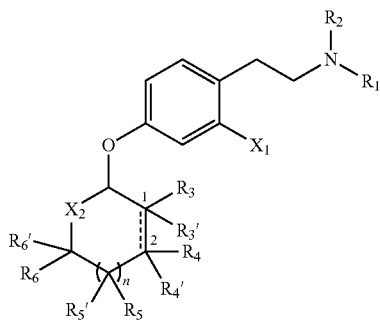

(III)

wherein:
  the bond between atom 1 and atom 2 is either a single bond or a double bond;
  $X_1$ is aryl$_{(C \le 12)}$, heteroaryl$_{(C \le 12)}$, or a substituted version of either of these groups;
  $X_2$ is —CH$_2$— or —O—;
  $R_1$ is acyl$_{(C \le 12)}$ or substituted acyl$_{(C \le 12)}$;
  $R_2$ is hydrogen, alkyl$_{(C \le 12)}$, or substituted alkyl$_{(C \le 12)}$;
  $R_3$, $R_4$, $R_3'$, $R_4'$ are each independently hydrogen, hydroxy, aryloxy$_{(C \le 12)}$, aralkoxy$_{(C \le 12)}$, substituted aryloxy$_{(C \le 12)}$, or substituted aralkoxy$_{(C \le 12)}$;
  each $R_5$ and $R_5'$ are each independently hydrogen, hydroxy, heteroaryloxy$_{(C \le 12)}$, heteroaralkoxy$_{(C \le 12)}$, substituted aryloxy$_{(C \le 12)}$, substituted aralkoxy$_{(C \le 12)}$, substituted heteroaryloxy$_{(C \le 12)}$, or substituted heteroaralkoxy$_{(C \le 12)}$;
  $R_6$ and $R_6'$ are each independently hydrogen, alkyl$_{(C \le 12)}$, cycloalkyl$_{(C \le 12)}$, substituted alkyl$_{(C \le 12)}$, or substituted cycloalkyl$_{(C \le 12)}$; and
  n is 0, 1, or 2; provided that if n is 2 then the $R_5$ and $R_5'$ on each methylene are independently selected;
or a pharmaceutically acceptable salt thereof.

In some embodiments, the compounds are further defined as:

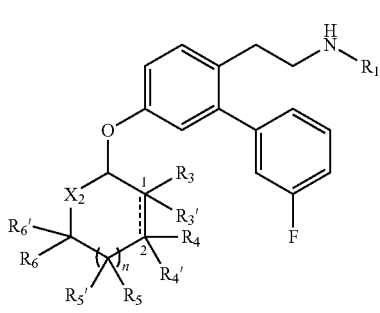

(IV)

wherein:
  the bond between atom 1 and atom 2 is either a single bond or a double bond;
  $X_2$ is —CH$_2$— or —O—;
  $R_1$ is acyl$_{(C \le 12)}$ or substituted acyl$_{(C \le 12)}$;
  $R_3$, $R_4$, $R_3'$, $R_4'$ are each independently hydrogen, hydroxy, aryloxy$_{(C \le 12)}$, aralkoxy$_{(C \le 12)}$, substituted aryloxy$_{(C \le 12)}$, or substituted aralkoxy$_{(C \le 12)}$;
  each $R_5$ and $R_5'$ are each independently hydrogen, hydroxy, heteroaryloxy$_{(C \le 12)}$, heteroaralkoxy$_{(C \le 12)}$, substituted aryloxy$_{(C \le 12)}$, substituted aralkoxy$_{(C \le 12)}$, substituted heteroaryloxy$_{(C \le 12)}$, or substituted heteroaralkoxy$_{(C \le 12)}$;

$R_6$ and $R_6'$ are each independently hydrogen, alkyl$_{(C≤12)}$, cycloalkyl$_{(C≤12)}$, substituted alkyl$_{(C≤12)}$, or substituted cycloalkyl$_{(C≤12)}$; and n is 0, 1, or 2; provided that if n is 2 then the $R_5$ and $R_5'$ on each methylene are independently selected;

or a pharmaceutically acceptable salt thereof.

In some embodiments, the compounds are further defined as:

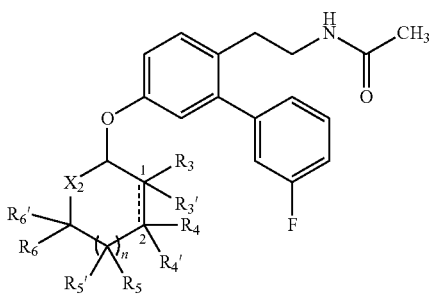

(I)

wherein:
the bond between atom 1 and atom 2 is either a single bond or a double bond;
$X_2$ is —CH$_2$— or —O—;
$R_3$, $R_4$, $R_3'$, $R_4'$ are each independently hydrogen, hydroxy, aryloxy$_{(C≤12)}$, aralkoxy$_{(C≤12)}$, substituted aryloxy$_{(C≤12)}$, or substituted aralkoxy$_{(C≤12)}$;
each $R_5$ and $R_5'$ are each independently hydrogen, hydroxy, heteroaryloxy$_{(C≤12)}$, heteroaralkoxy$_{(C≤12)}$, substituted aryloxy$_{(C≤12)}$, substituted aralkoxy$_{(C≤12)}$, substituted heteroaryloxy$_{(C≤12)}$, or substituted heteroaralkoxy$_{(C≤12)}$;
$R_6$ and $R_6'$ are each independently hydrogen, alkyl$_{(C≤12)}$, cycloalkyl$_{(C≤12)}$, substituted alkyl$_{(C≤12)}$, or substituted cycloalkyl$_{(C≤12)}$; and
n is 0, 1, or 2; provided that if n is 2 then the $R_5$ and $R_5'$ on each methylene are independently selected;

or a pharmaceutically acceptable salt thereof.

In some embodiments, $X_1$ is substituted aryl$_{(C≤12)}$. In some embodiments, $X_1$ is 3-fluorophenyl. In some embodiments, $R_2$ is hydrogen. In some embodiments, $R_1$ is acyl$_{(C≤12)}$. In some embodiments, $R_1$ is acetyl. In some embodiments, the bond between atom 1 and atom 2 is a single bond. In other embodiments, the bond between atom 1 and atom 2 is a double bond.

In some embodiments, $X_2$ is —CH$_2$—. In other embodiments, $X_2$ is —O—. In some embodiments, $R_3$ is hydrogen. In other embodiments, $R_3$ is hydroxy. In some embodiments, $R_3'$ is hydrogen. In other embodiments, $R_3'$ is hydroxy.

In some embodiments, $R_4$ is hydrogen. In other embodiments, $R_4$ is hydroxy. In other embodiments, $R_4$ is aralkoxy$_{(C≤12)}$ or substituted aralkoxy$_{(C≤12)}$. In some embodiments, $R_4$ is benzyloxy. In some embodiments, $R_4'$ is hydrogen. In other embodiments, $R_4'$ is hydroxy. In other embodiments, $R_4'$ is aralkoxy$_{(C≤12)}$ or substituted aralkoxy$_{(C≤12)}$. In some embodiments, $R_4'$ is benzyloxy.

In some embodiments, $R_5$ is hydrogen. In other embodiments, $R_5$ is hydroxy. In other embodiments, $R_5$ is substituted aralkoxy$_{(C≤12)}$. In some embodiments, $R_5$ is 2-fluorophenylmethoxy, 2-bromophenylmethoxy, 2-chlorophenylmethoxy, 2-methoxyphenylmethoxy, 3-bromophenylmethoxy, 3-chlorophenylmethoxy, 3-methoxyphenylmethoxy, 4-fluorophenylmethoxy, 4-chlorophenylmethoxy, 4-bromophenylmethoxy, 4-methoxyphenylmethoxy, 4-trifluoromethylphenylmethoxy, 2,6-dichlorophenylmethoxy, 4-chloro-2-methoxyphenylmethoxy, 2-methoxy-4-methylphenylmethoxy, or 2-bromo-4-chlorophenylmethoxy.

In some embodiments, $R_5'$ is hydrogen. In other embodiments, $R_5'$ is hydroxy. In other embodiments, $R_5'$ is substituted aralkoxy$_{(C≤12)}$. In some embodiments, $R_5'$ is 2-fluorophenylmethoxy, 2-bromophenylmethoxy, 2-chlorophenylmethoxy, 2-methoxyphenylmethoxy, 3-bromophenylmethoxy, 3-chlorophenylmethoxy, 3-methoxyphenylmethoxy, 4-fluorophenylmethoxy, 4-chlorophenylmethoxy, 4-bromophenylmethoxy, 4-methoxyphenylmethoxy, 4-trifluoromethylphenylmethoxy, 2,6-dichlorophenylmethoxy, 4-chloro-2-methoxyphenylmethoxy, 2-methoxy-4-methylphenylmethoxy, or 2-bromo-4-chlorophenylmethoxy.

In some embodiments, $R_6$ is hydrogen. In other embodiments, $R_6$ is alkyl$_{(C≤12)}$ or substituted alkyl$_{(C≤12)}$. In some embodiments, $R_6$ is methyl. In some embodiments, $R_6'$ is hydrogen. In other embodiments, $R_6'$ is alkyl$_{(C≤12)}$ or substituted alkyl$_{(C≤12)}$. In some embodiments, $R_6'$ is methyl. In some embodiments, n is 0. In other embodiments, n is 1.

In some embodiments, the compounds are further defined as:

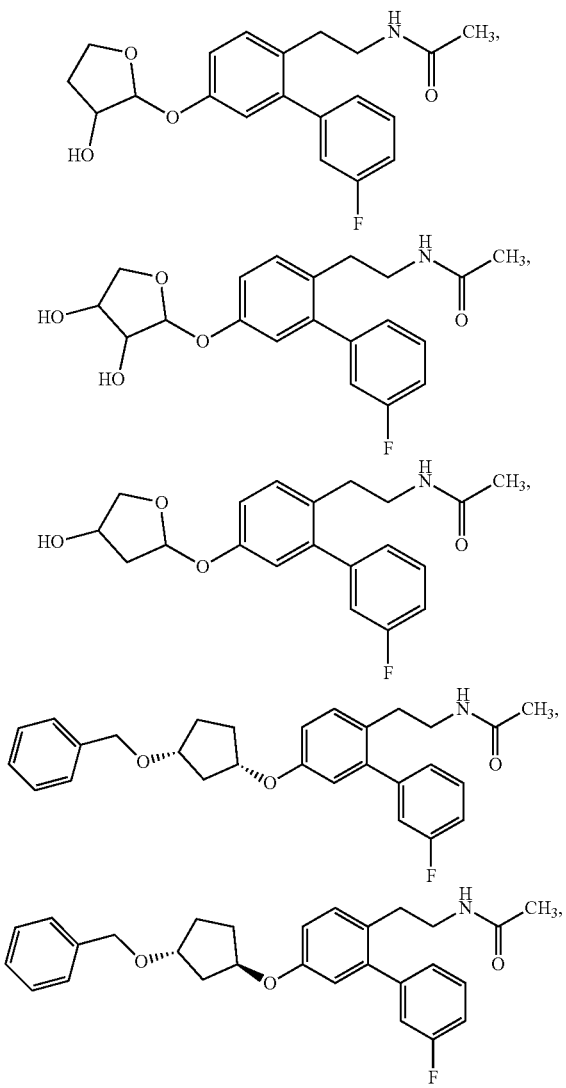

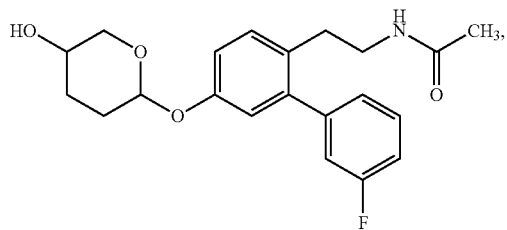
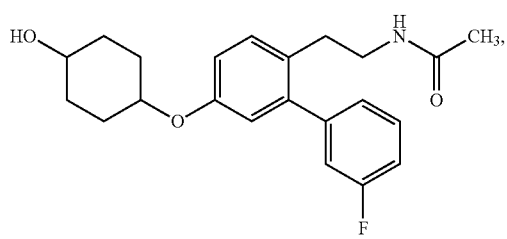
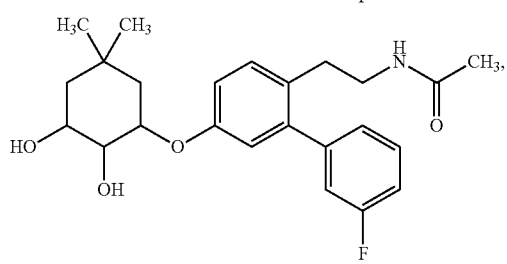
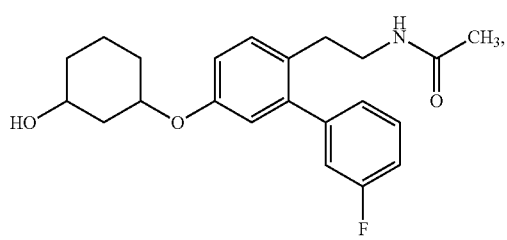
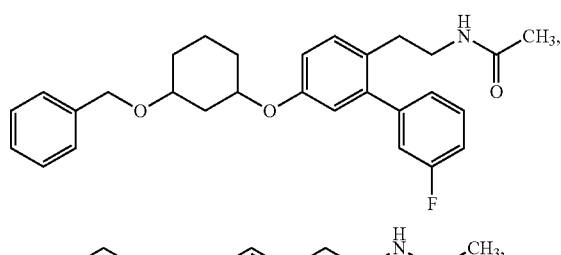
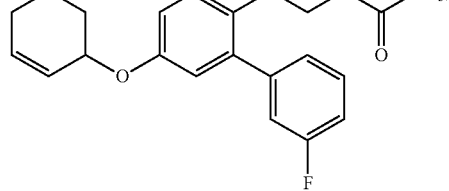
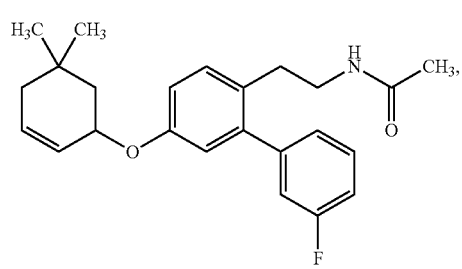
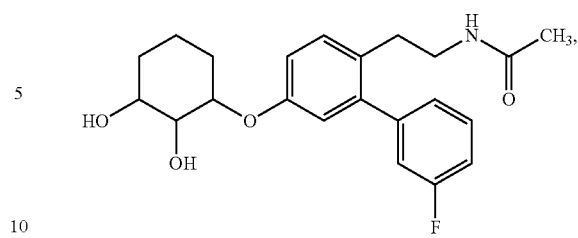
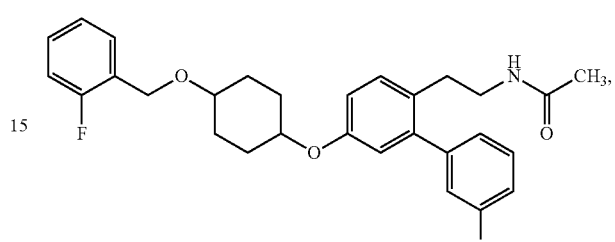
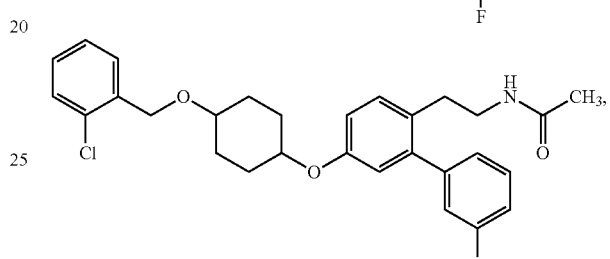
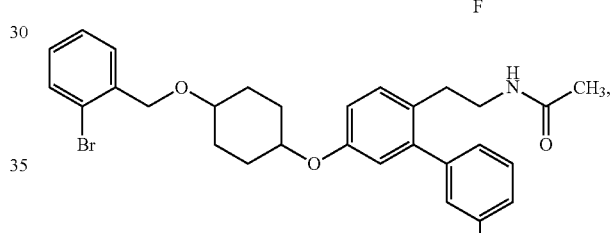
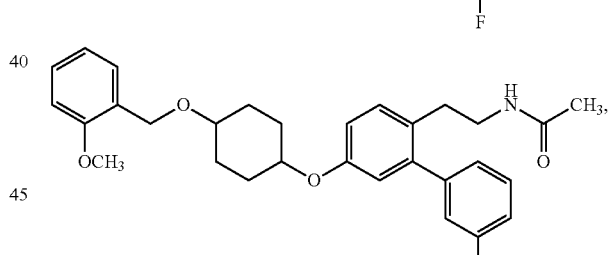
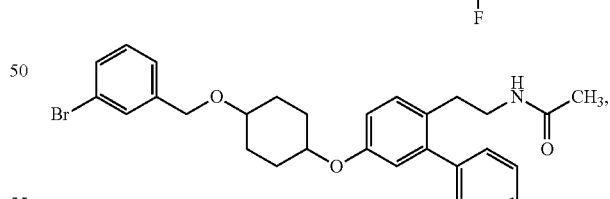
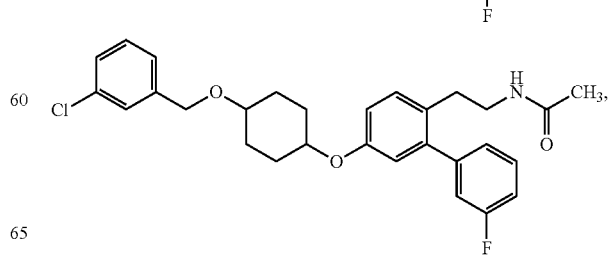

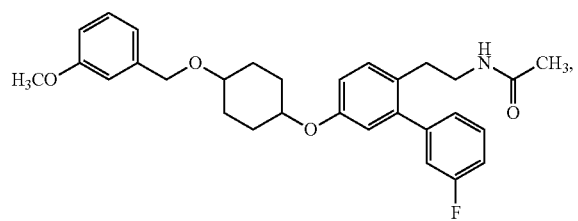
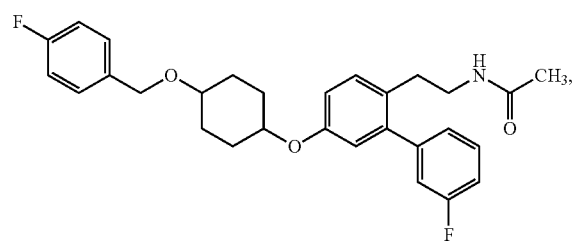
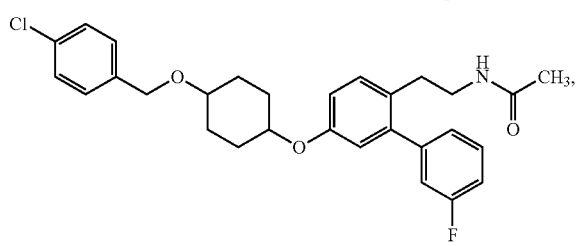
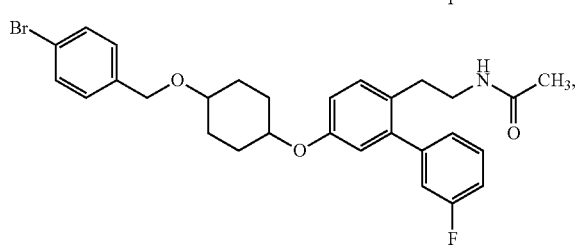
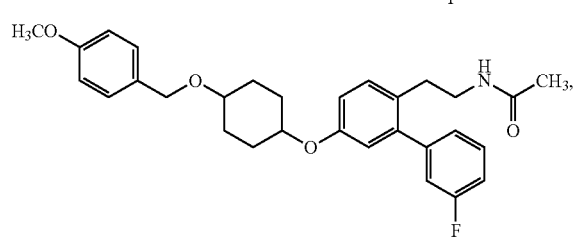
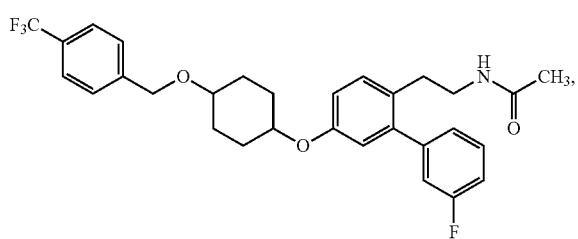
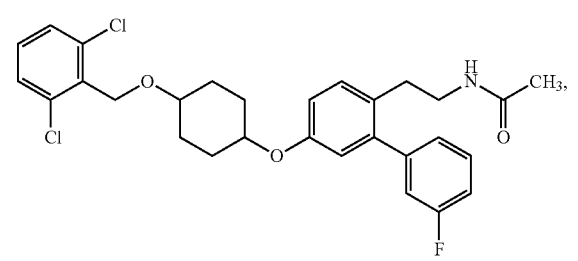
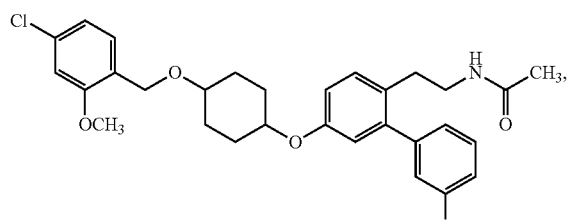
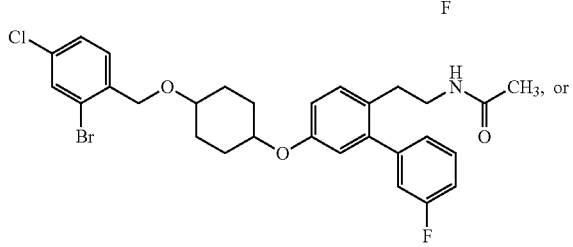
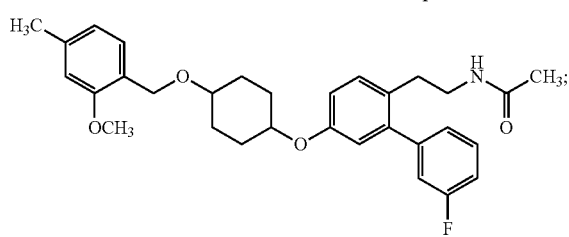
or a pharmaceutically acceptable salt thereof.
In still yet another aspect, the present disclosure provides compounds of the formula:
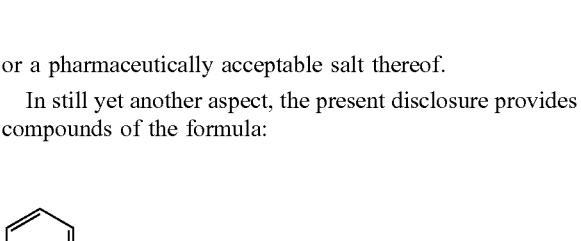
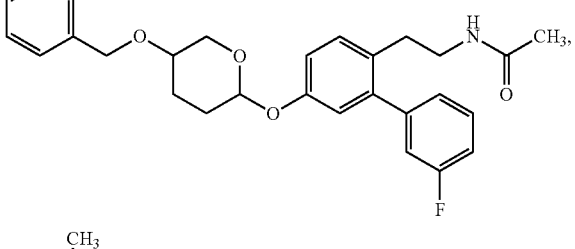
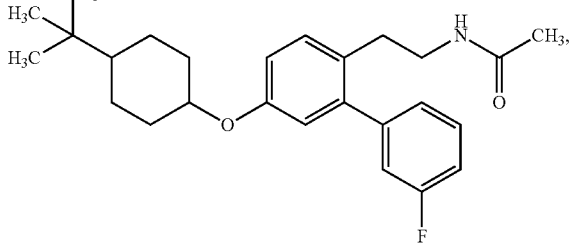
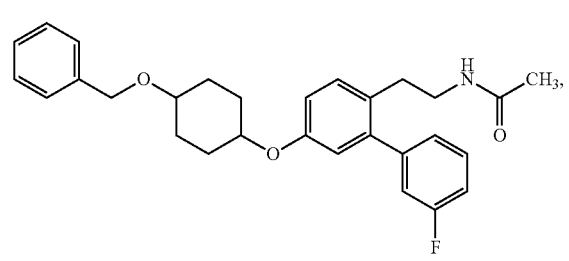

-continued

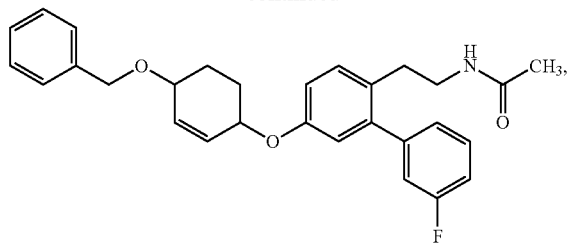

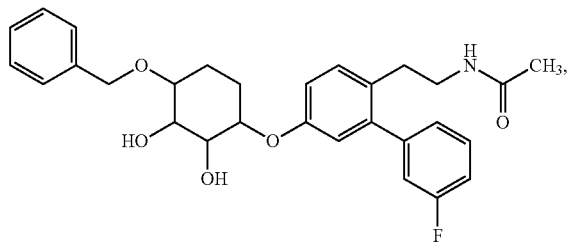

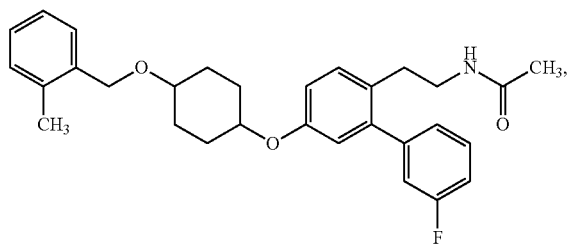

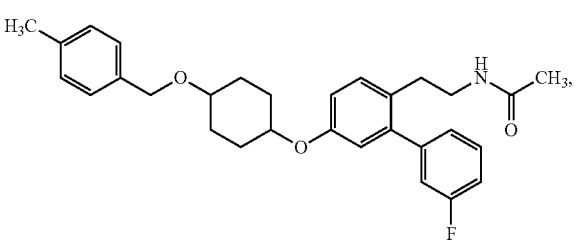

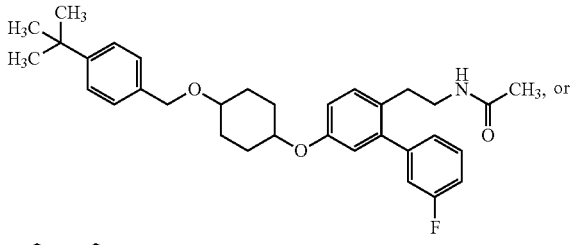

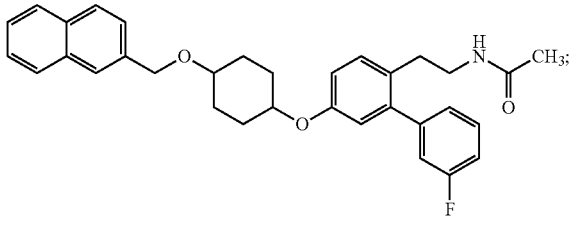

or a pharmaceutically acceptable salt thereof.

In another aspect, the present disclosure provides compounds of the formula:

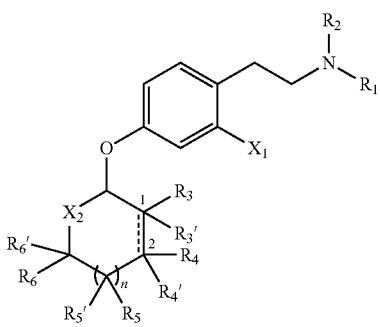

(III)

wherein:
  the bond between atom 1 and atom 2 is either a single bond or a double bond;
  $X_1$ is aryl$_{(C \leq 12)}$, heteroaryl$_{(C \leq 12)}$, or a substituted version of either of these groups;
  $X_2$ is —CH$_2$— or —O—;
  $R_1$ is acyl$_{(C \leq 12)}$ or substituted acyl$_{(C \leq 12)}$;
  $R_2$ is hydrogen, alkyl$_{(C \leq 12)}$, or substituted alkyl$_{(C \leq 12)}$;
  $R_3$, $R_4$, $R_3'$, $R_4'$ are each independently hydrogen, hydroxy, aryloxy$_{(C \leq 12)}$, aralkoxy$_{(C \leq 12)}$, substituted aryloxy$_{(C \leq 12)}$, or substituted aralkoxy$_{(C \leq 12)}$;
  each $R_5$ and $R_5'$ are each independently hydrogen, hydroxy; or a group of the formula:

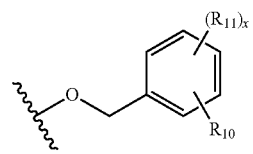

wherein:
  $R_{10}$ and $R_{11}$ are amino, carboxy, cyano, halo, hydroxy, hydroxysulfonyl, or sulfonamide; or
  alkyl$_{(C \leq 8)}$, aryl$_{(C \leq 8)}$, acyl$_{(C \leq 8)}$, alkoxy$_{(C \leq 8)}$, acyloxy$_{(C \leq 8)}$, amido$_{(C \leq 8)}$, alkylamino$_{(C \leq 8)}$, dialkylamino$_{(C \leq 8)}$, or a substituted version of any of these groups; and
  x is 0, 1, 2, 3, or 4;
  $R_6$ and $R_6'$ are each independently hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and
  n is 0, 1, or 2; provided that if n is 2 then the $R_5$ and $R_5'$ on each methylene are independently selected;

or a pharmaceutically acceptable salt thereof.

In some embodiments, the compounds are further defined as:

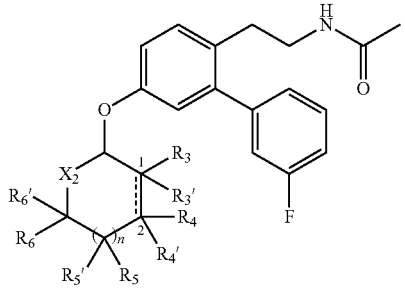

(I)

wherein:
the bond between atom 1 and atom 2 is either a single bond or a double bond;
$X_2$ is —$CH_2$— or —O—;
$R_3$, $R_4$, $R_3'$, $R_4'$ are each independently hydrogen, hydroxy, aryloxy$_{(C≤12)}$, aralkoxy$_{(C≤12)}$, substituted aryloxy$_{(C≤12)}$, or substituted aralkoxy$_{(C≤12)}$;
each $R_5$ and $R_5'$ are each independently hydrogen, hydroxy; or a group of the formula:

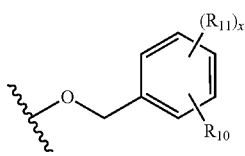

wherein:
$R_{10}$ and $R_{11}$ are amino, carboxy, cyano, halo, hydroxy, hydroxysulfonyl, or sulfonamide; or
alkyl$_{(C≤8)}$, aryl$_{(C≤8)}$, acyl$_{(C≤8)}$, alkoxy$_{(C≤8)}$, acyloxy$_{(C≤8)}$, amido$_{(C≤8)}$, alkylamino$_{(C≤8)}$, dialkylamino$_{(C≤8)}$, or a substituted version of any of these groups; and
x is 0, 1, 2, 3, or 4;
$R_6$ and $R_6'$ are each independently hydrogen, alkyl$_{(C≤12)}$, cycloalkyl$_{(C≤12)}$, substituted alkyl$_{(C≤12)}$, or substituted cycloalkyl$_{(C≤12)}$; and
n is 0, 1, or 2; provided that if n is 2 then the $R_5$ and $R_5'$ on each methylene are independently selected;
or a pharmaceutically acceptable salt thereof.

In some embodiments, the compounds are further defined as:

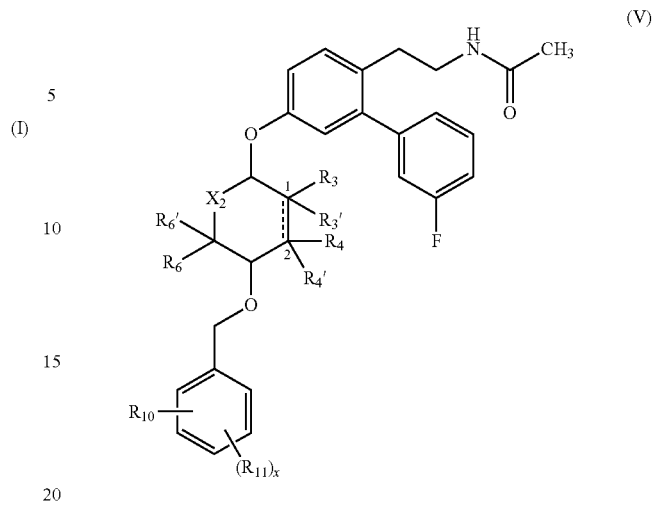

(V)

wherein:
the bond between atom 1 and atom 2 is either a single bond or a double bond;
$X_2$ is —$CH_2$— or —O—;
$R_3$, $R_4$, $R_3'$, $R_4'$ are each independently hydrogen, hydroxy, aryloxy$_{(C≤12)}$, aralkoxy$_{(C≤12)}$, substituted aryloxy$_{(C≤12)}$, or substituted aralkoxy$_{(C≤12)}$;
$R_6$ and $R_6'$ are each independently hydrogen, alkyl$_{(C≤12)}$, cycloalkyl$_{(C≤12)}$, substituted alkyl$_{(C≤12)}$, or substituted cycloalkyl$_{(C≤12)}$; and
$R_{10}$ and $R_{11}$ are amino, carboxy, cyano, halo, hydroxy, hydroxysulfonyl, or sulfonamide; or
alkyl$_{(C≤8)}$, aryl$_{(C≤8)}$, acyl$_{(C≤8)}$, alkoxy$_{(C≤8)}$, acyloxy$_{(C≤8)}$, amido$_{(C≤8)}$, alkylamino$_{(C≤8)}$, dialkylamino$_{(C≤8)}$, or a substituted version of any of these groups; and
x is 0, 1, 2, 3, or 4;
or a pharmaceutically acceptable salt thereof.

In some embodiments, $X_1$ is substituted aryl$_{(C≤12)}$. In some embodiments, $X_1$ is 3-fluorophenyl. In some embodiments, $R_2$ is hydrogen. In some embodiments, $R_1$ is acyl$_{(C≤12)}$. In some embodiments, $R_1$ is acetyl. In some embodiments, the bond between atom 1 and atom 2 is a single bond. In other embodiments, the bond between atom 1 and atom 2 is a double bond.

In some embodiments, $X_2$ is —$CH_2$—. In other embodiments, $X_2$ is —O—. In some embodiments, $R_3$ is hydrogen. In other embodiments, $R_3$ is hydroxy. In some embodiments, $R_3'$ is hydrogen. In other embodiments, $R_3'$ is hydroxy. In some embodiments, $R_4$ is hydrogen. In other embodiments, $R_4$ is hydroxy. In other embodiments, $R_4$ is aralkoxy$_{(C≤12)}$ or substituted aralkoxy$_{(C≤12)}$. In some embodiments, $R_4$ is benzyloxy. In some embodiments, $R_4'$ is hydrogen. In other embodiments, $R_4'$ is hydroxy. In other embodiments, $R_4'$ is aralkoxy$_{(C≤12)}$ or substituted aralkoxy$_{(C≤12)}$. In some embodiments, $R_4'$ is benzyloxy.

In some embodiments, $R_5$ is hydrogen. In other embodiments, $R_5$ is hydroxy. In other embodiments, $R_5$ is:

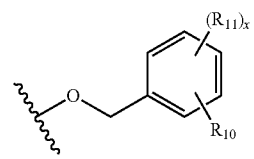

wherein:
R₁₀ and R₁₁ are amino, carboxy, cyano, halo, hydroxy, hydroxysulfonyl, or sulfonamide; or
alkyl$_{(C≤8)}$, aryl$_{(C≤8)}$, acyl$_{(C≤8)}$, alkoxy$_{(C≤8)}$, acyloxy$_{(C≤8)}$, amido$_{(C≤8)}$, alkylamino$_{(C≤8)}$, dialkylamino$_{(C≤8)}$, or a substituted version of any of these groups; and
x is 0, 1, 2, 3, or 4.

In some embodiments, R₁₀ is halo. In some embodiments, R₁₀ is fluoro, chloro, or bromo. In other embodiments, R₁₀ is alkyl(c s) or substituted alkyl$_{(C≤8)}$. In some embodiments, R₁₀ is alkyl$_{(C≤8)}$. In other embodiments, R₁₀ is methyl. In other embodiments, R₁₀ is substituted alkyl$_{(C≤8)}$. In some embodiments, R₁₀ is trifluoromethyl. In other embodiments, R₁₀ is alkoxy$_{(C≤8)}$ or substituted alkoxy$_{(C≤8)}$. In some embodiments, R₁₀ is alkoxy$_{(C≤8)}$. In some embodiments, R₁₀ is methoxy. In some embodiments, R₁₁ is halo. In some embodiments, R₁₁ is fluoro, chloro, or bromo. In other embodiments, R₁₁ is alkyl(c s) or substituted alkyl$_{(C≤8)}$. In some embodiments, R₁₁ is alkyl$_{(C≤8)}$. In some embodiments, R₁₁ is methyl. In other embodiments, R₁₁ is substituted alkyl$_{(C≤8)}$. In some embodiments, R₁₁ is trifluoromethyl. In other embodiments, R₁₁ is alkoxy$_{(C≤8)}$ or substituted alkoxy$_{(C≤8)}$. In some embodiments, R₁₁ is alkoxy$_{(C≤8)}$. In some embodiments, R₁₁ is methoxy. In some embodiments, x is 0, 1, or 2. In some embodiments, x is 0. In other embodiments, x is 1.

In some embodiments, R₅' is hydrogen. In other embodiments, R₅' is hydroxy. In other embodiments, R₅' is:

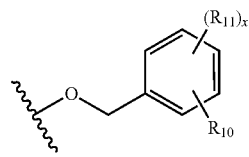

wherein:
R₁₀ and R₁₁ are amino, carboxy, cyano, halo, hydroxy, hydroxysulfonyl, or sulfonamide; or
alkyl$_{(C≤8)}$, aryl$_{(C≤8)}$, acyl$_{(C≤8)}$, alkoxy$_{(C≤8)}$, acyloxy$_{(C≤8)}$, amido$_{(C≤8)}$, alkylamino$_{(C≤8)}$, dialkylamino$_{(C≤8)}$, or a substituted version of any of these groups; and
x is 0, 1, 2, 3, or 4.

In some embodiments, R₁₀ is halo. In some embodiments, R₁₀ is fluoro, chloro, or bromo. In other embodiments, R₁₀ is alkyl$_{(C≤8)}$ or substituted alkyl$_{(C≤8)}$. In some embodiments, R₁₀ is alkyl$_{(C≤8)}$. In other embodiments, R₁₀ is methyl. In other embodiments, R₁₀ is substituted alkyl$_{(C≤8)}$. In some embodiments, R₁₀ is trifluoromethyl. In other embodiments, R₁₀ is alkoxy$_{(C≤8)}$ or substituted alkoxy$_{(C≤8)}$. In some embodiments, R₁₀ is alkoxy$_{(C≤8)}$. In some embodiments, R₁₀ is methoxy. In some embodiments, R₁₁ is halo. In some embodiments, R₁₁ is fluoro, chloro, or bromo. In other embodiments, R₁₁ is alkyl$_{(C≤8)}$ or substituted alkyl$_{(C≤8)}$. In some embodiments, R₁₁ is alkyl$_{(C≤8)}$. In some embodiments, R₁₁ is methyl. In other embodiments, R₁₁ is substituted alkyl$_{(C≤8)}$. In some embodiments, R₁₁ is trifluoromethyl. In other embodiments, R₁₁ is alkoxy$_{(C≤8)}$ or substituted alkoxy$_{(C≤8)}$. In some embodiments, R₁₁ is alkoxy$_{(C≤8)}$. In some embodiments, R₁₁ is methoxy. In some embodiments, x is 0, 1, or 2. In some embodiments, x is 0. In other embodiments, x is 1.

In some embodiments, R₆ is hydrogen. In other embodiments, R₆ is alkyl$_{(C≤12)}$ or substituted alkyl$_{(C≤12)}$. In some embodiments, R₆ is methyl. In some embodiments, R₆' is hydrogen. In other embodiments, R₆' is alkyl$_{(C≤12)}$ or substituted alkyl$_{(C≤12)}$. In some embodiments, R₆' is methyl. In some embodiments, n is 0. In other embodiments, n is 1.

In some embodiments, the compounds are further defined as:

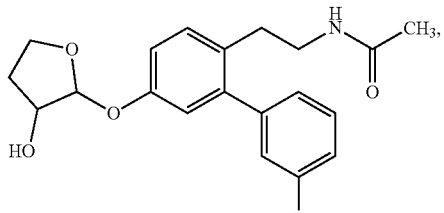

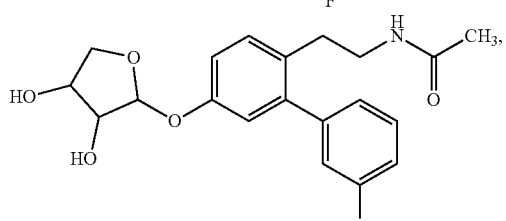

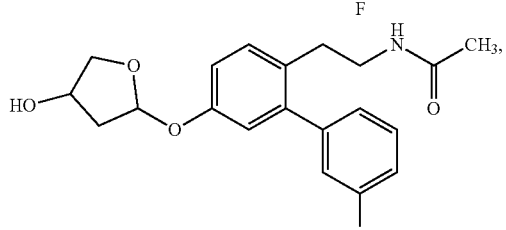

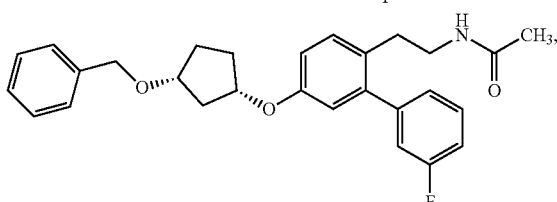

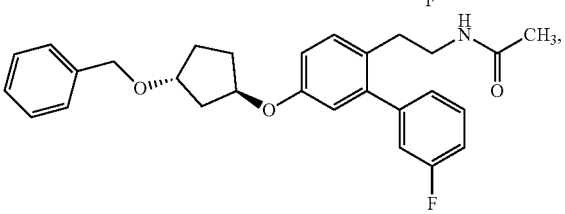

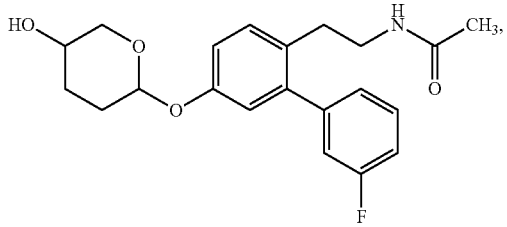

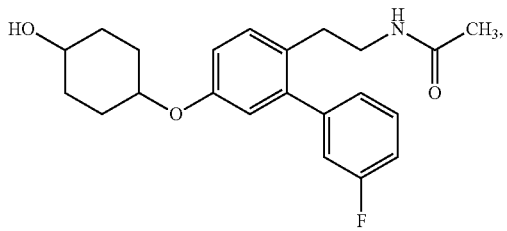

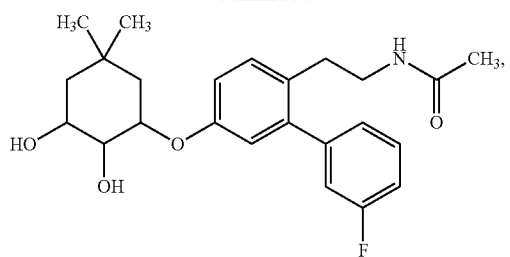
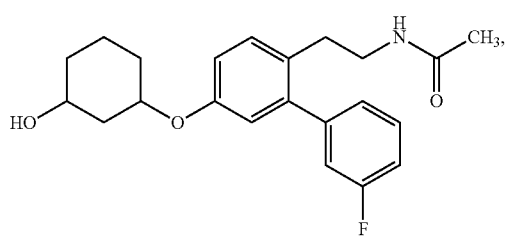
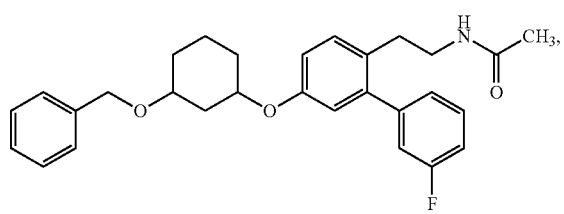
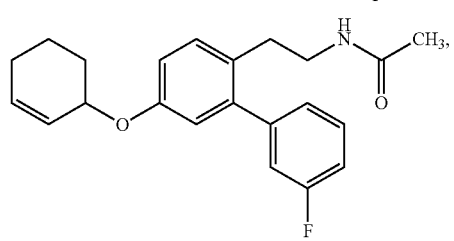
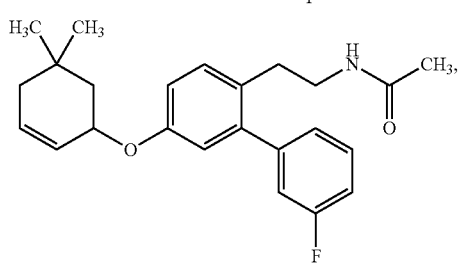
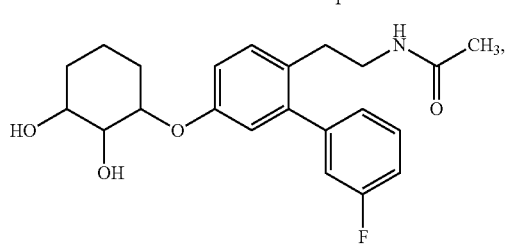
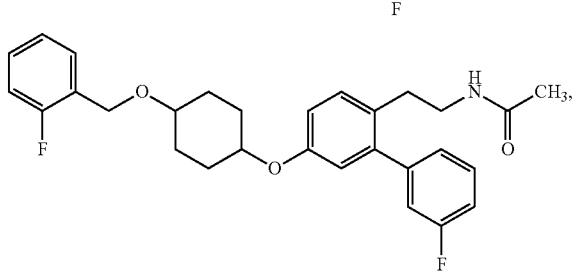
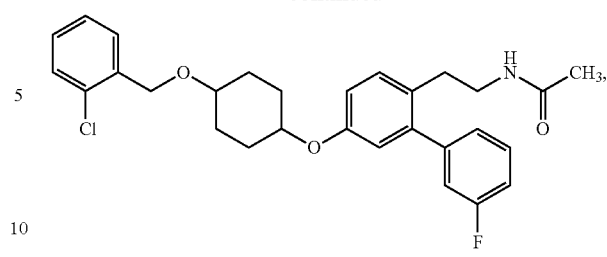
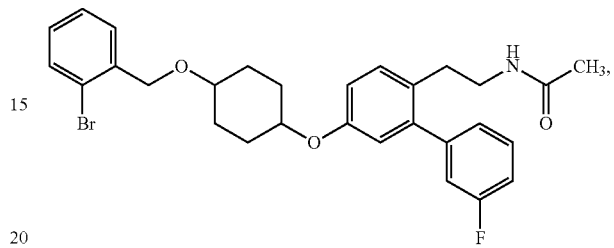
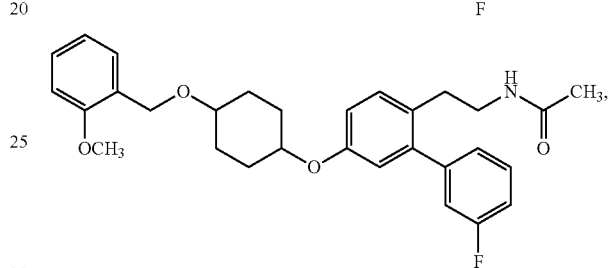
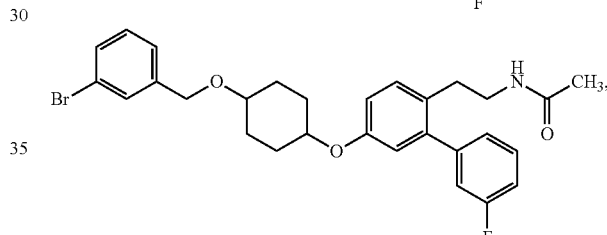
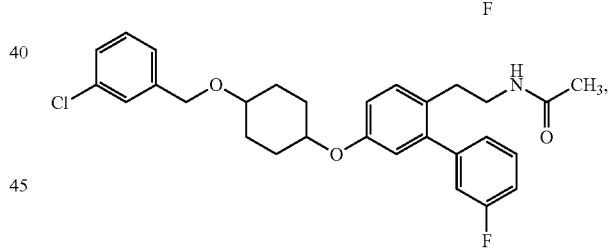
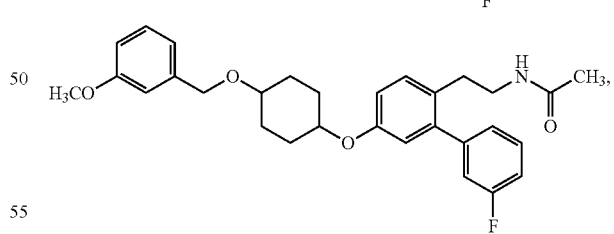
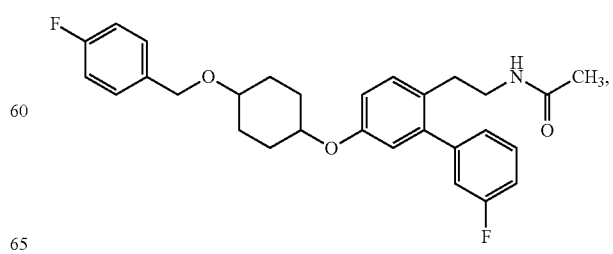

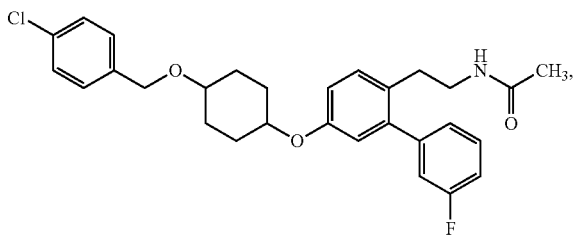

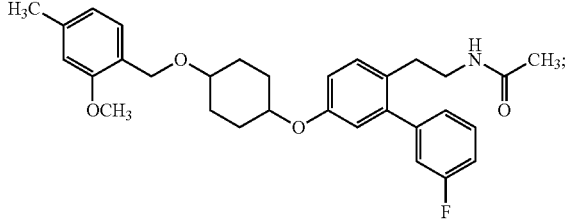

or a pharmaceutically acceptable salt thereof.

In still yet another aspect, the present disclosure provides pharmaceutical compositions comprising:

(A) a compound of the present disclosure; and
(B) a pharmaceutically acceptable carrier.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical compositions are formulated for oral, intraarterial, or intravenous administration. In some embodiments, the pharmaceutical compositions are formulated as a unit dose.

In another aspect, the present disclosure provides methods of treating a disease or disorder in a patient comprising administering to the patient in need thereof a therapeutically effective amount of a compound or composition of the present disclosure. In some embodiments, the disease or disorder is a neurological disorder. In other embodiments, the disease or disorder is diabetes or a complication thereof. In some embodiments, the disease or disorder is a complication from diabetes. In some embodiments, the complication from diabetes is neuropathy, nephropathy, retinopathy, or vasculopathy. In some embodiments, the complication from diabetes is neuropathy. In some embodiments, the disease or disorder is diabetic peripheral neuropathy. In other embodiments, the disease or disorder is cancer.

In some embodiments, the disease or disorder is associated with misregulation of the Hsp70 protein. In some embodiments, the disease or disorder is associated with misregulation of the Hsp90 protein. In some embodiments, the patient is a mammal. In some embodiments, the patient is human. In some embodiments, the compound is administered once to the patient. In other embodiments, the compound is administered two or more times to the patient.

In yet another aspect, the present disclosure provides methods of inducing expression of a Hsp70 protein comprising contacting the protein with an effective amount of a compound or composition of the present disclosure sufficient to induce the expression of the Hsp70 protein. In some embodiments, the protein is contacted in vitro. In other embodiments, the protein is contacted in vivo. In some embodiments, the effective amount of a compound or composition is effective enough to induce expression by at least 50% of the Hsp70 protein. In some embodiments, the Hsp70 protein expression is induced by more than 100%. In some embodiments, the induction of Hsp70 protein expression is sufficient to treat a disease or disorder. In some embodiments, the disease or disorder is a neurodegenerative disease. In some embodiments, the neurodegenerative disease is associated with misfolded proteins, demyelination, inflammation, and neuropathy. In some embodiments, the neurodegenerative disease is diabetic peripheral neuropathy. In some embodiments, the induction of Hsp70 protein expression results in a modulation in expression of one or more downstream products. In other embodiments, the induction of Hsp70 protein expression results in a modulation in activity of one or more downstream products.

In still yet another aspect, the present disclosure provides methods of inhibiting of a Hsp90 protein comprising contacting the protein with an effective amount of a compound or composition of the present disclosure sufficient to inhibit the activity of the Hsp90 protein. In some embodiments, the protein is contacted in vitro. In other embodiments, the protein is contacted in vivo. In some embodiments, the effective amount of a compound or composition is effective enough to inhibit the expression of the Hsp90 protein by at least 50%. In some embodiments, the Hsp90 protein expression is inhibited by more than 75%. In some embodiments, the inhibition of Hsp90 protein expression is sufficient to treat a disease or disorder. In some embodiments, the disease or disorder is cancer or a hyperproliferative disorder. In other embodiments, the disease or disorder is associated with a highly proliferating cell. In some embodiments, the inhibition of Hsp90 protein expression results in a modulation in expression of one or more downstream products. In other embodiments, the inhibition of Hsp90 protein expression results in a modulation in activity of one or more downstream products.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 3A shows a representative gel from the immunoblot analysis. In the immunoblot analysis, 50B11 cells were treated for 24 hr with 1 µM of the indicated analogs or 250 nM geldanamycin (GDA) as a positive control. FIG. 3B shows densitometric quantitation of Hsp70 expression from three experiments. Results are mean±standard error of the mean (SEM) (n=6). Consistent with the induction of luciferase activity via the Hsp70 promoter, 44 also induced Hsp70 protein expression. Compound 59 was less effective despite the robust induction of luciferase activity but addition of a cis diol to the cylohexyl ring (75) increased Hsp70 protein expression. The remaining para-substituted and ortho-substituted compounds were similarly effective.

DESCRIPTION OF ILLUSTRATIVE EMBODIMENTS

Figure 1:
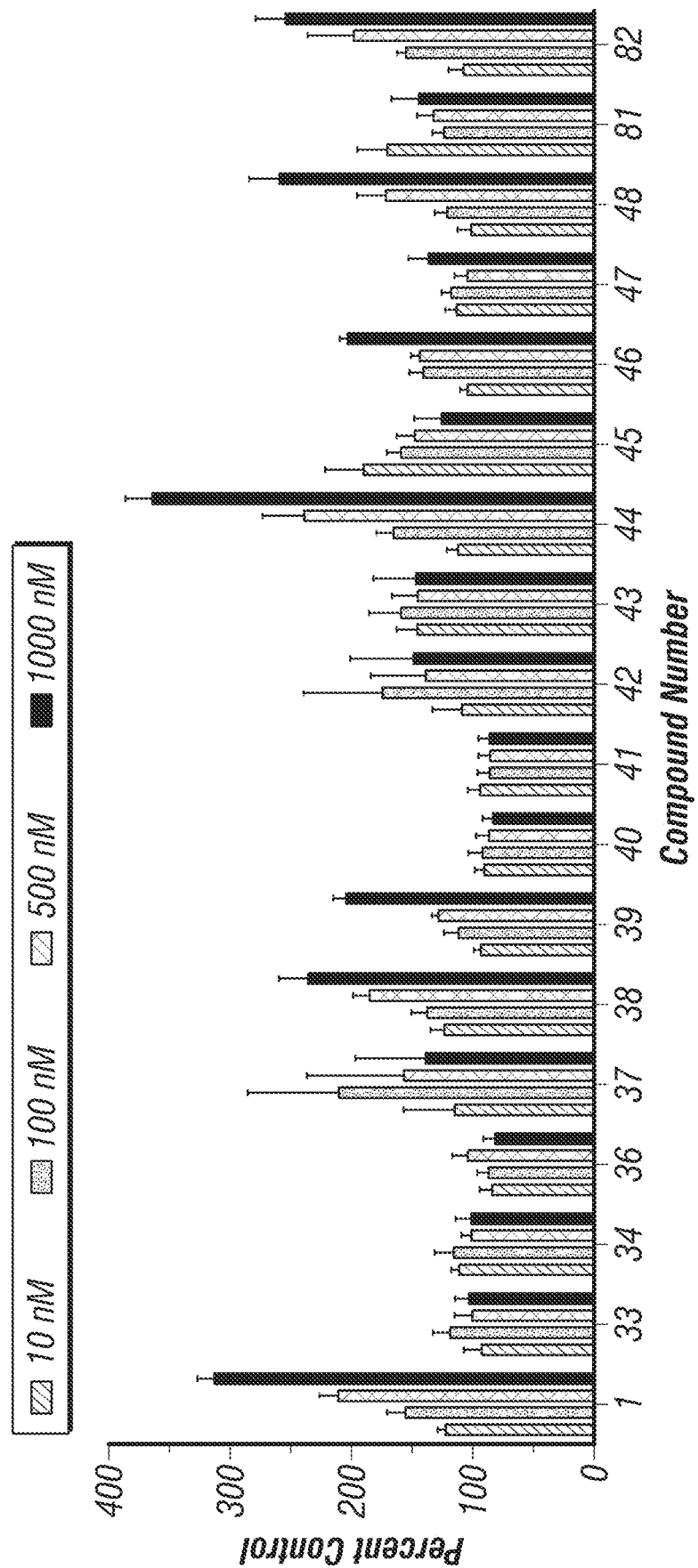
FIG. 1 shows the results of a luciferase assay assessing Hsp70 induction by compounds 33-48 and 81-82 compared with KU-596 (1, positive control) and DMSO (negative control) wherein the induction of the negative control is assigned a value of 100. Results are given as mean±standard error of the mean (SEM) (n=3-9) for four compound concentrations: 10 nM, 100 nM, 500 nM, and 1,000 nM. Compound 44 induces the highest level of Hsp70 expression at both the 500 nM and 1,000 nM.

The present disclosure provides ether modified biphenyl amide and coumarin Hsp70 inducers, including novobiocin analogs with anti-proliferative properties, pharmaceutical compositions thereof, methods for their manufacture, and methods for their use. In some embodiments, the compounds provided herein may also be used as inhibitors of the c-terminus of the Hsp90 protein. The Hsp90 protein is associated with a variety of different target cellular processes that are misregulated in proliferative diseases, as well as other disorders. As such the compounds provided herein may also be used to treat neurological disorders and complications from diabetes such as diabetic peripheral neuropathy.

I. Compounds and Synthetic Methods

In some aspects, the present disclosure provides compounds of the formula:

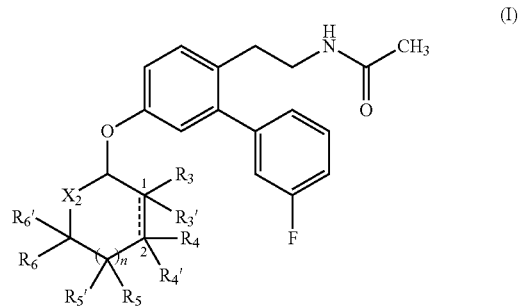

wherein:
   the bond between atom 1 and atom 2 is either a single bond or a double bond;
   $X_2$ is —CH$_2$— or —O—;
   $R_3$, $R_4$, $R_3'$, $R_4'$ are each independently hydrogen, hydroxy, alkoxy$_{(C\leq 8)}$, aryloxy$_{(C\leq 8)}$, aralkoxy$_{(C\leq 8)}$, substituted alkoxy$_{(C\leq 8)}$, substituted aryloxy$_{(C\leq 8)}$, or substituted aralkoxy$_{(C\leq 8)}$;
   each $R_5$ and $R_5'$ are each independently hydrogen, hydroxy, alkyl$_{(C\leq 8)}$, aryloxy$_{(C\leq 8)}$, aralkoxy$_{(C\leq 8)}$, substituted alkyl$_{(C\leq 8)}$, substituted aryloxy$_{(C\leq 8)}$, or substituted aralkoxy$_{(C\leq 8)}$;
   $R_6$ and $R_6'$ are each independently hydrogen, alkyl$_{(C\leq 8)}$, or substituted alkyl$_{(C\leq 8)}$; and
   n is 0, 1, or 2; provided that if n is 2, then each $R_5$ and $R_5'$ on each methylene are independently selected;
or a pharmaceutically acceptable salt thereof.

In another aspect, the present disclosure provides compounds of the formula:

(II)

wherein:
   $R_7$ is aryl$_{(C\leq 12)}$, aralkyl$_{(C\leq 12)}$, or a substituted version of either of these groups;
   $R_8$ is hydrogen, alkyl$_{(C\leq 12)}$, cycloalkyl$_{(C\leq 12)}$, substituted alkyl$_{(C\leq 12)}$, or substituted cycloalkyl$_{(C\leq 12)}$;
   $R_9$ is alkyl$_{(C\leq 12)}$, cycloalkyl$_{(C\leq 12)}$, aryl$_{(C\leq 12)}$, heteroaryl$_{(C\leq 12)}$, or a substituted version of any of these groups; and
   $Y_1$ and $Y_2$ are each independently hydrogen or hydroxy;
or a pharmaceutically acceptable salt thereof.

In still another aspect, the present disclosure provides compounds of the formula:

(III)

wherein:
   the bond between atom 1 and atom 2 is either a single bond or a double bond;
   $X_1$ is aryl$_{(C\leq 12)}$, heteroaryl$_{(C\leq 12)}$, or a substituted version of either of these groups;
   $X_2$ is —CH$_2$— or —O—;
   $R_1$ is acyl$_{(C\leq 12)}$ or substituted acyl$_{(C\leq 12)}$;
   $R_2$ is hydrogen, alkyl$_{(C\leq 12)}$, or substituted alkyl$_{(C\leq 12)}$;
   $R_3$, $R_4$, $R_3'$, $R_4'$ are each independently hydrogen, hydroxy, aryloxy$_{(C\leq 12)}$, aralkoxy$_{(C\leq 12)}$, substituted aryloxy$_{(C\leq 12)}$, or substituted aralkoxy$_{(C\leq 12)}$;
   each $R_5$ and $R_5'$ are each independently hydrogen, hydroxy, substituted aryloxy$_{(C\leq 12)}$, or substituted aralkoxy$_{(C\leq 12)}$;
   $R_6$ and $R_6'$ are each independently hydrogen, alkyl$_{(C\leq 12)}$, or substituted alkyl$_{(C\leq 12)}$; and
   n is 0, 1, or 2; provided that if n is 2 then the $R_5$ and $R_5'$ on each methylene are independently selected;
or a pharmaceutically acceptable salt thereof.

In still yet another aspect, the present disclosure provides compounds of the formula:

(III)

wherein:
   the bond between atom 1 and atom 2 is either a single bond or a double bond;
   $X_1$ is aryl$_{(C\leq 12)}$, heteroaryl$_{(C\leq 12)}$, or a substituted version of either of these groups;
   $X_2$ is —CH$_2$— or —O—;
   $R_1$ is acyl$_{(C\leq 12)}$ or substituted acyl$_{(C\leq 12)}$;
   $R_2$ is hydrogen, alkyl$_{(C\leq 12)}$, or substituted alkyl$_{(C\leq 12)}$;
   $R_3$, $R_4$, $R_3'$, $R_4'$ are each independently hydrogen, hydroxy, aryloxy$_{(C\leq 12)}$, aralkoxy$_{(C\leq 12)}$, substituted aryloxy$_{(C\leq 12)}$, or substituted aralkoxy$_{(C\leq 12)}$;
   each $R_5$ and $R_5'$ are each independently hydrogen, hydroxy; or a group of the formula:

wherein:
   $R_{10}$ and $R_{11}$ are amino, carboxy, cyano, halo, hydroxy, hydroxysulfonyl, or sulfonamide; or
   alkyl$_{(C\leq 8)}$, aryl$_{(C\leq 8)}$, acyl$_{(C\leq 8)}$, alkoxy$_{(C\leq 8)}$, acyloxy$_{(C\leq 8)}$, amido$_{(C\leq 8)}$, alkylamino$_{(C\leq 8)}$, dialkylamino$_{(C\leq 8)}$, or a substituted version of any of these groups; and
   x is 0, 1, 2, 3, or 4;
   $R_6$ and $R_6'$ are each independently hydrogen, alkyl$_{(C\leq 12)}$, or substituted alkyl$_{(C\leq 12)}$; and n is 0, 1, or 2; provided that if n is 2 then the $R_5$ and $R_5'$ on each methylene are independently selected;

or a pharmaceutically acceptable salt thereof.

Additionally, in still yet another aspect, the present disclosure provides compounds comprising a structure of Formula 6 or Formula 7 or Formula 8, derivative thereof, prodrug thereof, salt thereof, or stereoisomer thereof, or having any chirality at any chiral center, or tautomer, polymorph, solvate, or combination thereof:

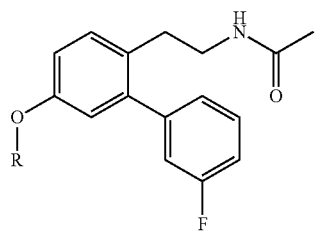

Formula 6

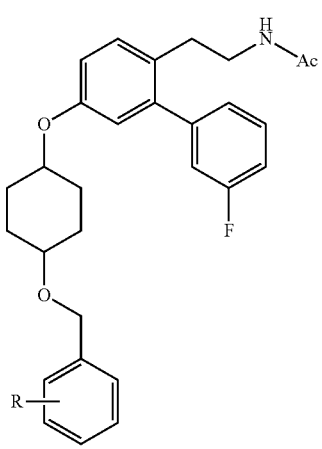

49-68

Formula 7

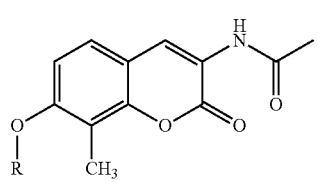

Formula 8 wherein R is any substituent. In other aspects, the substituent is selected from substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N═N$^+$═N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—NO$_2$), nitroso (—NO), sulfo (—SO$_2$—OH), sulfonato (—S$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), derivatives thereof, and combinations thereof.

The compounds provided by the present disclosure are shown, for example, above in the summary of the invention section, the preceding paragraphs, in the claims below, and in the formulas provided in Table 1 below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

TABLE 1

Examples of Biphenyl and Coumarin Compounds Provided Herein

| Compound Number | Structure |
|---|---|
| 33 | 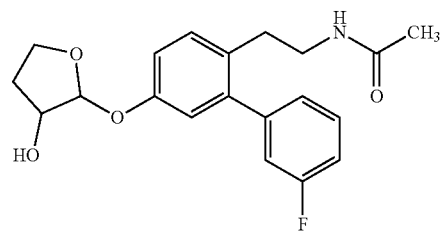 [SMILES: CC(=O)NCCc1ccc(OC2OCCC2O)cc1-c1cccc(F)c1] |

TABLE 1-continued
Examples of Biphenyl and Coumarin Compounds Provided Herein
| Compound Number | Structure |
| --- | --- |
| 34 | 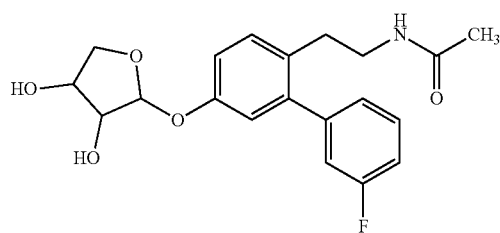 [SMILES: CC(=O)NCCc1ccc(OC2OCC(O)C2O)cc1-c1cccc(F)c1] |
| 35 | 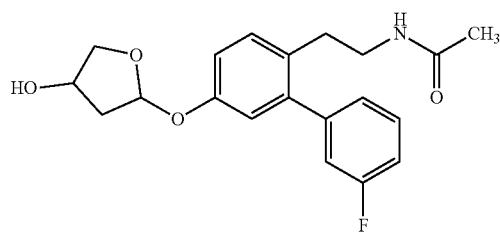 [SMILES: CC(=O)NCCc1ccc(OC2CC(O)CO2)cc1-c1cccc(F)c1] |
| 40 | 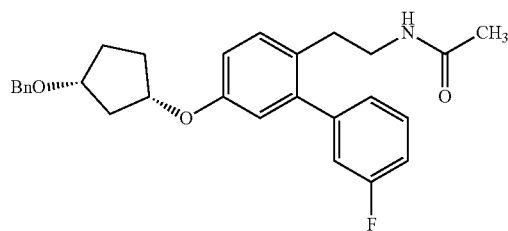 [SMILES: CC(=O)NCCc1ccc(O[C@H]2CC[C@@H](OCc3ccccc3)C2)cc1-c1cccc(F)c1] |
| 41 | 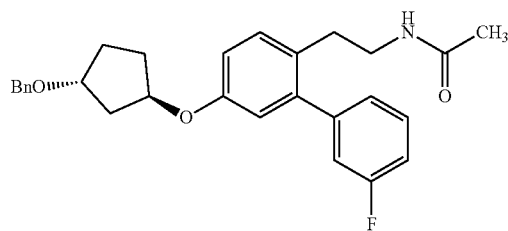 [SMILES: CC(=O)NCCc1ccc(O[C@@H]2CC[C@@H](OCc3ccccc3)C2)cc1-c1cccc(F)c1] |
| 36 | 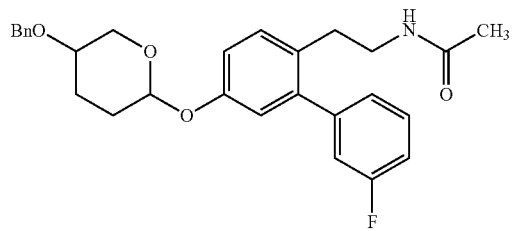 [SMILES: CC(=O)NCCc1ccc(OC2CCC(OCc3ccccc3)CO2)cc1-c1cccc(F)c1] |
| 47 | 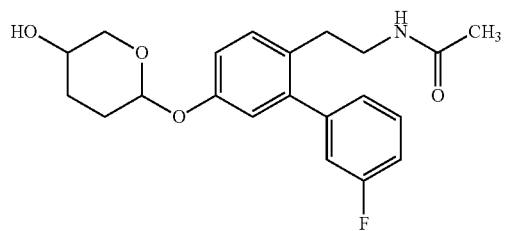 [SMILES: CC(=O)NCCc1ccc(OC2CCC(O)CO2)cc1-c1cccc(F)c1] |

TABLE 1-continued
Examples of Biphenyl and Coumarin Compounds Provided Herein
| Compound Number | Structure |
| --- | --- |
| 42 | 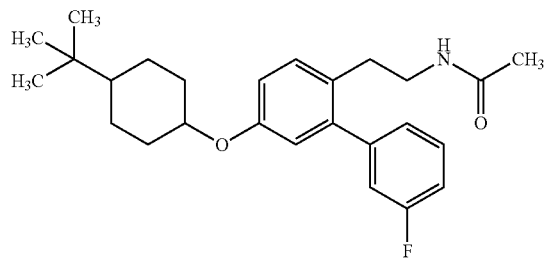 [SMILES: CC(=O)NCCc1ccc(OC2CCC(C(C)(C)C)CC2)cc1-c1cccc(F)c1] |
| 48 | 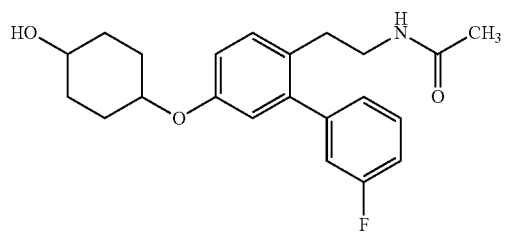 [SMILES: CC(=O)NCCc1ccc(OC2CCC(O)CC2)cc1-c1cccc(F)c1] |
| 81 | 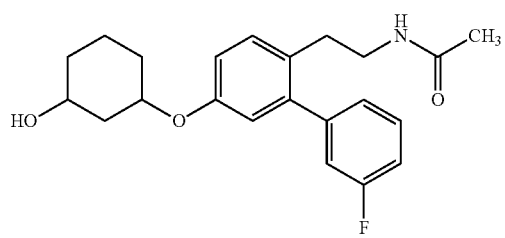 [SMILES: CC(=O)NCCc1ccc(OC2CCCC(O)C2)cc1-c1cccc(F)c1] |
| 44 | 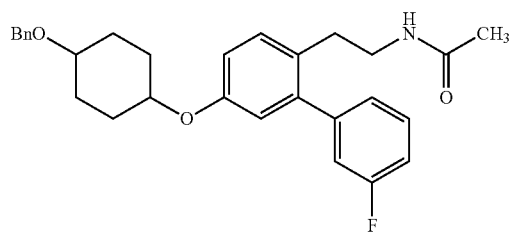 |
| 43 | 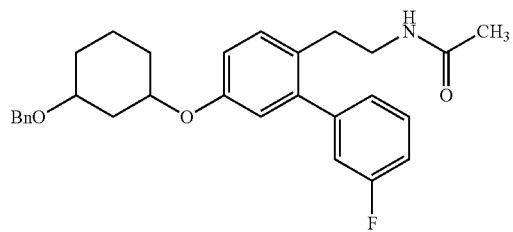 [SMILES: CC(=O)NCCc1ccc(OC2CCCC(OCc3ccccc3)C2)cc1-c1cccc(F)c1] |
| 38 | 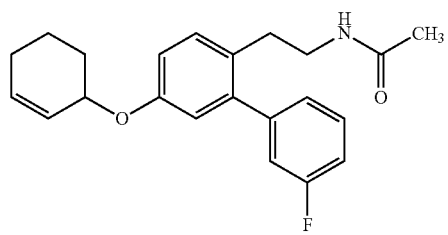 [SMILES: CC(=O)NCCc1ccc(OC2C=CCCC2)cc1-c1cccc(F)c1] |

TABLE 1-continued
Examples of Biphenyl and Coumarin Compounds Provided Herein
| Compound Number | Structure |
| --- | --- |
| 37 | 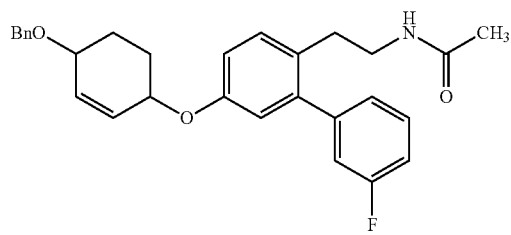 [SMILES: CC(=O)NCCc1ccc(OC2C=CC(OCc3ccccc3)CC2)cc1-c1cccc(F)c1] |
| 39 | 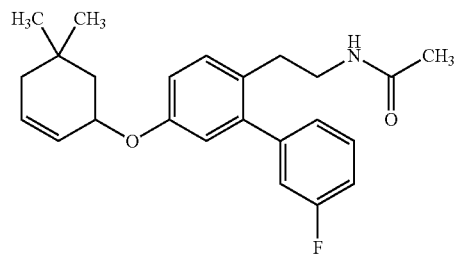 [SMILES: CC(=O)NCCc1ccc(OC2C=CCC(C)(C)C2)cc1-c1cccc(F)c1] |
| 46 | 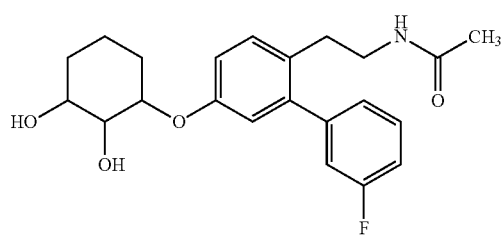 [SMILES: CC(=O)NCCc1ccc(OC2CCCC(O)C2O)cc1-c1cccc(F)c1] |
| 45 | 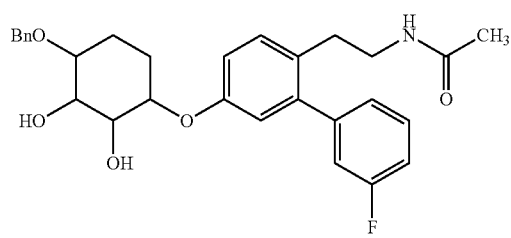 [SMILES: CC(=O)NCCc1ccc(OC2CCC(OCc3ccccc3)C(O)C2O)cc1-c1cccc(F)c1] |
| 82 | 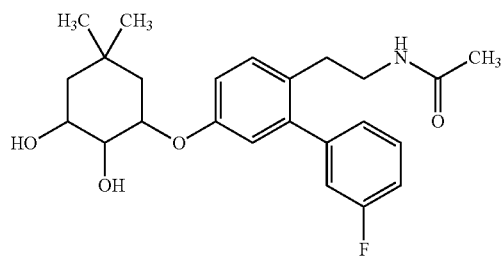 [SMILES: CC(=O)NCCc1ccc(OC2CC(C)(C)CC(O)C2O)cc1-c1cccc(F)c1] |
| 49 | 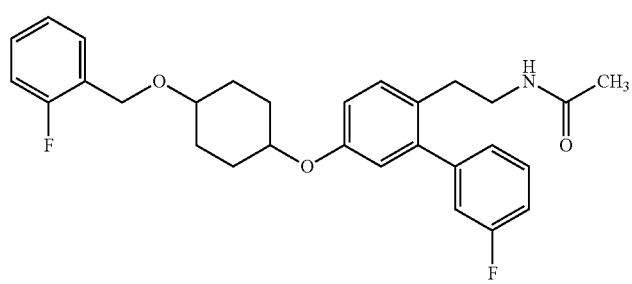 [SMILES: CC(=O)NCCc1ccc(OC2CCC(OCc3ccccc3F)CC2)cc1-c1cccc(F)c1] |

TABLE 1-continued
Examples of Biphenyl and Coumarin Compounds Provided Herein
| Compound Number | Structure |
|---|---|
| 50 | 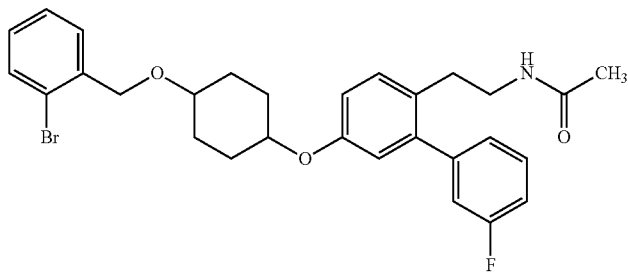 |
| 51 | 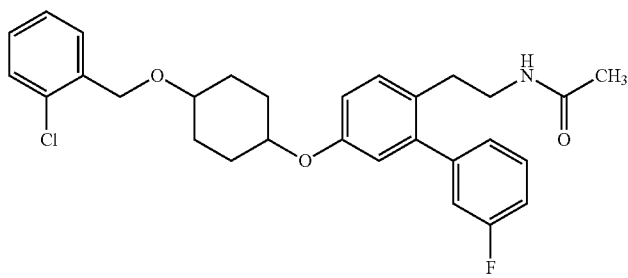 [SMILES: CC(=O)NCCc1ccc(OC2CCC(OCc3ccccc3Cl)CC2)cc1-c1cccc(F)c1] |
| 52 | 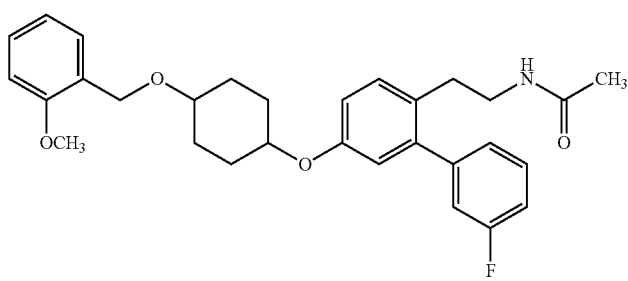 [SMILES: COc1ccccc1COC1CCC(Oc2ccc(CCNC(C)=O)c(-c3cccc(F)c3)c2)CC1] |
| 53 | 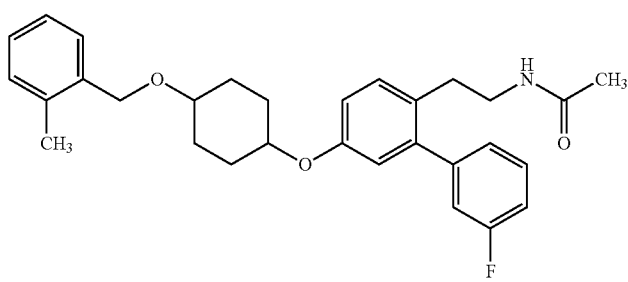 [SMILES: CC(=O)NCCc1ccc(OC2CCC(OCc3ccccc3C)CC2)cc1-c1cccc(F)c1] |
| 54 | 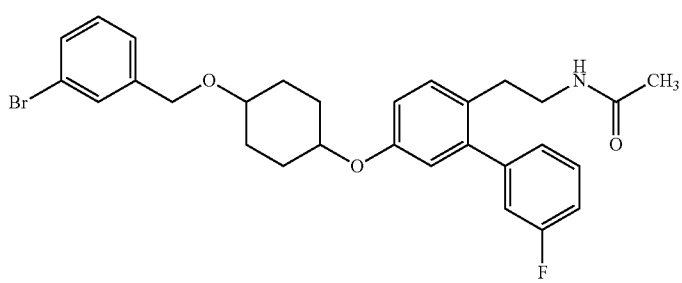 [SMILES: CC(=O)NCCc1ccc(OC2CCC(OCc3cccc(Cl)c3)CC2)cc1-c1cccc(F)c1] |

TABLE 1-continued
Examples of Biphenyl and Coumarin Compounds Provided Herein
| Compound Number | Structure |
| --- | --- |
| 55 | 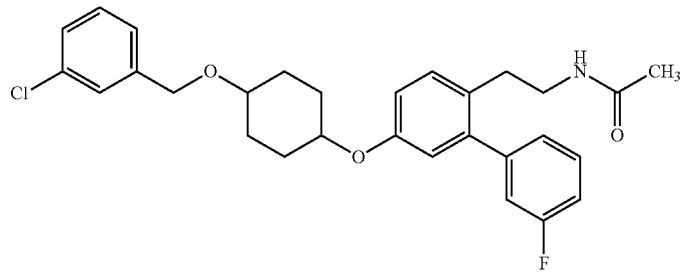 |
| 56 | 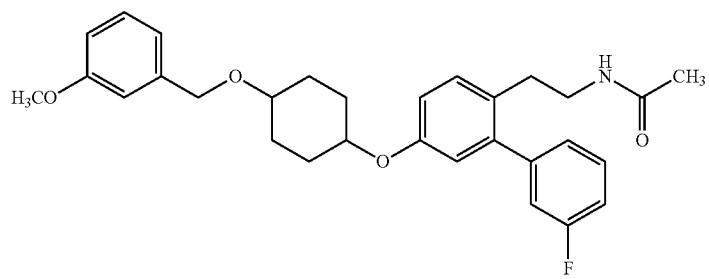 [SMILES: COc1cccc(COC2CCC(Oc3ccc(CCNC(C)=O)c(-c4cccc(F)c4)c3)CC2)c1] |
| 57 | 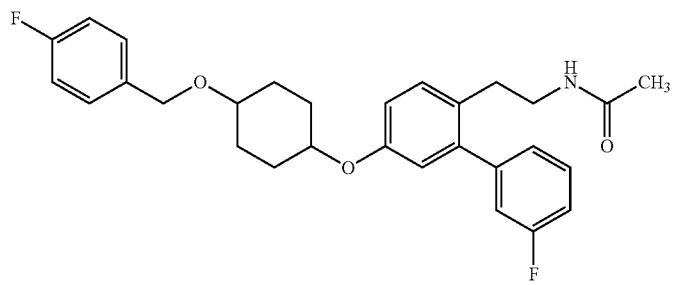 [SMILES: CC(=O)NCCc1ccc(OC2CCC(OCc3ccc(F)cc3)CC2)cc1-c1cccc(F)c1] |
| 58 | 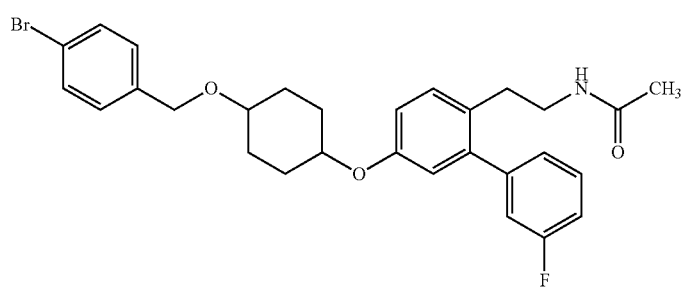 [SMILES: CC(=O)NCCc1ccc(OC2CCC(OCc3ccc(Cl)cc3)CC2)cc1-c1cccc(F)c1] |
| 59 | 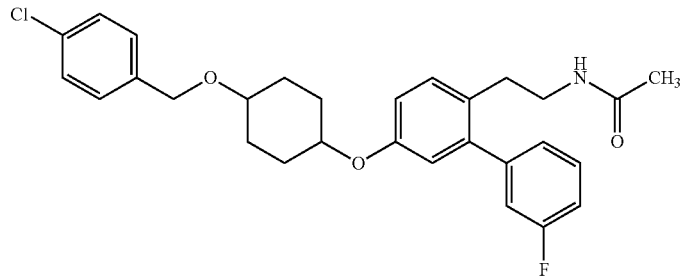 |

TABLE 1-continued
Examples of Biphenyl and Coumarin Compounds Provided Herein
| Compound Number | Structure |
|---|---|
| 60 | 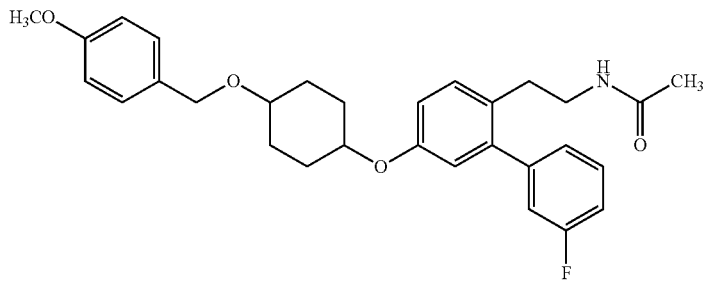 [SMILES: COc1ccc(COC2CCC(Oc3ccc(CCNC(C)=O)c(-c4cccc(F)c4)c3)CC2)cc1] |
| 61 | 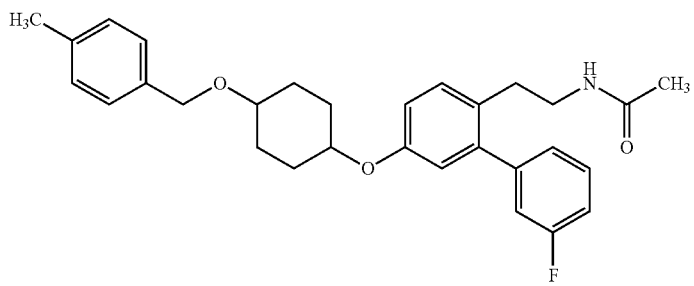 [SMILES: CC(=O)NCCc1ccc(OC2CCC(OCc3ccc(C(F)(F)F)cc3)CC2)cc1-c1cccc(F)c1] |
| 62 | 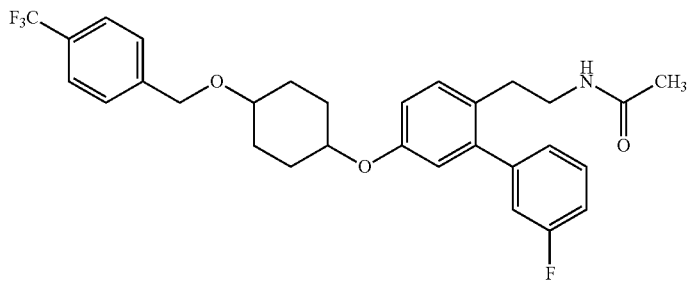 |
| 63 | 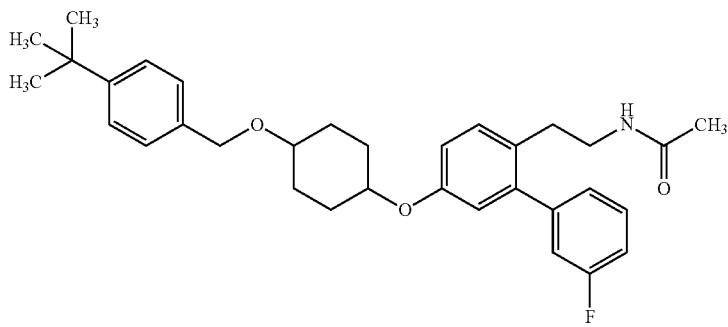 [SMILES: CC(=O)NCCc1ccc(OC2CCC(OCc3ccc(C(C)(C)C)cc3)CC2)cc1-c1cccc(F)c1] |
| 64 | 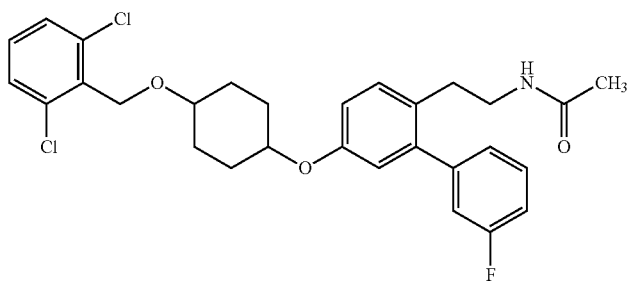 [SMILES: CC(=O)NCCc1ccc(OC2CCC(OCc3c(Cl)cccc3Cl)CC2)cc1-c1cccc(F)c1] |

TABLE 1-continued
Examples of Biphenyl and Coumarin Compounds Provided Herein
| Compound Number | Structure |
|---|---|
| 65 | 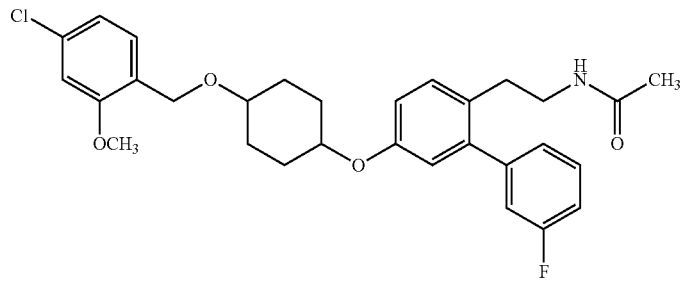 [SMILES: COc1cc(Cl)ccc1COC1CCC(Oc2ccc(CCNC(C)=O)c(-c3cccc(F)c3)c2)CC1] |
| 66 | 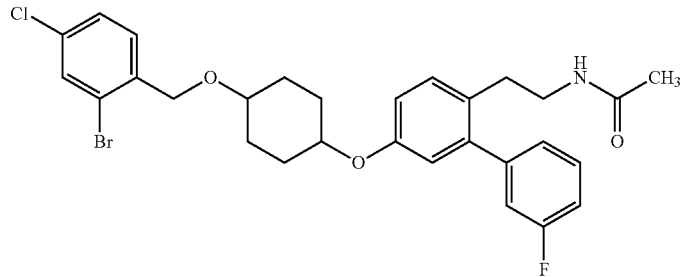 [SMILES: CC(=O)NCCc1ccc(OC2CCC(OCc3ccc(Cl)cc3Br)CC2)cc1-c1cccc(F)c1] |
| 68 | 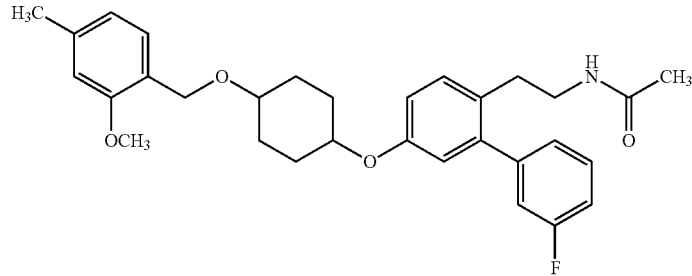 [SMILES: COc1cc(C)ccc1COC1CCC(Oc2ccc(CCNC(C)=O)c(-c3cccc(F)c3)c2)CC1] |
| 67 | 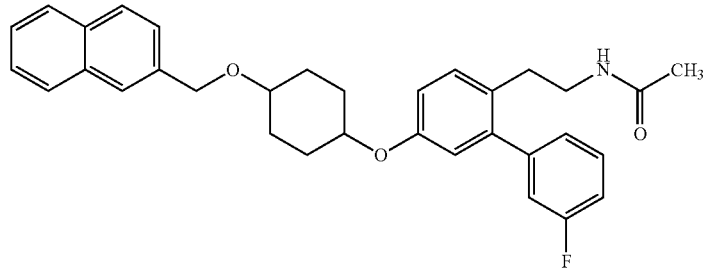 [SMILES: CC(=O)NCCc1ccc(OC2CCC(OCc3ccc4ccccc4c3)CC2)cc1-c1cccc(F)c1] |
| 74 | 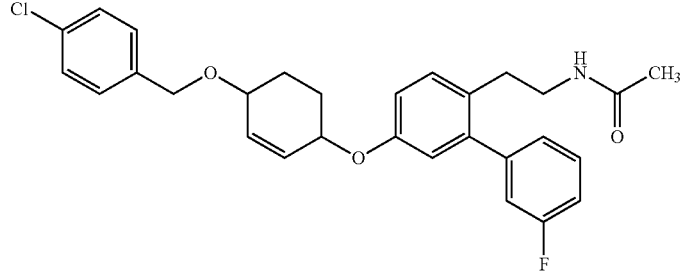 [SMILES: CC(=O)NCCc1ccc(OC2C=CC(OCc3ccc(Cl)cc3)CC2)cc1-c1cccc(F)c1] |

TABLE 1-continued

Examples of Biphenyl and Coumarin Compounds Provided Herein

| Compound Number | Structure |
|---|---|
| 75 | [structure] |
| 77 | [structure] |
| 78 | [structure] |
| 79 | [structure] |
| 80 | [structure] |

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Indications

A. Hsp70 Protein

In some embodiments, the compounds and compositions provided herein may be used to modulate the expression and/or activity of Hsp70 proteins. The Hsp70 protein functions as a chaperone protein assisting in protein folding and has a wide variety of different biological functions within normal cells. In particular, Hsp70 is associated with protein folding and transport of proteins into organelles, recognition of damaged proteins and assisting in the tagging of these proteins for destruction, and recognizes proteins carrying particular amino acid sequences and transports these proteins to specific organelles such as lysosomes. Without wishing to be bound by any theory, it is believed that as many as 30% of proteins interact with Hsp70 which ensures their proper folding and the Hsp70 interacts with the hydrophobic portions of proteins to prevent their degradation. Furthermore, Hsp70 also helps in the identification of irreversibly damaged proteins and sends those proteins to proteasomes for degradation. Such degradation occurs in conjunction with Bag-1 and CHIP proteins.

Additionally, the Hsp70 protein is associated with identifying and marking proteins which are degraded under fasting conditions or other low nutrient conditions. In particular, the presence of the amino acid sequence KFPRQ within a protein is known to trigger the protein for degradation under such conditions by the lysosome.

B. Hsp90 Protein

In some embodiments, the compounds and compositions of the present disclosure bind to the C terminus of the Hsp90 protein and thus prevent the binding of the natural substrate to the protein. The Hsp90 is a molecular chaperone protein, which in addition to assisting in protein folding, protein degradation, and mitigating heat stress, is implicated in stabilizing a number of proteins associated with cancer. Inhibition of the Hsp90 protein has been shown to lead to apoptosis of the cancerous cells. Without being bound by theory, a number of different molecular pathways are implicated in the Hsp90 protein's role in cancer development and proliferation. For example, the protein is implicated in stabilizing mutant oncogenic proteins such as v-Src, Bcr/Abl, and p53, stabilizing several growth factors and signaling molecules such as EGFR, PI3K, and AKT proteins which leads to growth factor signaling pathway promotion, and promotes the induction of VEGF, nitric oxide synthase, and the matrix metalloproteinase MMP2 which promote angiogenesis and metathesis of the cancerous cells. Many different cancer types and subtypes rely on pathways mediated by the Hsp90 protein for proliferation and tumor development thus inhibitors of the highly conserved Hsp90 protein may be used to treat a wide variety of cancers.

Additionally, inhibition of Hsp90 is known to activate heat shock factor-1 (HSF-1) which is used to induce other chaperone proteins such as Hsp40 and Hsp70. These chaperone proteins are used to promote disaggregation and protein degradation which is critical for the treatment of neurological diseases. In particular, the binding of the Hsp90 protein to an inhibitor releases the HSF-1 which then allows the activation of other cofactors and proteins. Without wishing to be bound by any theory, it is believed that the inhibition of Hsp90 triggers the increased production and/or activity of Hsp70. Furthermore, Hsp90 is believed to also stabilize aberrant proteins in numerous neurological diseases. The Hsp90 protein binds to these aberrant proteins and in some embodiments, prevents their degradation and/or increases protein stabilization (Luo, et al., 2010)

C. Hyperproliferative Diseases

The compound of the present disclosure may be used in the treatment of diseases or disorders with result from the unnatural proliferation of cells. In some aspects, this disease or disorder is cancer. The compound may be used to treat cancer cells according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

D. Neurological Disorders

The term "neurodegenerative disease or disorder" and "neurological disorders" encompass a disease or disorder in which the peripheral nervous system or the central nervous system is principally involved. The compounds, compositions, and methods provided herein may be used in the treatment of neurological or neurodegenerative diseases and disorders. As used herein, the terms "neurodegenerative disease", "neurodegenerative disorder", "neurological disease", and "neurological disorder" are used interchangeably. Without being bound by any theory, it is believed that the compounds and compositions of the present disclosure provide neuroprotective effects by modulating the activity of Hsp90 and thus inhibiting the progressive deterioration of neurons that leads to cell death.

Examples of neurological disorders or diseases include, but are not limited to chronic neurological diseases such as diabetic peripheral neuropathy (including third nerve palsy, mononeuropathy, mononeuropathy multiplex, diabetic amyotrophy, autonomic neuropathy and thoracoabdominal neuropathy), Alzheimer's disease, age-related memory loss, senility, age-related dementia, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis ("MS"), synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff's related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In some embodiments, the neurodegenerative disorder is amyloidosis. Amyloidosis is observed in Alzheimer's Disease, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis. In preferred embodiments, the neurodegenerative disorder treated and/or prevented using the methods and compositions of the disclosure is diabetic peripheral neuropathy.

E. Diabetes and Complications from Diabetes

The compounds described herein may be used to treat diabetes or a complication arising from diabetes. In some embodiments, the complication arising from diabetes is associated with glucose toxicity. When someone with diabetes becomes hyperglycemic, the excess glucose may result in toxicity to different organ tissues including neurons, the kidneys, the eyes, and the vessels. In some embodiments, the glucose toxicity results in damage to the sensory neurons and results in a condition known as diabetic peripheral neuropathy. Diabetic peripheral neuropathy may result in tingling, numbness, burning and/or pain. These symptoms are observable in the feet and legs but also may affect the arms, abdomen, and the back. Additionally, in advanced cases, some people report muscle weakness, sensitivity to touch, loss of reflexes, loss of balance, and serious foot conditions such as ulcers, infections, and joint pain. While the toxic event results from blood glucose being too high, the symptoms and the condition may persist even after blood glucose has been regulated. In such cases, traditional care has often been palliative and to ease the symptoms rather than treating the underlying condition. Other times, when caught early, the symptoms may go away after the glucose level has been regulated.

F. Diseases Associated with Mitochondrial Dysfunction

Among its other functions, Hsp70 plays an important role in regulating the importation of nuclear-encoded mitochondrial proteins into the matrix of the mitochondria, and promoting their proper processing and folding following importation (Harbauer, et al., 2014). A compound mechanistically related to the compounds of the present invention, KU-32, has been shown to improve mitochondrial bioenergetics (Ma, et al., 2014). Thus, compounds of the present disclosure may be used to prevent or treat diseases or disorders involving mitochondrial dysfunction. Non-limiting examples of these include a wide variety of neurological disorders including neurodegenerative diseases, epilepsy, psychiatric diseases including depression, schizophrenia, and bipolar disorder, neurodevelopmental disorders including autism and attention deficit disorders, neuromuscular disorders including Friedreich's ataxia, mitchondrial myopathy, muscular dystrophy, and various forms of dystonia, muscle wasting diseases including aging-related muscle wasting, diabetes-related muscle wasting, cancer-related cachexia, cachexia associated with dialysis, anorexia-related cachexia, and myasthenia gravis, impaired function of cardiac muscle associated with heart failure and other forms of cardiovascular disease, disorders of the retina, obesity, diabetes, and complications of diabetes.

III. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compounds by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compounds into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compounds may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, the effective dosing amount that may be used is an amount sufficient to cause greater than 10% reduction in number of cancerous cells. In other embodiments, an effective dosing amount is sufficient to reduce the tumor volume by greater than 10% over a given time period compared to the volume before administration of the compound. In other embodiments, the effective amount is measured based upon the treatment with the compound and one or more different pharmaceutical agents or modalities.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.01% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

IV. Combination Therapy

In addition to being used as a monotherapy, the compounds of the present disclosure may also be used in combination therapies. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. Such second therapies include, but are not limited to, surgery, immunotherapy, radiotherapy, or a second chemotherapeutic agent. In some embodiments, the second chemotherapeutic agent is a N-terminus Hsp90 inhibitor such as geldanamycin, radicicol, the geldanamycin derivative 17AAG, NVP-AUY922, or gamitrinib. A variety of different Hsp90 inhibitors which may be used in combination with compounds provided herein are described in Jhaveri, et al., 2012, which is incorporated herein by reference.

V. Definitions

The definitions below supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

A. Chemical Groups

When used in the context of a chemical group: "hydrogen" means —H; "hydroxy" means —OH; "oxo" means =O; "carbonyl" means —C(=O)—; "carboxy" means —C(=O)OH (also written as —COOH or —CO2H); "halo" and "halogen" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "====" represents a single bond or a double bond. Thus, for example, the formula

includes

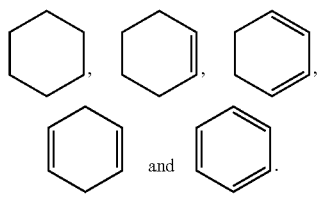

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〰", when drawn perpendicularly across a bond

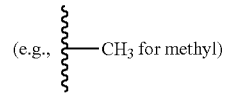

indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

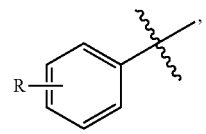

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

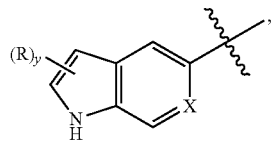

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$C$_1$.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

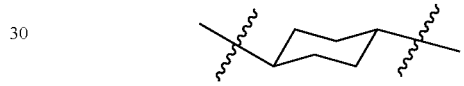

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples are: pyridinylmethyl and 2-furylmethyl. When the term aralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted heteroaralkyls are: 3-(2-chloropyridinyl)methyl and 2-(3-hydroxyquinonyl)-methyl.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "aryloxy", "aralkoxy", "heteroaryloxy", "heteroaralkoxy", and "acyloxy", when used without the "substituted" modifier, refers to groups, defined as —OR, in which R is cycloalkyl, alkenyl, aryl, aralkyl, heteroaryl, heteroaralkyl, and acyl, respectively.

The term "alkylthio" and "acylthio" when used without the "substituted" modifier refers to the group —SR, in which R is an alkyl and acyl, respectively. The term "alcohol"

corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "alkylamino" when used without the "substituted" modifier refers to the group —NHR, in which R is an alkyl, as that term is defined above. Non-limiting examples include: —$NHCH_3$ and —$NHCH_2CH_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —$N(CH_3)_2$ and —$N(CH_3)(CH_2CH_3)$. The terms "cycloalkylamino", "alkenylamino", "arylamino", "aralkylamino", "heteroarylamino", "heteroaralkylamino", and "alkoxyamino", when used without the "substituted" modifier, refers to groups, defined as —NHR, in which R is cycloalkyl, alkenyl, aryl, aralkyl, heteroaryl, heteroaralkyl, and alkoxy, respectively. A non-limiting example of an arylamino group is —$NHC_6H_5$. The term "amido" (acylamino), when used without the "substituted" modifier, refers to the group —NHR, in which R is acyl, as that term is defined above. A non-limiting example of an amido group is —$NHC(O)CH_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The groups —$NHC(O)OCH_3$ and —$NHC(O)NHCH_3$ are non-limiting examples of substituted amido groups.

B. Other Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon atoms), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide; OCR, oxygen consumption rate; ECAR, extracellular acidification rate; MRC, maximal respiratory capacity; FCCP, carbonyl cyanide-p-trifluoromethoxyphenylhydrazone; SDS-PAGE, sodium dodecyl sulfate polyacrylamide gel electrophoresis; PBST, phosphate buffered saline with 0.1% Tween 20; HRP, horseradish peroxidase; EDTA, ethylenediaminetetraacetic acid; DMEM, Dulbecco's Modified Eagle Medium; EtOAc, ethyl acetate; NMO, N-methylmorpholine N-oxide; THF, tetrahydrofuran, Me, methyl; NMR, nuclear magnetic resonance; DMF, N,N-dimethylformamide; TBAI, tetrabutylammonium iodide; GDA, geldanamycin; or BN or Bn, benzyl.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods and Materials

A. Mitochondrial Bioenergetic (mtBE) Assessment

Oxygen consumption rate (OCR) was assessed in the 50B11 transformed sensory neuron cell line, using an XF96 Extracellular Flux Analyzer (Seahorse Biosciences, North Billerica, Mass.). 50B11 cells were seeded into the 96 well plates at 40,000 cells per well and maintained in high glucose DMEM supplemented with 10% fetal bovine serum (Atlas Biologics, Fort Collins Colo.), 5 µg/ml blasticidin and antibiotics at 37° C. The maintenance media was changed to serum free unbuffered DMEM supplemented with 1 mM pyruvate and 5.5 mM D-glucose and the cells incubated at 37° C. in room air for one hour before starting the assay. After introducing the plate into the XF96 analyzer, the basal oxygen consumption rate (OCR) was measured prior to the addition of 1 µg/ml oligomycin to inhibit the ATP synthase to measure the portion of the basal OCR that was coupled to ATP synthesis; residual OCR after oligomycin treatment is from uncoupled respiration (proton leak). Next, 1 µM of the protonophore FCCP was injected to dissipate the proton gradient across the inner mitochondrial membrane to measure maximal respiratory capacity (MRC). The final injection of 1 µM rotenone+1 µM antimycin A was used to assess non-mitochondrial respiration. The XF96 analyzer also measures the rate of extracellular acidification as a marker of glycolytic activity coincident with the assessment of mitochondrial OCR.

After the respiratory measures, the cells were harvested and the protein content of each well determined using a Bradford protein assay. OCR values were normalized to the total protein content of each well and ATP-linked respiration, proton leak, maximal respiratory capacity, spare respiratory capacity and respiratory control ratio were determined as described (Brand and Nicholls, 2011; Chowdhury, et al., 2012)

B. Luciferase Reporter Assay, Immunoblot Analysis and Client Protein Degradation The luciferase reporter assay was performed using a 1.5 kb region upstream of the start codon of the human HSPA1A gene to drive luciferase expression as previously described. 50B11 cells (Chen, et al., 2007) were grown in 10 cm dishes in maintenance medium and the cells were transfected using lipofectamine. Twenty four hour after transfection, the cells were re-seeded into 24 well plates at a density of $2 \times 10^5$ cells per well. After a 6 hrs period to permit attachment, the cells were treated with the indicated compounds for 16 hrs. Luciferase activity was assessed and normalized to the total protein concentration of each well.

50B11 cells were treated with the indicated compounds for 24 hrs and were scraped into lysis buffer containing 50 mM Tris-HCl, pH 7.4, 150 mM NaCl, 1 mM EDTA, 1% NP-40, 0.5 mM sodium orthovandate, 40 mM NaF, 10 mM β-glycerophosphate, and Complete Protease Inhibitors (Roche Diagnostics). After 15 minutes on ice, the lysates were sonicated then centrifuged at 10,000×g for 10 min at 4° C. The protein concentration of the supernatant was estimated using a Bio-Rad protein assay and bovine serum albumin as the standard. Following SDS-PAGE, the proteins were transferred to nitrocellulose and the membrane incubated with 5% non-fat dry milk in phosphate buffered saline containing 0.1% Tween 20 (PBST) for 1-2 hrs at room temperature. The blots were probed with primary antibodies recognizing Hsp70 or R-actin at 4° C. overnight. The membranes were washed with PBST and subsequently incubated with HRP-conjugated secondary antibodies and immunoreactive proteins were visualized using chemiluminescence detection (GE Healthcare Life Sciences, Little Chalfont, Buckinghamshire, UK). The films were digitally scanned and densitometrically analyzed using ImageJ (NIH) software. Client protein degradation in MCF7 cells was performed as previously described (Urban, et al., 2010).

Example 1: Induction of Hsp70 and Cytoprotective Activity of Compounds

Since the cytoprotective activity manifested by KU-32 and KU-596 had been shown to require Hsp70 (Kusuma, et al., 2012), the compounds described herein were tested for their ability to induce Hsp70 via a luciferase reporter assay (Baylon, et al., 1999).

FIG. 1 shows the induction of the compounds for the expression of the Hsp70 promoter with 44 inducing the highest expression of the Hsp70 promoter. Without wishing to be bound by any theory, it is believed that the analogs binds into the C-terminal binding site and the aryl ring projects further into the binding pocket to allow additional interactions based upon the docking studies. Based upon these docking studies, the introduction of substituents in the para and ortho position appear to orient the substitutions in a beneficial manner (such as the shown para-Cl 59). On the other hand, based upon these docking studies, substitutions at the meta-position may be detrimental and exhibit unfavorable interactions within the binding pocket. Based upon these docking studies, numerous different substituted benzyl groups were chosen and synthesized to empirically confirm the docking studies. Substituents that modulate the electronic and steric parameters of the compound were chosen to probe the structure-activity relationship and to maximize the interactions of the compound with the pocket.

Figure 2:
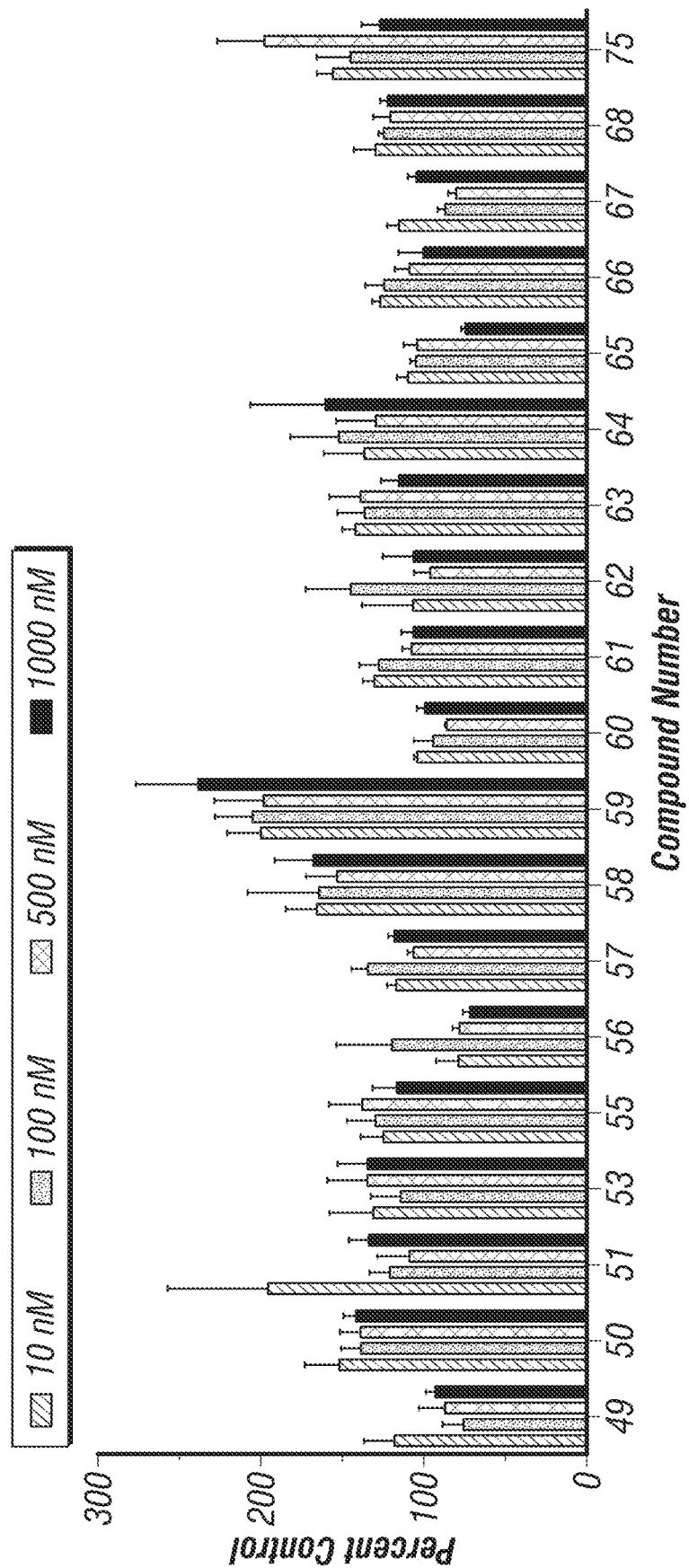
FIG. 2 shows the results of the luciferase assay assessing Hsp70 induction by analogs 49-68 and 75 with DMSO (negative control) assigned a value of 100. Results are mean±standard error of the mean (SEM). (n=3-9) for four compound concentrations: 10 nM, 100 nM, 500 nM, and 1,000 nM. The para-substituted analogs (57-63) showed more robust induction of Hsp70 then the corresponding ortho-substituted (49-51) and meta-substituted derivatives (55-56). Compound 75 which is a para-substituted analog containing a cyclohexyl cis-diol, was also tested and showed good induction of Hsp70.

The ability of these modified benzyl compounds was evaluated for their ability to induce Hsp70 (FIG. 2). In general, the para substituted analogs (57-63) showed more robust induction of Hsp70 then the corresponding ortho substituted analogs (49-53) and meta substituted analogs (54-56). These results are consistent with the docking studies discussed above wherein the meta substituted analogs would have unfavorable steric interactions with the binding pocket. 75, which is a para-substituted analog containing a cyclohexyl cis-diol, also yielded good induction of the Hsp70 promoter.

The scaffolds, 20 and 76, without either the noviose sugar or a sugar mimic, were tested and found to be inactive highlighting the importance of this group. KU-32 coumarin analogs of the most active benzyl derivatives were prepared and exhibited less activity than their biaryl counterparts (Table 2).

TABLE 2

Unsubstituted Scaffolds 20 and 76 and Coumarin-Based Compounds 77-80.

| Compound | 10 nM Mean | 10 nM SEM | 100 nM Mean | 100 nM SEM | 500 nM Mean | 500 nM SEM | 1000 nM Mean | 1000 nM SEM |
|---|---|---|---|---|---|---|---|---|
| 20 | 88.07 | 16.95 | 87.40 | 23.96 | 93.87 | 20.29 | 96.56 | 11.98 |
| 76 | 100.26 | 7.38 | 97.38 | 4.86 | 97.00 | 5.24 | 120.39 | 10.87 |
| 77 | 146.19 | 19.77 | 106.40 | 6.72 | 102.93 | 10.73 | 100.29 | 6.91 |
| 78 | 85.73 | 5.62 | 94.52 | 5.28 | 97.39 | 8.49 | 105.69 | 8.91 |
| 79 | 105.83 | 8.08 | 102.65 | 6.70 | 97.09 | 7.83 | 91.42 | 4.90 |
| 80 | 130.87 | 17.76 | 151.51 | 8.49 | 129.16 | 9.87 | 142.77 | 2.71 |

Figure 3A:
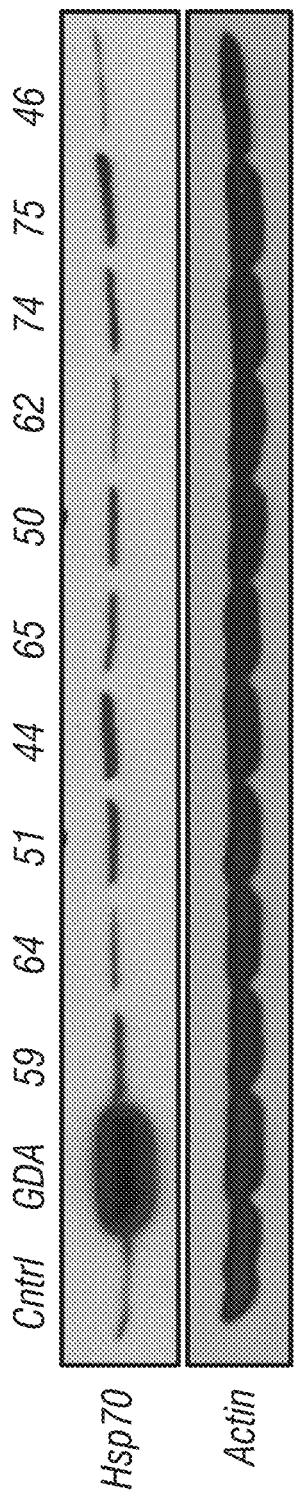
FIGS. 3A & 3B show the induction of Hsp70 protein expression by some of the compounds described herein.
Figure 3B:
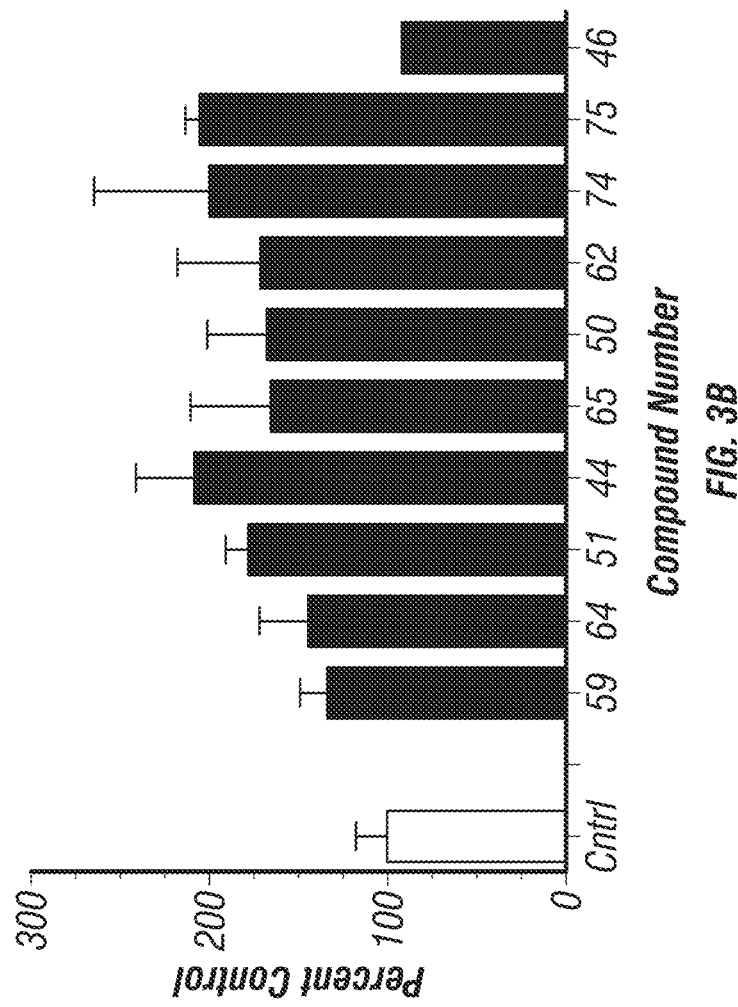

To further examine the effect of select analogs on Hsp70 protein expression, immunoblot analysis was performed. Consistent with the induction of luciferase activity via the Hsp70 promoter, 44 also induced Hsp70 protein expression (FIG. 3B). 59 was less effective in the immunoblot analysis despite robust induction of Hsp70 promoter in the luciferase activity (FIG. 3A). In general, the addition of a cis diol to the cylohexyl ring increased Hsp70 protein expression compared to the induction of the Hsp70 promoter. The remaining para substituted and ortho substituted compounds were similarly effective in the luciferase activity and the immunoblot analysis.

Figure 4:
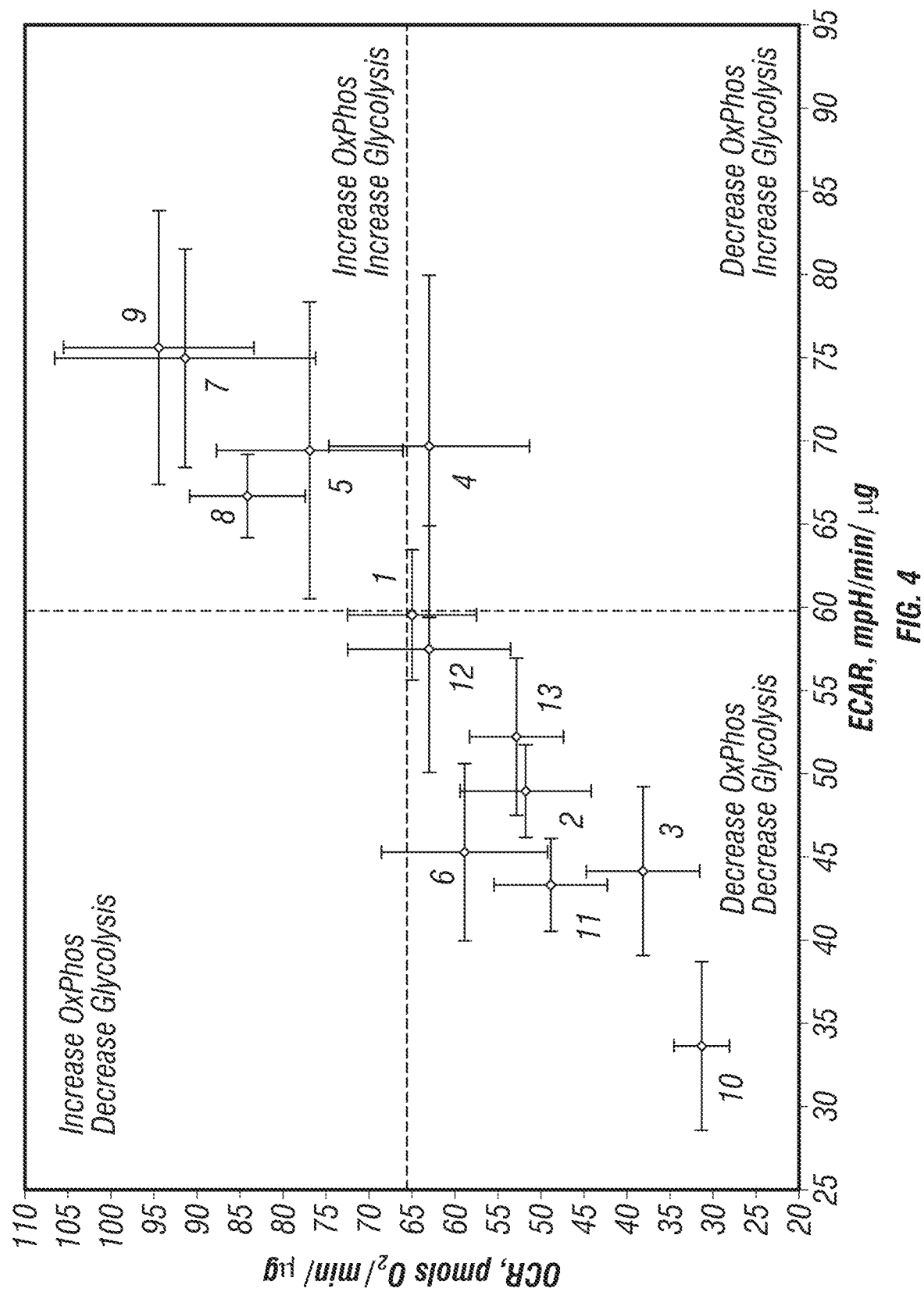
FIG. 4 shows the mitochondrial function for compounds 59, 74, and 75. 50B11 cells were treated for 24 hr with DMSO (1), 10 nM (2,6,10), 100 nM (3,7,11), 500 nM (4,8,12) or 1,000 nM (5,9,13) of compounds 74 (2-5), 75 (6-9) or 59 (10-13). Mitochondrial respiration was measured in the intact cells using an XF96 extracellular flux analyzer that provides concurrent measures of mitochondrial oxygen consumption rate (OCR) and extracellular acidification rate (ECAR) as an indication of glycolytic activity. Results are plotted OCR versus ECAR. The net effect of the drugs on oxidative phosphorylation and glycolysis is indicated in each quadrant. Results are mean±standard error of the mean (SEM) (n=6). Although compounds 74 and 75 showed equivalent levels of Hsp70 induction, 75 was more effective at dose dependently increasing oxidative phosphorylation and glycolysis compared to 59 and 75.

The neuroprotective efficacy of KU-32 in improving symptoms of diabetic peripheral neuropathy has been shown to be associated with an increase in mitochondrial respiration (Ma, et al., 2014). To determine if the increase in Hsp70 expression correlated with an effect on mitochondrial respiration, 50B11 cells were treated with analogs 59, 74 or 75 for 24 hrs. Mitochondrial respiration was measured in the intact cells using an XF96 extracellular flux analyzer that provides concurrent measures of mitochondrial oxygen consumption rate (OCR) and extracellular acidification rate (ECAR) as an indication of glycolytic activity. Although compounds 74 and 75 showed equivalent levels of Hsp70 induction, 75 was more effective at dose dependently increasing oxidative phosphorylation and glycolysis compared to 59 and 74. While 59 and 75 differ only by the presence of the cis diol on the cyclohexyl ring, 59 decreased cellular respiration but 75 increased cellular respiration. See FIG. 4.

Example 2: Compounds and Synthesis

A. Synthesis

A series of simplified pyranoses that closely mimic the noviose chair conformation were chosen to identify simplified ether groups which maintained activity.

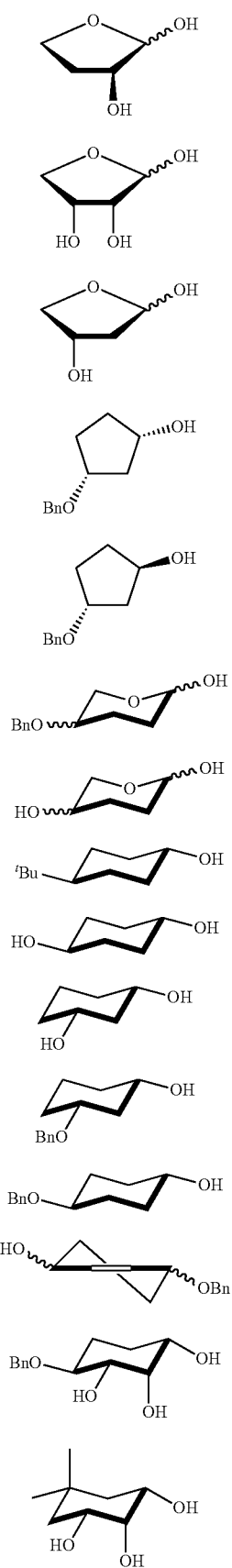

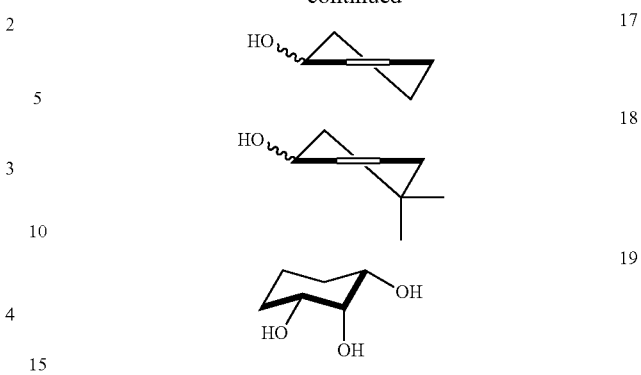

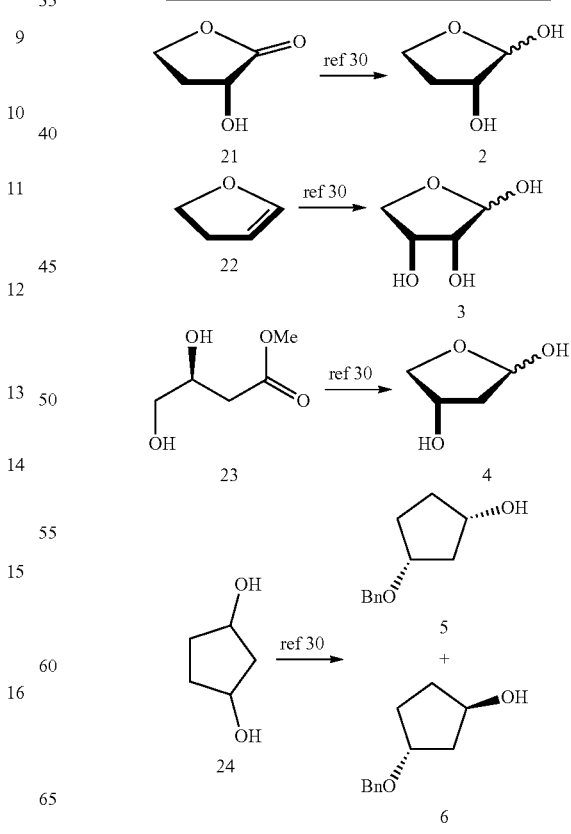

Ring contracted furanose analogs may resemble envelope conformations that can project substituents into unexplored regions of the Hsp90 C-terminal binding pocket. Syntheses of sugars can require multiple steps, therefore, more simplified analogs such as cyclohexyl and cyclopentyl derivatives were pursued to determine whether a carbocyclic analog also exhibits beneficial activity. Analogs that contain alkyl and aralkyl substituents were pursued to determine the constraints of the binding pocket. Furanose derivatives 2, 3 and 4, were synthesized from 21, 22 and 23, respectively, via reported procedures (Yu, et al., 2005) whereas cyclopentanes 5 and 6 were obtained from monobenzylation of commercially available 1,3-cyclopentadiol, 24. The resulting syn- and anti-isomers were separated by column chromatography (Scheme 1).

Compound 7 was obtained from 3,4-dihydro-2-methoxy-pyran, 25, via a 4-step procedures (Beaver, et al., 2008) and the benzyl groups removed to give 8. Cyclohexane derivatives 9, 10 and 11 are commercially available, whereas 12 and 13 were obtained from monobenzylation of 11 and 10, respectively. Cyclohexene derivatives 14, 17 and 18 were synthesized via published procedures from 27, 26 and 28 respectively (Scheme 2) (Zhao, et al., 2011).

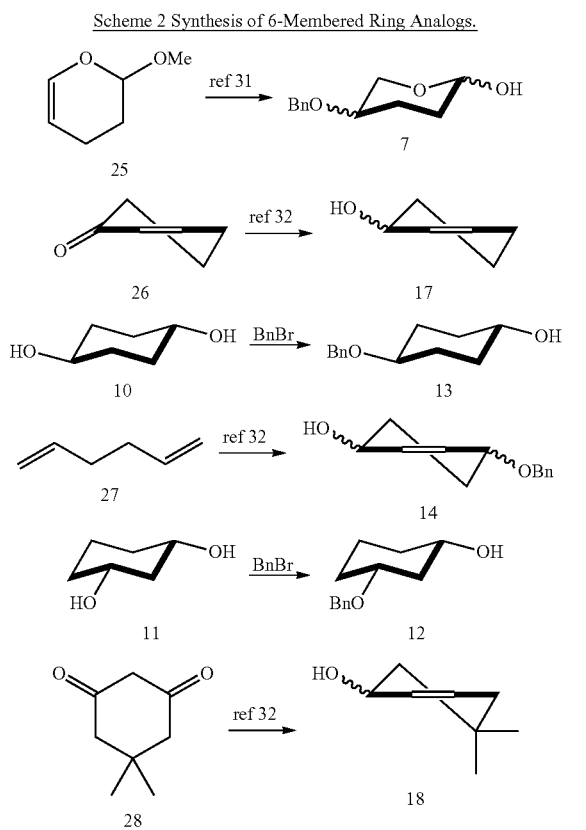

Synthesis of phenol 20 commenced by benzyl protection of 2,4-dihydroxybenzaldehyde, 29. The resulting benzyl ether was converted to trifluoromethanesulfonate 30 in the presence of trifluoromethanesulfonic anhydride and triethylamine. A subsequent Suzuki coupling reaction with commercially available 3-fluorophenyl boronic acid was employed to generate the biaryl ring system found in 31, which was then subjected to a Henry reaction, followed by simultaneous reduction of both the nitro and olefin functionalities with lithium aluminum hydride to yield amine 32.

Scheme 3 Synthesis of Phenol 20.

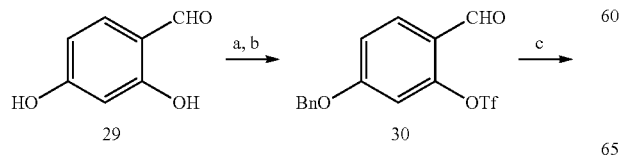

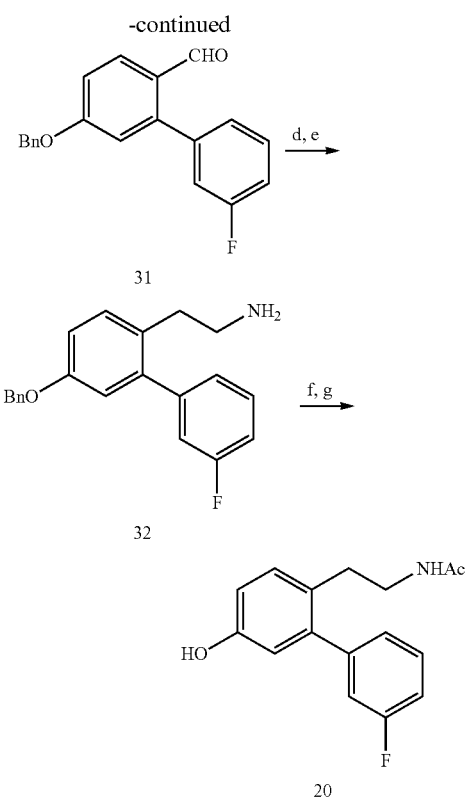

reaction conditions: a. BnBr, NaHCO$_3$, CH$_3$CN, 75%; b. (CF$_3$CO)$_2$O, Et$_3$N, DCM, 60%; c. 3-fluoro-phenylboronic acid, Pd(PPh$_3$)$_4$, K$_2$CO$_3$, DMF, 90%; d. CH$_3$NO$_2$, NH$_4$OAc, 98%; e. LiAlH$_4$, THF, 30 min, f. Ac$_2$O, Et$_3$N, 72% over 2 steps, g. H$_2$, Pd/C, MeOH, 90%.

Acylation of 32 was followed by cleavage of the benzyl ether under hydrogenolysis conditions to afford the phenol, 20.

Desired compounds 33-39 were obtained by a Mitsunobu reaction between phenol 20 and the corresponding sugars/sugar surrogates, while compounds 40-44 were obtained via S$_N$2 substitution reaction between phenol 20 and the toluenesulfonates (Scheme 4).

Scheme 4 Synthesis of Compounds 33-44 via (A) a Mitsunobu Etherification, or (B) a S$_N$2 Substitution

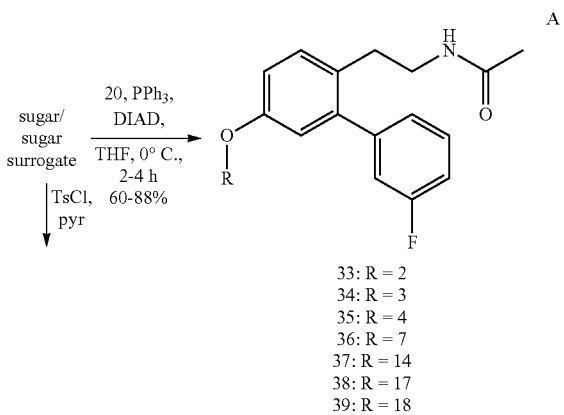

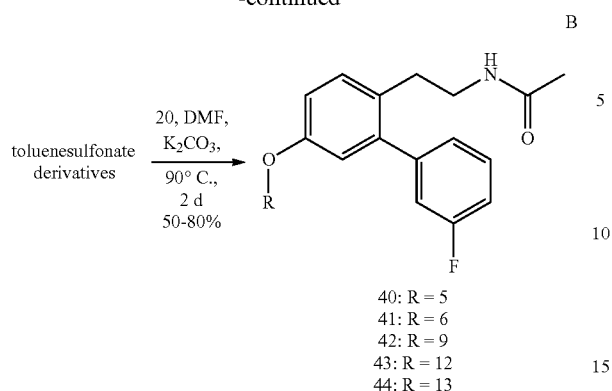

40: R = 5
41: R = 6
42: R = 9
43: R = 12
44: R = 13

To obtain compounds 45, 46, and 82, 37, 38, and 39 were subjected to OsO₄ catalyzed dihydroxylation to obtain the corresponding diols. Cleavage of the benzyl ethers present in 36, 43, and 44 via hydrogenolysis afforded 47, 81, and 48, respectively (Scheme 5).

Scheme 5 Synthesis of Compounds 45-48, 81, and 82

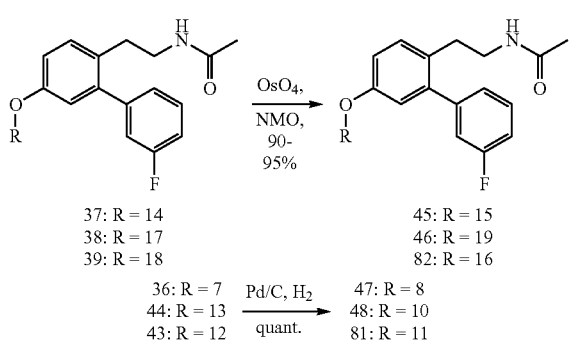

37: R = 14
38: R = 17
39: R = 18

45: R = 15
46: R = 19
82: R = 16

36: R = 7
44: R = 13
43: R = 12

47: R = 8
48: R = 10
81: R = 11

Synthesis of substituted benzyl analogs began by selective conversion of commercially available 1,4-cyclohexane diol 69, to the corresponding toluenesulfonate derivative, 70, followed by formation of the benzyl ethers containing the appropriately substituted benzylbromides. An $S_N2$ reaction between phenol 20 and these toluenesulfonates gave compounds 49-68 (Scheme 6).

Scheme 6 Synthesis of Benzyl Substituted Compounds.

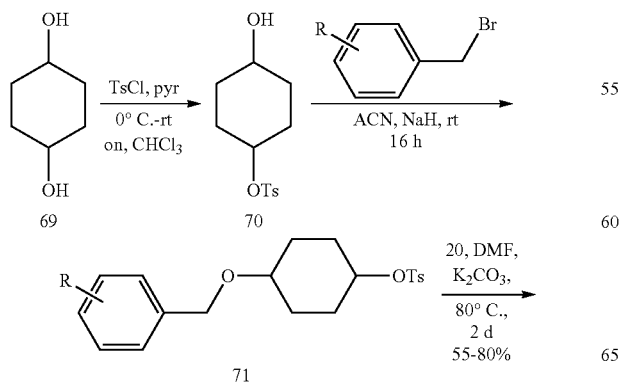

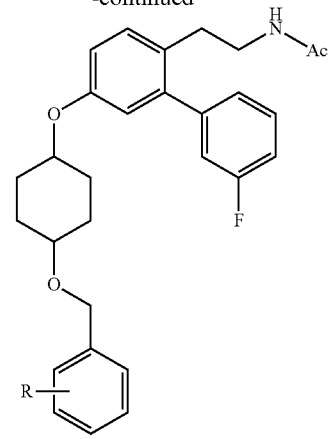

49-68
49: R = o-F; 50: R = o-Br; 51: R = o-Cl, 52: R = o-OCH₃;
53: R = o-CH₃; 54: R = m-Br; 55: R = m-Cl; 56: R = m-OCH₃,
57: R = p-F; 58: R = p-Br; 59: R = p-Cl; 60: R = p-OCH₃;
61: R = p-CH₃; 62: R = p-CF₃; 63: R = p-tBu; 64: R = 2, 6-dichloro;
65: R = 2-OCH₃, 4-Cl; 66: R = 2-Br, 4-Cl; 67: R = 2-naphthalene;
68: R = 2-OCH₃, 4-CH₃

Similarly, compound 75 was synthesized from 1,4-cyclohexene diol, 72 as shown in Scheme 7. This was designed to closely mimic the 2',3'-diol presence in noviose to potentially increase hydrogen-bonding interactions of 59 with the C-terminus binding pocket of the Hsp90 protein.

Scheme 7 Synthesis of 75.

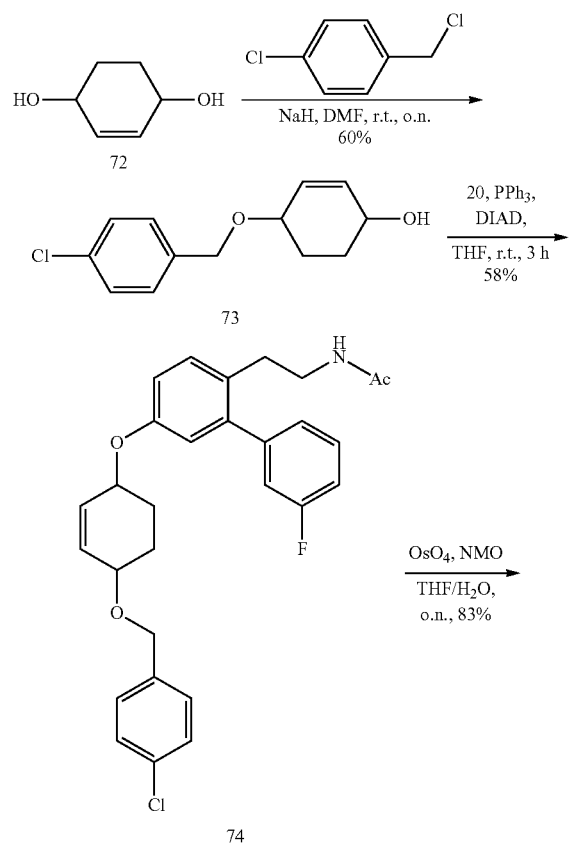

-continued

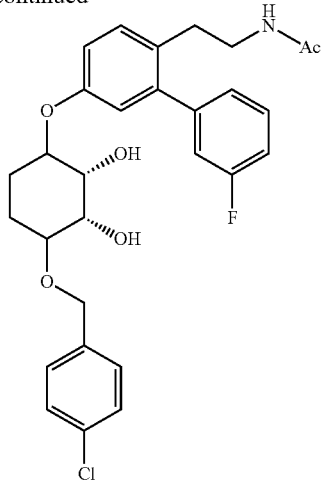

75

B. Compound Characterization

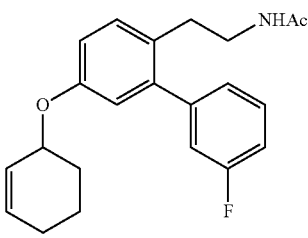 [SMILES: CC(=O)NCCc1ccc(OC2C=CCCC2)cc1-c1cccc(F)c1]

N-(2-(3'-fluoro-5-((3-hydroxytetrahydrofuran-2-yl)oxy)-[1,1'-biphenyl]-2-yl)ethyl)acetamide (38)

Diisopropylazodicarboxylate (85 µL, 0.4 mmol) was added slowly to a solution of phenol 20 (55 mg, 0.2 mmol), cycloalkene 17 (20 mg, 0.2 mmol) and triphenylphosphine (104 mg, 0.4 mmol) in THF (1 mL) at 0° C. The resulting reaction mixture was stirred at room temperature for 3 h, quenched with water and extracted with EtOAc (2×10 mL). The combined organic extracts were washed with saturated sodium chloride solution, dried over anhydrous $Na_2SO_4$, filtered, and concentrated. The crude product was purified via column chromatography ($SiO_2$, 100:1, $CHCl_3$:MeOH) to afford 38 as a mixture of diastereomers.

$^1$H NMR (500 MHz, CDCl$_3$) δ 7.3 (m, 1H), 7.12 (d, J=5 Hz, 1H), 6.97 (m, 2H), 6.83 (dd, J=5 Hz, 1H), 6.71 (d, 1H), 5.87 (m, 2H), 5.23 (br, s, 1H), 4.72 (br, s, 1H), 3.20 (q, J=3 Hz, 2H), 2.55 (t, J=3 Hz, 2H), 2.10-1.6 (m, 6H), 1.55-1.50 (m, 2H), 1.79 (s, 3H). $^{13}$C NMR (125 MHz, CDCl$_3$) δ 169.8, 163.4, 161.5, 156.2, 143.6, 142.0, 132.3, 130.8, 129.8, 128.0, 126.1, 124.8, 117.2, 116.2, 115.4, 114.1, 77.2, 70.9, 40.5, 31.8, 28.3, 25.1, 23.3, 18.9.

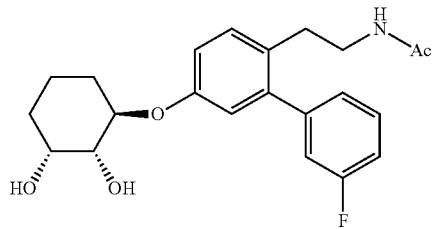 [SMILES: CC(=O)NCCc1ccc(O[C@@H]2CCC[C@@H](O)[C@H]2O)cc1-c1cccc(F)c1]

N-(2-(5-(((1R,2R,3R)-2,3-dihydroxycyclohexyl)oxy)-3'-fluoro-[1,1'-biphenyl]-2-yl)ethyl)acetamide (46)

To a solution of 38 (7 mg, 0.032 mmol) in a mixture of THF/H$_2$O (1:1, 1 mL), catalytic amounts of OsO$_4$ (0.0032 mmol) and NMO (0.048 mmol) were added. The resulting solution was stirred at room temperature overnight. THF was evaporated and the residue extracted with EtOAc. The organic layer was washed with saturated NaHCO$_3$ followed by saturated NH$_4$Cl, dried with Na$_2$SO$_4$, concentrated, and purified (50%-100% EtOAc in hexane) to give 46.

$^1$H NMR (500 MHz, CDCl$_3$) δ 7.34-7.30 (m, 1H), 7.12 (d, J=5 Hz, 1H), 7.02-6.98 (m, 2H), 6.93 (dd, J=5 Hz, 1H), 6.85 (dd, 1H), 6.72 (d, 1H), 5.21 (br, s, 1H), 4.41-4.36 (m, 1H), 4.12 (s, 1H), 3.70-3.67 (m, 1H), 3.21 (q, J=3 Hz, 2H), 2.65 (t, J=3 Hz, 2H), 2.33 (s, 1H), 2.06 (m, 1H), 1.86 (m, 1H), 1.80 (s, 3H), 1.66 (m, 1H), 1.46 (m, 2H), 1.31 (m, 2H). $^{13}$C NMR (125 MHz, CDCl$_3$) δ 169.9, 163.5, 161.5, 156.1, 143.4, 142.2, 130.9, 129.9, 128.8, 124.8, 117.5, 116.2, 115.6, 114.1, 74.6 66.4, 40.5, 31.9, 29.7, 29.6 28.3, 23.3, 18.2.

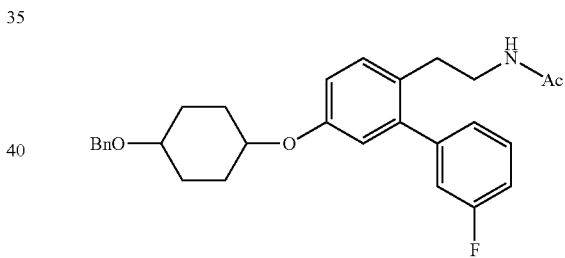

N-(2-(5-((4-(benzyloxy)cyclohexyl)oxy)-3'-fluoro-[1,1'-biphenyl]-2yl)ethyl)acetamide (44)

To a solution of phenol 20 (45 mg, 0.16 mmol) in DMF (1 mL) potassium carbonate (30 mg, 0.19 mmol) was added and stirred at room temperature for 30 min, after which 4-(benzyloxy)cyclohexyl 4-methylbenzenesulfonate (75 mg, 0.19 mmol) and TBAI (7 mg, 0.016 mmol) were added to the solution, and heated to 90° C. overnight. Upon completion, distilled water (5 mL) was added to the mixture and the organic layer extracted into ethyl acetate. After removal of the solvent on a rotary evaporator, the crude mixture was purified by column chromatography (Silica gel, 40% EtOAc in hexane) to give 44 (8 mg) as a white solid.

$^1$H NMR (500 MHz, CDCl$_3$) δ 7.67-7.58 (m, 4H), 7.50-7.46 (m, 2H), 7.41-7.38 (m, 4H), 7.30-7.27 (m, 5H), 7.12 (d, J=5 Hz, 1H), 7.01-6.92 (m, 3H), 6.82-6.79 (dt, J$_1$=10 Hz, J$_2$=5 Hz, 1H), 6.70-6.67 (dd, J$_1$=10 Hz, J$_2$=5 Hz, 1H), 5.24 (s, 1H), 4.48 (s, 2H), 4.25 (m, 1H), 3.44 (m, 1H), 3.33-3.15 (q, J=6.7 Hz, 2H), 2.78-2.66 (t, J=7.2 Hz, 2H), 2.07-1.80 (m, 4H), 1.79 (s, 3H), 1.69-1.61 (m, 2H), 1.50-1.46 (m, 2H). $^{13}$C

NMR (100 MHz, CDCl$_3$) δ 169.8, 163.4, 161.5, 156.1, 155.9, 143.6, 142.0, 139.0, 132.1, 132.0, 131.9 130.8, 129.8, 128.5, 128.4, 128.3, 128.1, 128.0, 127.4, 124.8, 117.5, 116.2, 116.0, 115.6, 115.5, 114.2, 114.1, 114.0, 75.4, 74.5, 74.3, 72.8, 70.1, 69.7, 40.5, 31.8, 30.9, 28.4, 28.3, 27.4, 27.3, 23.3. HRMS (ESI+), m/z [M+Na$^+$] calculated for C$_{29}$H$_{32}$FNO$_3$Na 484.2264; found 484.2249.

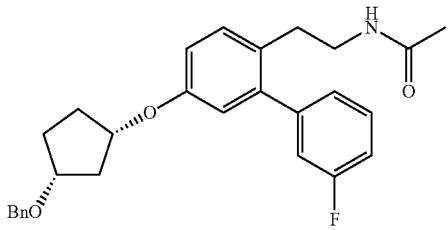 [SMILES: CC(=O)NCCc1ccc(O[C@H]2CC[C@@H](OCc3ccccc3)C2)cc1-c1cccc(F)c1]

N-(2-(5-(((1S,3R)-3-(benzyloxy)cyclopentyl)oxy)-3'-fluoro-[1,1'-biphenyl]-2-yl)ethyl)acetamide (40)

$^1$H NMR (500 MHz, CDCl$_3$) δ 7.39-7.18 (m, 6H), 7.11 (d, J=5 Hz, 1H), 6.98-6.91 (m, 2H), 6.79 (d, J=5 Hz, 1H), 6.66 (s, 1H), 5.30 (br, s, 1H), 4.62 (m, 1H), 4.42 (s, 2H), 3.95 (m, 1H), 3.19 (q, J=3 Hz, 2H), 2.65 (t, J=3 Hz, 2H), 2.27 (dt, J=2.3 Hz, 1H), 1.98-1.95 (m, 1H), 1.92-1.81 (m, 5H), 1.79 (s, 3H). $^{13}$C NMR (125 MHz, CDCl$_3$) δ 169.9, 163.5, 161.5, 156.4, 143.7, 141.9, 138.6, 130.7, 129.8, 128.3, 127.4, 124.8, 117.0, 116.2, 115.1, 113.9, 78.8, 70.9, 40.5, 38.8, 31.8, 30.7, 23.3.

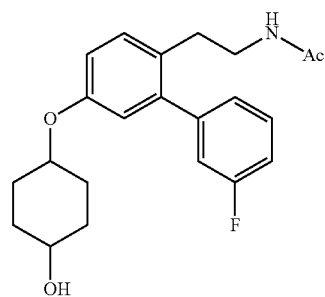 [SMILES: CC(=O)NCCc1ccc(OC2CCC(O)CC2)cc1-c1cccc(F)c1]

N-(2-(3'-fluoro-5-((4-hydroxycyclohexyl)oxy)-[1,1'-biphenyl]-2-yl)ethyl)acetamide (48)

10 mg of 44 was added to a 10 mL round bottom flask containing methanol followed by 10 mol % Pd(OH)$_2$. This was degassed using a hydrogen balloon, for 10 min, and then left stirring at room temperature under a hydrogen atmosphere for 8 h. The reaction was filtered and concentrated to give 48.

$^1$H NMR (500 MHz, CDCl$_3$) δ 7.33-7.29 (m, 1H), 7.12 (d, J=5 Hz, 1H), 7.02-6.98 (m, 3H), 6.80 (dd, J$_1$=10 Hz, J$_2$=5 Hz, 1H), 6.68 (d, J=5 Hz, 1H), 5.19 (br, s, 1H), 4.19 (m, 1H), 3.73 (br, s, 1H), 3.33-3.15 (q, J=6.7 Hz, 2H), 2.76-2.64 (t, J=7.2 Hz, 2H), 2.07-1.94 (m, 4H), 1.80 (s, 3H), 1.43-1.33 (m, 4H). $^{13}$C NMR (100 MHz, CDCl$_3$) δ 169.8, 163.5, 161.5, 156.0, 143.6, 142.0, 130.8, 129.8, 128.2, 124.8, 117.5, 116.2, 116.0, 115.6, 114.2, 74.6, 69.0, 40.5, 31.9, 28.5, 23.3.

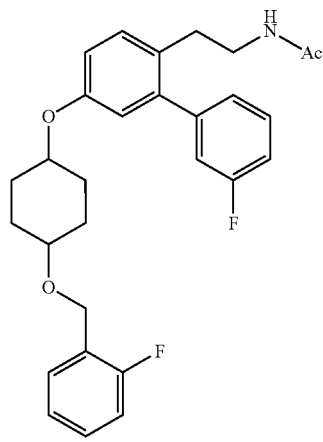 [SMILES: CC(=O)NCCc1ccc(OC2CCC(OCc3ccccc3F)CC2)cc1-c1cccc(F)c1]

N-(2-(3'-fluoro-5-((4-((2-fluorobenzyl)oxy)cyclohexyl)oxy)-[1,1'-biphenyl]-2-yl)ethyl)acetamide (49)

$^1$H NMR (400 MHz, CDCl$_3$) δ 7.50-7.36 (m, 2H), 7.28-7.24 (m, 1H), 7.21-7.13 (m, 2H), 7.09-7.00 (m, 4H), 6.91-6.76 (m, 2H), 5.32 (br, s, 1H), 4.62 (s, 2H), 4.38-4.36 (m, 1H), 4.32-4.31 (m, 1H, minor diast.), 3.56-3.52 (m, 1H), 3.27 (q, J=5 Hz, 2H), 2.75-2.71 (t, J=7.2 Hz, 2H), 2.14-1.89 (m, 4H), 1.87 (s, 3H), 1.76-1.53 (m, 4H). $^{13}$C NMR (100 MHz, CDCl$_3$) δ 170.1, 163.7, 161.8, 159.8, 156.2, 143.9, 142.3, 131.0, 130.6, 130.0, 129.4, 129.2, 126.4, 126.2, 125.1, 124.3, 117.8, 116.4, 115.9, 115.7, 115.2, 114.4, 114.2, 76.0, 75.1, 74.6, 73.1, 63.9, 63.5, 40.7, 32.1, 28.5, 27.6, 23.5.

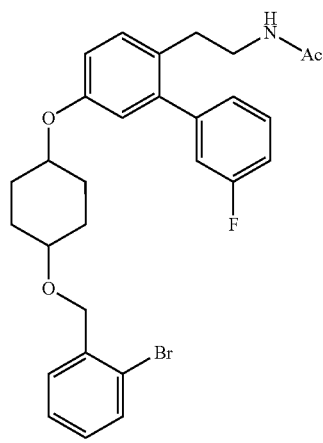 [SMILES: CC(=O)NCCc1ccc(OC2CCC(OCc3ccccc3Br)CC2)cc1-c1cccc(F)c1]

N-(2-(5-((4-((2-bromobenzyl)oxy)cyclohexyl)oxy)-3'-fluoro-[1,1'-biphenyl]-2-yl)ethyl)acetamide (50)

$^1$H NMR (500 MHz, CDCl$_3$) δ 7.57-7.47 (m, 2H), 7.42-7.30 (m, 2H), 7.21-7.12 (m, 2H), 7.10-7.00 (m, 3H), 6.91-6.88 (m, 1H), 6.78-6.76 (m, 1H), 5.33 (br, s, 1H), 4.60 (s, 2H), 4.39-4.33 (m, 1H), 3.60-3.56 (m, 1H), 3.29 (q, J=5 Hz, 2H), 2.74 (t, J=5 Hz, 2H), 2.15-1.92 (m, 4H), 1.88 (s, 3H), 1.78-1.56 (m, 4H).

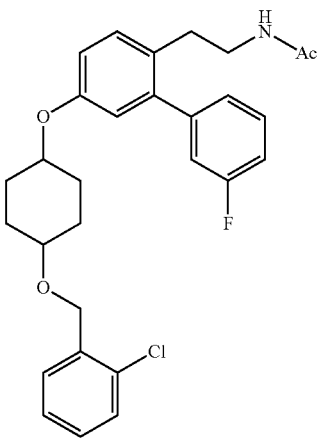 [SMILES: CC(=O)NCCc1ccc(OC2CCC(OCc3ccccc3Cl)CC2)cc1-c1cccc(F)c1]

N-(2-(5-((4-((2-chlorobenzyl)oxy)cyclohexyl)oxy)-3'-fluoro-[1,1'-biphenyl]-2-yl)ethyl)acetamide (51)

¹H NMR (500 MHz, CDCl₃) δ 7.57-7.51 (m, 1H), 7.14-7.34 (m, 2H), 7.30-7.26 (m, 1H), 7.24-7.19 (m, 2H), 7.09-7.00 (m, 3H), 6.91-6.88 (m, 1H), 6.78-6.6.76 (m, 1H), 5.31 (br, s, 1H), 4.64 (s, 2H), 4.39-4.32 (m, 1H), 3.59-3.56 (m, 1H), 3.27 (q, J=5 Hz, 2H), 2.74 (t, J=5 Hz, 2H), 2.16-1.92 (m, 4H), 1.88 (s, 3H), 1.78-1.55 (m, 4H). ¹³C NMR (125 MHz, CDCl₃) δ 170.13, 163.77, 161.80, 156.38, 142.35, 137.02, 132.99, 131.10, 130.16, 130.09, 129.48, 129.39, 129.07, 128.67, 128.33, 127.06, 125.15, 117.83, 116.48, 115.92, 114.48, 114.28, 76.30, 75.39, 74.66, 73.23, 67.25, 40.79, 32.15, 27.77, 23.58.

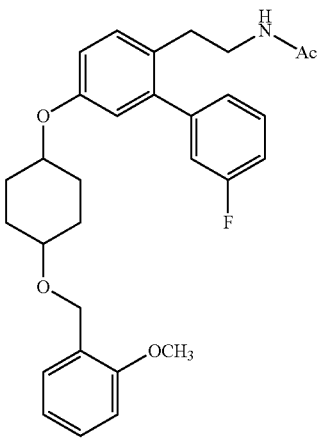 [SMILES: COc1ccccc1COC1CCC(Oc2ccc(CCNC(C)=O)c(-c3cccc(F)c3)c2)CC1]

N-(2-(3'-fluoro-5-((4-((2-methoxybenzyl)oxy)cyclohexyl)oxy)-[1,1'-biphenyl]-2-yl)ethyl)acetamide (52)

¹H NMR (400 MHz, CDCl₃) δ 7.33 (tt, J=14.7, 7.3 Hz, 3H), 7.23-7.06 (m, 3H), 7.04-6.85 (m, 6H), 6.79 (dd, J=8.0, 5.7 Hz, 2H), 6.69 (dd, J=5.3, 2.2 Hz, 1H), 5.23 (t, J=5.5 Hz, 1H), 4.51 (s, 2H), 4.31-4.17 (m, 1H), 3.75 (s, 3H), 3.45 (td, J=7.9, 7.2, 3.5 Hz, 1H), 3.19 (d, J=6.7 Hz, 2H), 2.65 (t, J=7.1 Hz, 3H), 2.04 (t, J=4.1 Hz, 2H), 1.90 (ddd, J=28.1, 12.7, 6.2 Hz, 1H), 1.79 (s, 3H), 1.67-1.58 (m, 2H), 1.55-1.41 (m, 3H). ¹³C NMR (126 MHz, CDCl₃) δ 168.92, 162.45, 160.49, 155.11, 142.58, 141.00, 129.76, 128.84, 128.78, 127.41, 127.19, 127.02, 126.89, 126.36, 123.81, 119.42, 116.53, 115.16, 114.46, 112.99, 109.04, 74.57, 73.58, 63.86, 54.26, 39.52, 30.81, 27.44, 26.43, 22.19.

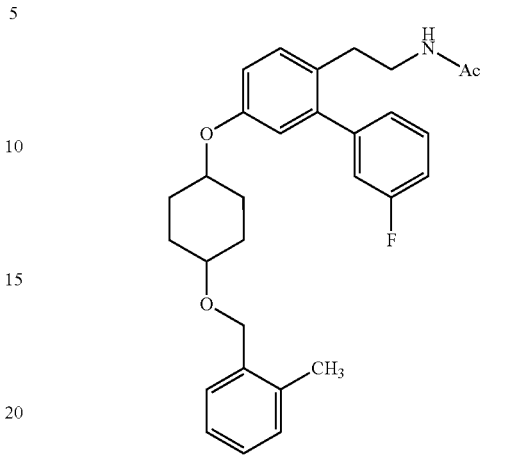

N-(2-(3'-fluoro-5-((4-((2-methylbenzyl)oxy)cyclohexyl)oxy)-[1,1'-biphenyl]-2-yl)ethyl)acetamide (53)

¹H NMR (400 MHz, CDCl₃) δ 7.46-7.28 (m, 2H), 7.20 (tq, J=6.8, 4.1, 3.1 Hz, 4H), 7.13-7.01 (m, 3H), 6.90 (dt, J=8.5, 3.0 Hz, 1H), 6.78 (dd, J=4.7, 2.7 Hz, 1H), 5.29 (s, 1H), 4.55 (s, 2H), 4.42-4.28 (m, 1H), 3.54 (dq, J=7.8, 3.8 Hz, 1H), 3.29 (q, J=6.7 Hz, 2H), 2.75 (t, J=7.2 Hz, 2H), 2.37 (d, J=1.9 Hz, 3H), 2.13 (q, J=2.9, 2.5 Hz, 1H), 2.04-1.93 (m, OH), 1.89 (s, 3H), 1.74 (dt, J=8.7, 4.6 Hz, 2H).

N-(2-(5-((4-((3-bromobenzyl)oxy)cyclohexyl)oxy)-3'-fluoro-[1,1'-biphenyl]-2-yl)ethyl)acetamide (54)

¹H NMR (500 MHz, CDCl₃) δ 7.53-7.51 (m, 1H), 7.43-7.36 (m, 2H), 7.30-7.26 (m, 1H), 7.23-7.19 (m, 2H), 7.10-7.05 (m, 2H), 7.03-6.99 (m, 1H), 6.91-6.86 (m, 1H), 6.79-6.76 (m, 1H), 5.30 (br, s, 1H), 4.52 (s, 2H), 4.39-4.29 (m, 1H), 3.53-3.49 (m, 1H), 3.29 (q, J=5 Hz, 2H), 2.74 (t, J=5 Hz, 2H), 2.15-1.87 (m, 4H), 1.87 (s, 3H), 1.67-1.44 (m, 4H). ¹³C NMR (125 MHz, CDCl₃) δ 170.12, 163.77, 156.35, 156.16, 143.92, 141.70, 131.10, 130.77, 130.72, 130.62, 130.22, 130.10, 128.45, 127.81, 126.14, 125.15, 117.84, 116.48, 115.91, 69.63, 69.24, 40.79, 32.15, 28.46, 27.74, 27.59, 23.58.

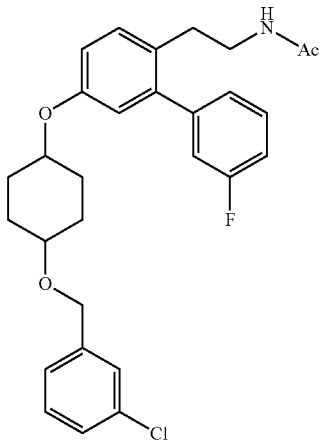 [SMILES: CC(=O)NCCc1ccc(OC2CCC(OCc3cccc(Cl)c3)CC2)cc1-c1cccc(F)c1]

N-(2-(5-((4-((3-chlorobenzyl)oxy)cyclohexyl)oxy)-3'-fluoro-[1,1'-biphenyl]-2-yl)ethyl)acetamide (55)

$^1$H NMR (500 MHz, CDCl$_3$) δ 7.41-7.36 (m, 2H), 7.29-7.19 (m 4H), 7.07-7.00 (m, 3H), 6.91-6.87 (m, 1H), 6.78-6.76 (m, 1H), 5.31 (br, s, 1H), 4.53 (s, 2H), 4.39-4.36 (m, 1H), 3.53-3.49 (m, 1H), 3.28 (q, J=5 Hz, 2H), 2.73 (t, J=5 Hz, 2H), 2.14-2.1.87 (m, 4H), 1.87 (s, 3H), 1.75-1.52 (m, 4H). $^{13}$C NMR (125 MHz, CDCl$_3$) δ 170.10, 163.76, 161.80, 156.34, 143.92, 142.34, 141.42, 134.56, 131.09, 130.16, 129.91, 128.46, 128.36, 127.78, 127.69, 125.64, 125.14, 117.83, 116.47, 115.90, 114.47, 114.31, 75.98, 74.62, 69.68, 40.78, 32.15, 28.55, 27.73, 23.57.

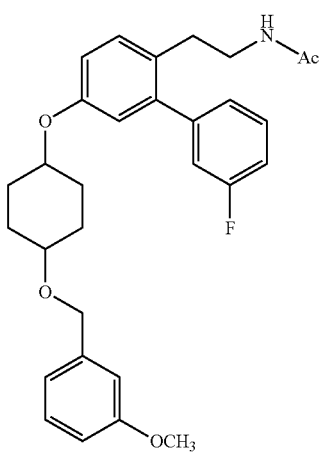 [SMILES: COc1cccc(COC2CCC(Oc3ccc(CCNC(C)=O)c(-c4cccc(F)c4)c3)CC2)c1]

N-(2-(3'-fluoro-5-((4-((3-methoxybenzyl)oxy)cyclohexyl)oxy)-[1,1'-biphenyl]-2-yl)ethyl)acetamide (56)

$^1$H NMR (500 MHz, CDCl$_3$) δ 7.41-7.36 (m, 1H), 7.28-7.25 (m, 1H), 7.10 (d, J=5 Hz, 1H), 7.09-7.00 (m, 3H), 6.95-6.87 (m, 3H), 6.84-6.81 (m, 1H), 6.78-6.75 (m, 1H), 5.35 (br, s, 1H), 4.54 (s, 2H), 4.37-4.30 (m, 1H), 3.82 (s, 3H), 3.53-3.49 (m, 1H), 3.28 (q, J=5 Hz, 2H), 2.73 (t, J=5 Hz, 2H), 2.14-1.88 (m, 4H), 1.88 (s, 3H), 1.78-1.51 (m, 4H).

$^{13}$C NMR (125 MHz, CDCl$_3$) δ 170.18, 163.76, 161.80, 159.98, 156.38, 143.93, 143.88, 142.33, 140.96, 131.08, 130.16, 129.67, 128.40, 125.14, 119.97, 117.83, 116.47, 115.78, 114.47, 114.30, 113.17, 75.66, 74.77, 70.29, 55.49, 40.80, 32.13, 28.58, 27.71, 27.62, 23.54.

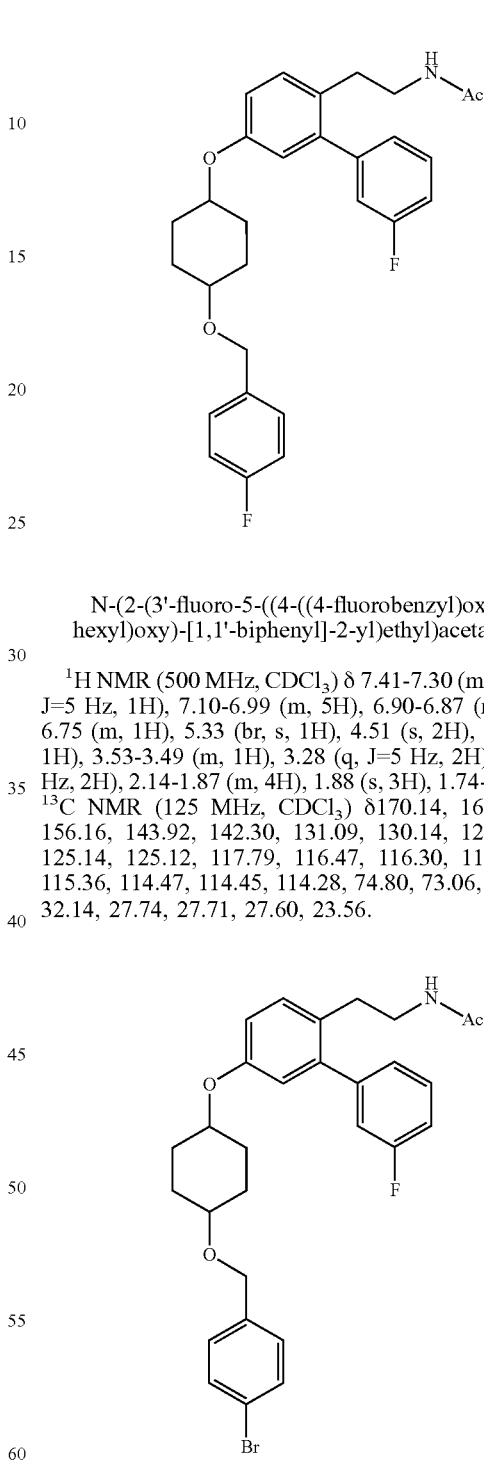

N-(2-(3'-fluoro-5-((4-((4-fluorobenzyl)oxy)cyclohexyl)oxy)-[1,1'-biphenyl]-2-yl)ethyl)acetamide (57)

$^1$H NMR (500 MHz, CDCl$_3$) δ 7.41-7.30 (m, 3H), 7.20 (d, J=5 Hz, 1H), 7.10-6.99 (m, 5H), 6.90-6.87 (m, 1H), 6.78-6.75 (m, 1H), 5.33 (br, s, 1H), 4.51 (s, 2H), 4.39-4.29 (m, 1H), 3.53-3.49 (m, 1H), 3.28 (q, J=5 Hz, 2H), 2.73 (t, J=5 Hz, 2H), 2.14-1.87 (m, 4H), 1.88 (s, 3H), 1.74-1.48 (m, 4H). $^{13}$C NMR (125 MHz, CDCl$_3$) δ170.14, 163.76, 161.79, 156.16, 143.92, 142.30, 131.09, 130.14, 129.47, 128.34, 125.14, 125.12, 117.79, 116.47, 116.30, 115.91, 115.53, 115.36, 114.47, 114.28, 74.80, 73.06, 69.37, 40.79, 32.14, 27.74, 27.71, 27.60, 23.56.

N-(2-(5-((4-((4-bromobenzyl)oxy)cyclohexyl)oxy)-3'-fluoro-[1,1'-biphenyl]-2-yl)ethyl)acetamide (58)

$^1$H NMR (500 MHz, CDCl$_3$) δ 7.49-7.46 (m, 2H), 7.41-7.36 (m, 1H), 7.26-7.19 (m, 3H) 7.09-6.99 (m, 3H), 6.09-

6.87 (m, 1H), 6.77 (dd, J₁=10 Hz, J₂=5 Hz, 1H), 5.30 (br, s, 1H), 4.50 (s, 2H), 4.38-4.36 (m, 1H), 4.35-4.30 (m, 1H), 3.52-3.48 (m, 1H), 3.28 (q, J=3 Hz, 2H), 2.73 (t, J=3 Hz, 2H), 2.13-1.88 (m, 4H), 1.87 (s, 3H). 1.73-1.67 (m, 2H), 1.59-1.51 (m, 2H), ¹³C NMR (125 MHz, CDCl₃) δ 170.09, 163.76, 161.80, 156.34, 143.87, 142.32, 138.30, 131.73, 131.09, 130.14, 129.35, 128.46, 125.14, 121.53, 117.82, 116.47, 116.30, 115.90, 115.77, 114.48, 75.86, 74.90, 74.64, 73.05, 69.71, 69.31, 40.78, 32.15, 28.58, 27.73, 23.57.

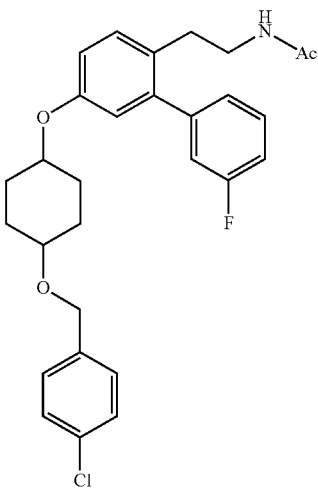 [SMILES: CC(=O)NCCc1ccc(OC2CCC(OCc3ccc(Cl)cc3)CC2)cc1-c1cccc(F)c1]

N-(2-(5-((4-((4-chlorobenzyl)oxy)cyclohexyl)oxy)-3'-fluoro-[1,1'-biphenyl]-2-yl)ethyl)acetamide (59)

¹H NMR (500 MHz, CDCl₃) δ 7.37-7.32 (m, 1H), 7.29-7.22 (m, 4H), 7.16 (d, J=5 Hz, 1H), 7.05-6.95 (m, 3H), 6.86-6.83 (m, 1H), 6.73-6.71 (m, 1H), 5.33 (br, s, 1H), 4.49 (s, 2H), 4.35-4.26 (m, 1H), 3.49-3.44 (m, 1H), 3.24 (q, J=5 Hz, 2H), 2.71 (t, J=5 Hz, 2H), 2.09-1.81 (m, 4H), 1.84 (s, 3H), 1.71-1.63 (m, 2H), 1.57-1.46 (m, 2H). ¹³C NMR (125 MHz, CDCl₃) δ 170.15, 163.75, 161.79, 156.33, 143.91, 142.32, 137.79, 133.42, 131.07, 130.15, 129.01, 128.85, 128.78, 128.45, 125.14, 117.82, 116.46, 115.89, 114.47, 75.84, 74.89, 74.65, 73.05, 69.68, 69.28, 40.80, 32.14, 27.73, 23.53.

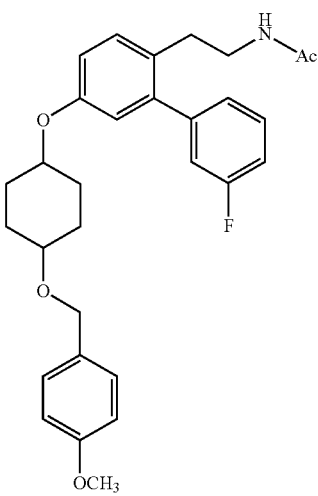 [SMILES: COc1ccc(COC2CCC(Oc3ccc(CCNC(C)=O)c(-c4cccc(F)c4)c3)CC2)cc1]

N-(2-(3'-fluoro-5-((4-((4-methoxybenzyl)oxy)cyclohexyl)oxy)-[1,1'-biphenyl]-2-yl)ethyl)acetamide (60)

¹H NMR (500 MHz, CDCl₃) δ 7.61-7.51 (m, 2H), 7.49-7.46 (m, 2H), 7.41-7.35 (m, 1H), 7.20 (d, J=5 Hz, 1H), 7.09-6.99 (m, 3H), 6.91-6.87 (m, 1H), 6.77-6.75 (m, 1H), 5.38 (br, s, 1H), 4.61 (s, 2H), 4.37-4.31 (m, 1H), 3.83 (s, 3H), 3.55-3.51 (m, 1H), 3.28 (q, J=5 Hz, 2H), 2.73 (t, J=5 Hz, 2H), 2.15-1.86 (m, 4H), 1.87 (s, 3H), 1.75-1.53 (m, 4H). ¹³C NMR (125 MHz, CDCl₃) δ 170.21, 163.77, 161.80, 159.34, 156.40, 143.88, 142.33, 131.08, 130.16, 129.34, 128.37, 125.14, 117.84, 116.48, 116.31, 115.78, 114.31, 114.07, 75.39, 74.85, 70.11, 55.57, 40.83, 32.13, 28.75, 23.52.

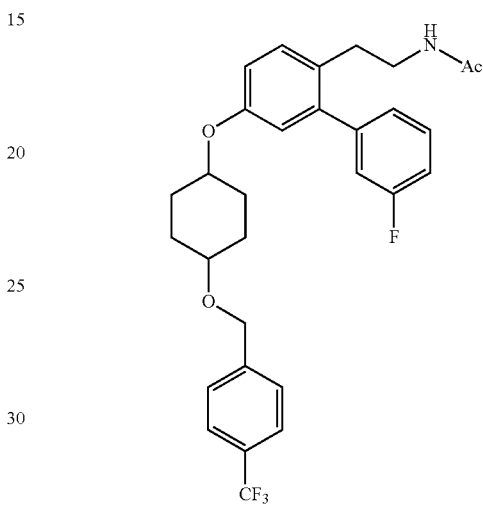

N-(2-(3'-fluoro-5-((4-((4-(trifluoromethyl)benzyl)oxy)cyclohexyl)oxy)-[1,1'-biphenyl]-2-yl)ethyl)acetamide (62)

¹H NMR (500 MHz, CDCl₃) δ 7.61 (d, J=5 Hz, 2H), 7.48 (t, J=5 Hz, 2H), 7.42-7.37 (m, 1H), 7.20 (d, J=5 Hz, 1H), 7.09 (d, J=5 Hz, 1H), 7.09-7.00 (m, 2H), 6.92-6.86 (m, 1H), 6.80-6.75 (m, 1H), 5.38 (br, s, 1H), 4.61 (s, 2H), 4.40-4.30 (m, 1H), 3.55-3.50 (m, 1H), 3.29 (q, J=3 Hz, 2H), 2.74 (t, J=3 Hz, 2H), 2.15-1.87 (m, 4H), 1.88 (s, 3H), 1.77-1.52 (m, 4H). ¹³C NMR (125 MHz, CDCl₃) δ 170.21, 163.77, 161.81, 156.34, 156.16, 143.91, 143.44, 142.35, 131.11, 130.17, 128.45, 128.36, 127.62, 125.63, 125.14, 117.82, 116.47, 115.90, 114.50, 76.11, 74.56, 69.68, 69.30, 40.84, 32.15, 28.52, 28.41, 27.73, 27.61, 23.53.

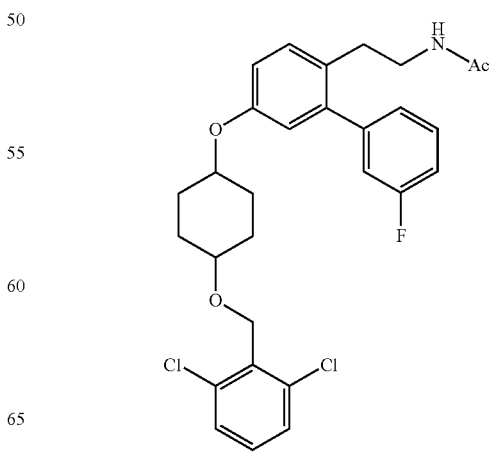

N-(2-(5-((4-((2,6-dichlorobenzyl)oxy)cyclohexyl)oxy)-3'-fluoro-[1,1'-biphenyl]-2-yl)ethyl)acetamide (64)

¹H NMR (500 MHz, CDCl₃) δ 7.41-7.36 (m, 1H), 7.33-7.31 (m, 1H), 7.20-7.16 (m, 2H) 7.09-6.99 (m, 3H), 6.90-6.87 (m, 1H), 6.78-6.76 (m, 1H), 5.29 (br, s, 1H), 4.77 (s, 2H), 4.38-4.35 (m, 1H), 4.33-4.28 (m, 1H), 3.61-3.56 (m, 1H), 3.27 (q, J=3 Hz, 2H), 2.73 (t, J=3 Hz, 2H), 2.16-1.89 (m, 4H), 1.87 (s, 3H). 1.78-1.67 (m, 2H), 1.63-1.51 (m, 2H), ¹³C NMR (125 MHz, CDCl₃) δ 170.08, 163.76, 161.80, 156.39, 143.89, 137.09, 134.08, 131.08, 130.13, 128.70, 125.15, 117.82, 117.79, 116.47, 115.76, 114.46, 114.30, 77.55, 77.50, 77.30, 77.05, 76.51, 74.71, 65.36, 40.77, 32.15, 28.59, 27.79, 23.58.

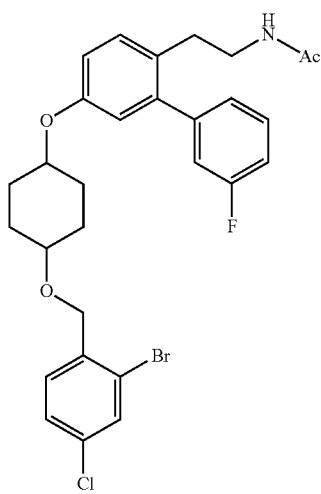

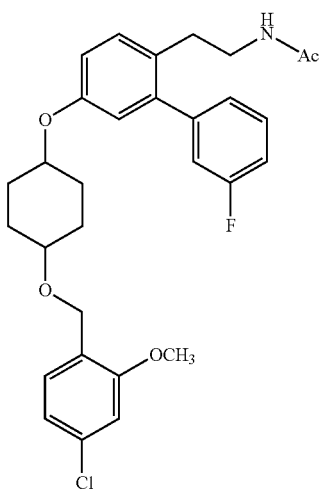 [SMILES: COc1cc(Cl)ccc1COC1CCC(Oc2ccc(CCNC(C)=O)c(-c3cccc(F)c3)c2)CC1]

N-(2-(5-((4-((4-chloro-2-methoxybenzyl)oxy)cyclohexyl)oxy)-3'-fluoro-[1,1'-biphenyl]-2-yl)ethyl)acetamide (65)

¹H NMR (500 MHz, CDCl₃) δ 7.41-7.31 (m, 2H), 7.21-7.19 (m, 1H), 7.10-7.05 (m, 2H), 7.03-7.00 (m, 1H), 6.97-6.94 (m, 1H), 6.90-6.87 (m, 1H), 6.85-6.84 (m, 1H), 6.78-6.76 (m, 1H), 5.27 (br, s, 1H), 4.53 (s, 2H), 4.38-4.29 (m, 1H), 3.82 (s, 3H), 3.53-3.49 (m, 1H), 3.29 (q, J=5 Hz, 2H), 2.73 (t, J=5 Hz, 2H), 2.15-1.87 (m, 4H), 1.88 (s, 3H), 1.75-1.49 (m, 4H). ¹³C NMR (125 MHz, CDCl₃) δ 131.10, 131.07, 129.49, 120.72, 117.83, 116.49, 116.32, 115.92, 115.78, 111.13, 64.74, 55.83, 40.79, 32.16, 27.77, 23.59.

N-(2-(5-((4-((2-bromo-4-chlorobenzyl)oxy)cyclohexyl)oxy)-3'-fluoro-[1,1'-biphenyl]-2-yl)ethyl)acetamide (66)

¹H NMR (500 MHz, CDCl₃) δ 7.56-7.54 (m, 1H), 7.50-7.44 (m, 1H), 7.41-7.36 (m, 1H), 7.32-7.30 (m, 1H), 7.21-7.19 (m, 1H), 7.09-7.00 (m, 3H), 6.91-6.87 (m, 1H), 6.78-6.76 (m, 1H), 5.30 (br, s, 1H), 4.55 (s, 2H), 4.38-4.32 (m, 1H), 3.59-3.55 (m, 1H), 3.29 (q, J=5 Hz, 2H), 2.74 (t, J=5 Hz, 2H), 2.15-1.88 (m, 4H), 1.88 (s, 3H), 1.77-1.55 (m, 4H). ¹³C NMR (125 MHz, CDCl₃) δ 170.09, 163.76, 161.80, 156.33, 143.91, 142.35, 137.27, 133.86, 132.26, 132.16, 131.10, 130.16, 129.93, 128.47, 127.90, 125.14, 122.87, 117.81, 116.47, 116.30, 115.89, 115.76, 114.48, 76.44, 69.34, 40.78, 32.16, 28.49, 28.38, 27.75, 27.69, 23.58.

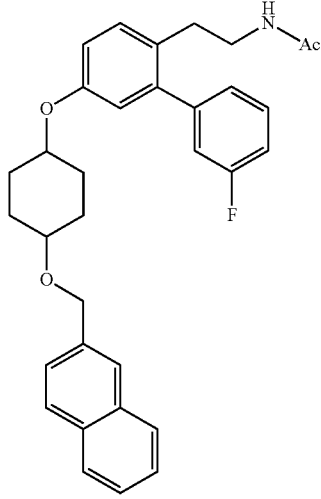 [SMILES: CC(=O)NCCc1ccc(OC2CCC(OCc3ccc4ccccc4c3)CC2)cc1-c1cccc(F)c1]

N-(2-(3'-fluoro-5-((4-(naphthalen-2-ylmethoxy)cyclohexyl)oxy)-[1,1'-biphenyl]-2-yl)ethyl)acetamide (67)

¹H NMR (500 MHz, CDCl₃) δ 7.86-7.80 (m, 4H), 7.51-7.46 (m, 3H), 7.41-7.37 (m, 1H), 7.21 (d, J=5 Hz, 1H), 7.09-7.00 (m, 3H), 6.91-6.87 (m, 1H), 6.79-6.76 (m, 1H), 5.31 (br, s, 1H), 4.73 (s, 2H), 4.39-4.31 (m, 1H), 3.58-3.55 (m, 1H), 3.29 (q, J=5 Hz, 2H), 2.74 (t, J=5 Hz, 2H), 2.17-1.89 (m, 4H), 1.88 (s, 3H), 1.77-1.55 (m, 4H). $^{13}$C NMR (125 MHz, CDCl$_3$) δ 170.12, 163.76, 161.80, 156.37, 142.33, 136.77, 133.57, 133.17, 131.08, 130.15, 128.41, 128.10, 127.96, 126.34, 126.00, 125.14, 117.83, 116.47, 115.78, 114.47, 114.30, 114.27, 77.50, 75.70, 74.78, 70.58, 70.17, 40.78, 32.14, 28.73, 27.78, 27.66, 23.57.

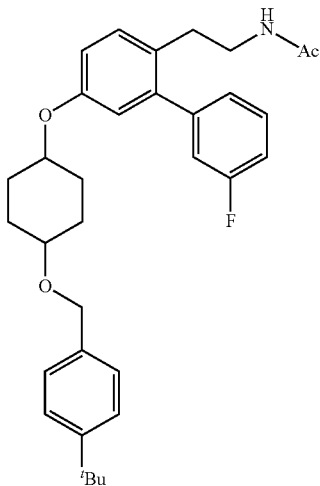 [SMILES: CC(=O)NCCc1ccc(OC2CCC(OCc3ccc(C(C)(C)C)cc3)CC2)cc1-c1cccc(F)c1]

N-(2-(5-((4-((4-(tert-butyl)benzyl)oxy)cyclohexyl) oxy)-3'-fluoro-[1,1'-biphenyl]-2-yl)ethyl)acetamide (63)

$^1$H NMR (500 MHz, CDCl$_3$) δ 7.40-7.36 (m, 3H), 7.31-7.27 (m, 2H), 7.20 (d, J=5 Hz, 1H), 7.09-6.99 (m, 3H), 6.91-6.87 (m, 1H), 6.78-6.76 (m, 1H), 5.30 (br, s, 1H), 4.53 (s, 2H), 4.38-4.30 (m, 1H), 3.54-3.51 (m, 1H), 3.29 (q, J=5 Hz, 2H), 2.74 (t, J=5 Hz, 2H), 2.14-1.88 (m 4H), 1.88 (s, 3H), 1.75-1.51 (m, 4H), 1.32 (s, 9H).

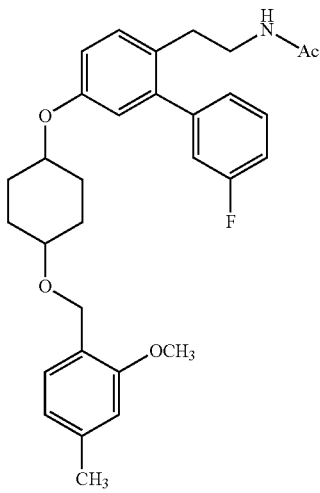 [SMILES: COc1cc(C)ccc1COC1CCC(Oc2ccc(CCNC(C)=O)c(-c3cccc(F)c3)c2)CC1]

N-(2-(3'-fluoro-5-((4-((2-methoxy-4-methylbenzyl) oxy)cyclohexyl)oxy)-[1,1'-biphenyl]-2-yl)ethyl)acetamide (68)

$^1$H NMR (500 MHz, CDCl$_3$) δ 7.41-7.36 (m, 1H), 7.31-7.26 (m, 1H), 7.20-7.18 (m, 1H), 7.10-7.05 (m, 2H), 7.03-7.00 (m, 1H), 6.90-6.87 (m, 1H), 6.79-6.76 (m, 2H), 6.69-6.68 (m, 1H), 5.28 (br, s, 1H), 4.55 (s, 2H), 4.37-4.28 (m, 1H), 3.83 (s, 3H), 3.54-3.48 (m, 1H), 3.28 (q, J=5 Hz, 2H), 2.73 (t, J=5 Hz, 2H), 2.35 (s, 3H), 2.14-1.89 (m, 4H), 1.88 (s, 3H), 1.75-1.48 (m, 4H). $^{13}$C NMR (125 MHz, CDCl$_3$) δ 170.10, 163.77, 161.80, 157.19, 156.43, 143.91, 142.33, 138.79, 131.07, 130.15, 128.94, 128.36, 125.15, 124.57, 121.28, 117.84, 116.48, 116.31, 115.94, 115.77, 114.46, 114.43, 111.47, 74.96, 65.07, 55.57, 40.77, 32.14, 28.80, 27.78, 23.59, 21.88.

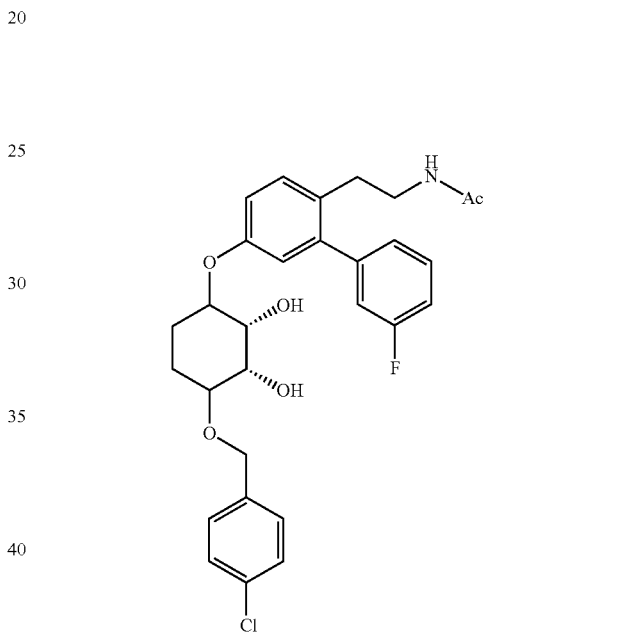

N-(2-(5-(((2R,3S)-4-((4-chlorobenzyl)oxy)-2,3-dihydroxycyclohexyl)oxy)-3'-fluoro-[1,1'-biphenyl]-2-yl)ethyl)acetamide (75)

$^1$H NMR (500 MHz, CDCl$_3$) δ 7.41-7.27 (m, 6H), 7.20 (d, J=5 Hz, 1H), 7.10-7.06 (m, 2H), 7.01-6.99 (m, 1H), 6.92-6.90 (m, 1H), 6.79 (d, J=3, 1H), 5.29 (br, s, 1H), 4.62 (dd, J$_1$=3 Hz, J$_2$=7.5 Hz, 2H), 4.53-4.50 (m, 1H), 4.17-4.15 (m, 1H), 4.06-4.04 (m, 1H), 3.72-3.69 (m, 1H), 3.28 (q, J=3 Hz, 2H), 2.74 (t, J=3 Hz, 2H), 2.64 (d, J=3 Hz, 2H), 1.94-1.72 (m, 4H), 1.88 (s, 3H). $^{13}$C NMR (125 MHz, CDCl$_3$) δ 170.13, 163.78, 161.81, 156.01, 143.65, 142.49, 137.12, 133.77, 130.22, 129.17, 128.92, 125.11, 117.72, 116.45, 116.28, 115.75, 114.59, 114.42, 75.83, 72.12, 71.46, 70.52, 40.76, 23.59, 23.45.

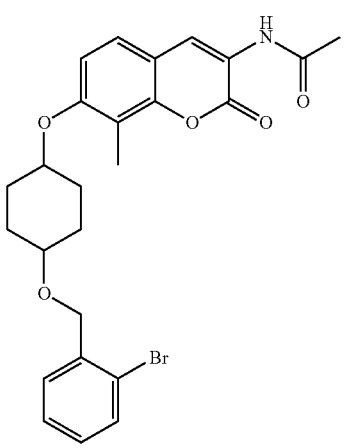 [SMILES: CC(=O)Nc1cc2ccc(OC3CCC(OCc4ccccc4Br)CC3)c(C)c2oc1=O]

N-(7-((4-((2-bromobenzyl)oxy)cyclohexyl)oxy)-8-methyl-2-oxo-2H-chromen-3-yl)acetamide (79)

$^1$H NMR (500 MHz, CDCl$_3$) δ 8.62 (s, 1H), 7.99 (s, 1H), 7.58-7.52 (m, 2H), 7.36-7.28 (m, 2H), 7.18-7.13 (m, 1H), 6.90-6.87 (m, 1H), 4.62 (s, 2H), 4.52-4.46 (m, 1H), 3.61-3.56 (m, 1H), 2.35 (s, 3H), 2.24 (s, 3H), 2.18-2.05 (m, 2H), 1.97-1.91 (m, 2H), 1.85-1.62 (m, 4H). $^{13}$C NMR (125 MHz, CDCl$_3$) δ 169.45, 159.58, 157.40, 149.74, 138.48, 132.76, 129.27, 129.05, 127.70, 125.68, 124.81, 122.82, 121.43, 115.50, 113.31, 110.65, 75.63, 69.67, 28.01, 27.74, 25.02, 8.63.

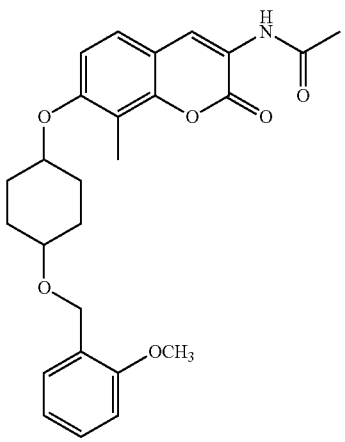 [SMILES: COc1ccccc1COC1CCC(Oc2ccc3cc(NC(C)=O)c(=O)oc3c2C)CC1]

N-(7-((4-((2-methoxybenzyl)oxy)cyclohexyl)oxy)-8-methyl-2-oxo-2H-chromen-3-yl)acetamide (80)

$^1$H NMR (500 MHz, CDCl$_3$) δ 8.62 (s, 1H), 8.00 (s, 1H), 7.38-7.35 (m, 2H), 7.30-7.27 (m, 2H), 7.23-7.17 (m, 1H), 6.89-6.86 (m, 1H), 4.56 (s, 2H), 4.51-4.48 (m, 1H), 3.54-3.51 (m, 1H), 2.37 (s, 3H), 2.33 (s, 3H), 2.24 (s, 3H), 2.12-2.03 (m, 2H), 1.95-1.87 (m, 2H), 1.82-1.63 (m, 4H). $^{13}$C NMR (125 MHz, CDCl$_3$) δ 169.46, 159.57, 157.39, 149.73, 136.91, 130.50, 128.71, 128.00, 126.10, 125.66, 124.81, 121.41, 115.50, 113.27, 110.62, 75.37, 73.68, 28.02, 27.67, 25.00, 19.16, 8.59.

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Baylon, et al., J. Org. Chem., 12:121, 1999.
Beaver, et al., J. Am. Chem. Soc., 130:2082-2086, 2008.
Brand and Nicholls, Biochem. J., 435:297, 2011.
Burlison, et al., J. Am. Chem. Soc., 128:15529, 2006.
Burlison and Blagg, J. Org. Chem., 8:4855, 2006.
Burlison, et al., J. Org. Chem., 73:2130, 2008.
Chowdhury, et al., Brain, 135:1751, 2012.
Cohen, et al., Ann. Surg. Oncol., 19(Suppl. 3):S483, 2012.
Donnelly, et al., J. Org. Chem., 2008, 73:8901.
Handbook of Pharmaceutical Salts: Properties, and Use, Stahl and Wermuth Eds.), Verlag Helvetica Chimica Acta, 2002.
Harbauer, et al., Cell Metabolism, 19(3):357-372, 2014.
Kusuma, et al., J. Med. Chem., 55:5797, 2012.
Ma, et al., J. Pharmacol. Exp. Ther., 348:281-292, 2014.
March's Advanced Organic Chemistry: Reactions, Mechanisms, and Structure, 2007.
Marcu, et al., J. Natl. Cancer Inst., 92:242-248, 2000.
Shelton, et al., Mol. Pharmacol., 76:1314, 2009.
Strejan et al., J. Neuroimmunol., 7:27, 1984.
Urban, et al., ASN Neuro., 2:189-199, 2010.
Yu, et al., J. Am. Chem. Soc., 127:12778, 2005a.
Yu, et al., J. Org. Chem., 70:5599-5605, 2005b.
Yun, et al., Biochemistry, 43:8217-8229, 2004.
Zhao and Blagg, In: Inhibitors of Molecular Chaperones As Therapeutic Agents, Ed: Timothy Machajewski, RSC Publishing: London, 2014.
Zhao, et al., J. Med. Chem., 54:3839-3853, 2011.

What is claimed is:

1. A pharmaceutical composition comprising:
(A) a compound of the formula:

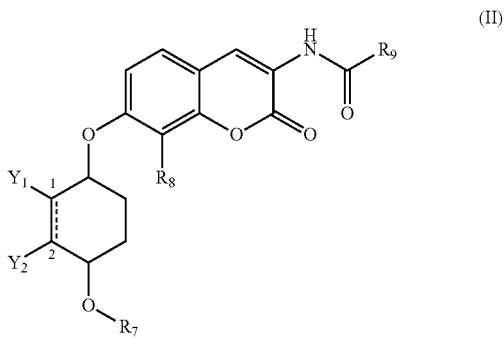

wherein:
R₇ is aryl$_{(C \leq 12)}$, aralkyl$_{(C \leq 12)}$, or a substituted version of either of these groups;
R₈ is hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$;
R₉ is alkyl$_{(C \leq 12)}$, cycloalkyl$_{(C \leq 12)}$, aryl$_{(C \leq 12)}$, heteroaryl$_{(C \leq 12)}$, or a substituted version of any of these groups; and
Y₁ and Y₂ are each independently hydrogen or hydroxy; and
(B) an excipient; wherein the pharmaceutical composition has been formulated as a unit dose.

2. The pharmaceutical composition of claim 1, wherein the bond between atom 1 and atom 2 in formula II is a single bond.

3. The pharmaceutical composition of claim 1, wherein the bond between atom 1 and atom 2 in formula II is a double bond.

4. The pharmaceutical composition of claim 1, wherein Y₁ is hydrogen.

5. The pharmaceutical composition of claim 1, wherein Y₁ is hydroxy.

6. The pharmaceutical composition of claim 1, wherein Y₂ is hydrogen.

7. The pharmaceutical composition of claim 1, wherein Y₂ is hydroxy.

8. The pharmaceutical composition of claim 1, wherein R₈ is alkyl$_{(C \leq 12)}$.

9. The pharmaceutical composition of claim 8, wherein R₈ is methyl.

10. The pharmaceutical composition of claim 1, wherein R₉ is alkyl$_{(C \leq 12)}$.

11. The pharmaceutical composition of claim 10, wherein R₉ is methyl.

12. The pharmaceutical composition of claim 1, wherein R₇ is aralkyl$_{(C \leq 12)}$ or substituted aralkyl$_{(C \leq 12)}$.

13. The pharmaceutical composition of claim 12, wherein R₇ is aralkyl$_{(C \leq 12)}$.

14. The pharmaceutical composition of claim 13, wherein R₇ is benzyl.

15. The pharmaceutical composition of claim 12, wherein R₇ is substituted aralkyl$_{(C \leq 12)}$.

16. The pharmaceutical composition of claim 15, wherein R₇ is 4-chlorophenylmethyl, 2-bromophenylmethyl, or 2-methoxyphenylmethyl.

17. The pharmaceutical composition of claim 1, wherein the composition further comprises a compound of the formula:

[chemical structures]

or a pharmaceutically acceptable salt thereof.

18. A method of treating a neurodegenerative disease or disorder associated with Hsp70 or Hsp90 in a patient comprising administering to the patient in need thereof a therapeutically effective amount of the pharmaceutical composition of claim 1.

19. A method of inducing expression of a Hsp70 protein comprising contacting the protein with an effective amount of the pharmaceutical composition of claim 1 sufficient to induce the expression of the Hsp70 protein.

* * * * *